US006287857B1

(12) United States Patent
O'Riordan et al.

(10) Patent No.: US 6,287,857 B1
(45) Date of Patent: *Sep. 11, 2001

(54) NUCLEIC ACID DELIVERY VEHICLES

(75) Inventors: Catherine R. O'Riordan, Boston; Samuel C. Wadsworth, Shrewsbury, both of MA (US)

(73) Assignee: Genzyme Corporation, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/426,680

(22) Filed: Oct. 25, 1999

Related U.S. Application Data

(63) Continuation-in-part of application No. PCT/US99/02680, filed on Feb. 8, 1999.
(60) Provisional application No. 60/107,471, filed on Nov. 6, 1998, and provisional application No. 60/135,092, filed on Feb. 9, 1998.

(51) Int. Cl.[7] .............................. C12N 15/63; C07H 21/04
(52) U.S. Cl. ...................... 435/320.1; 536/23.1; 536/24.2
(58) Field of Search ........................ 435/320.1; 530/350; 536/23.1, 24.2

(56) References Cited

U.S. PATENT DOCUMENTS

| | | | | |
|---|---|---|---|---|
| 5,753,499 | * | 5/1998 | Meruelo et al. ................... | 435/320.1 |
| 5,798,209 | * | 8/1998 | Chan ......................................... | 435/6 |

FOREIGN PATENT DOCUMENTS

| | | | |
|---|---|---|---|
| WO 93 09221 A | | 5/1993 | (WO) . |
| WO 97/05266 | * | 2/1997 | (WO) .................................. 435/455 |

OTHER PUBLICATIONS

Takakura et al. Control of pharmacokinetic profiles of drug–macromolecule conjugates. Advanced Drug Delivery Reviews. vol. 19:377–399, Mar. 1996.*
Tabata et al. Liver targetting of interferon through pullulan conjugation. Proceed. Intern. Symp. Control, Rel. Bioact. Mater. vol. 23:671–672, Oct. 1996.*
Hirota et al. Targeting cancer therapy in mice by use of newly developed immunoliposomes bearing adriamycin. J. Liposome Res. vol. 1(1):15–33, Jan. 1989.*
Goldman et al., "Targeted Gene Delivery to Kaposi's Sarcome Cells via the Fibroblast Growth Factor Receptor," *Cancer Research,* vol. 57, Apr. 15, 1997, pp. 1447–1451.
Rogers et al., "Use of a novel cross–linking method to modify adenovirus tropism," *Gene therapy,* vol. 4, 1997, pp. 1387–1392.
Douglas et al., "Targeted gene delivery by tropism–modified adenoviral vectors," *Nature Biotechnology,* vol. 14, Nov. 1996, pp. 1574–1578.
Wichham et al., "Targeted Adenovirus Gene Transfer to Endothelial and Smooth Muscle Cells y Using Bispecific Antibodies," Journal of Virology, vol. 70, No. 10, Oct. 1996, pp. 6831–6838.
Wicham et al., "Increased in Vitro and In Vivo Gene Transfer by Adenovirus Vectors Containing Chimeric Fiber PRoteins," Journal of Virology, vol. 71, No. 11, Nov. 1997, pp. 8221–8229.
Fasbender et al., "Complexes of Adenovirus with Polycationic Polymers and Cationic Lipids Increase the Efficiency of Gene Transfer in Vitro and in Vivo," Journal of Biological Chemistry, vol. 272, No. 10, Mar. 7, 1997, pp. 6479–6489.
Moradpour et al., "Specific Targeting of Human Hepatocellular Carcinoma Cells by Immunoliposomes in Vitro," *Hepatology,* vol., 22, 1995, ppl 1527–1537.
Zabner et al., "Adenovirus–Mediated Gene Transfer Transiently Corrects the Chloride Transport Defect in Nasal Epithelia of Patients with Cystic Fibrosis," *Cell,* vol. 75, Oct. 22, 1993, pp. 207–216.

* cited by examiner

*Primary Examiner*—Terry McKelvey
*Assistant Examiner*—William Sandals
(74) *Attorney, Agent, or Firm*—Steven R. Lazar

(57) ABSTRACT

This invention describes a nucleic acid delivery vehicle construct for transfecting and/or infecting a target cell. The construct is made of a delivery vehicle and a bifunctional complex for linking the delivery vehicle to a target cell. The bifunctional complex has a delivery vehicle-binding molecule or fragment ("delivery vehicle-binding portion"), a molecule or fragment thereof that binds to a cell surface molecule on the target cell ("cell surface molecule-binding portion") and a linker which connects the molecules or fragments.

2 Claims, 23 Drawing Sheets

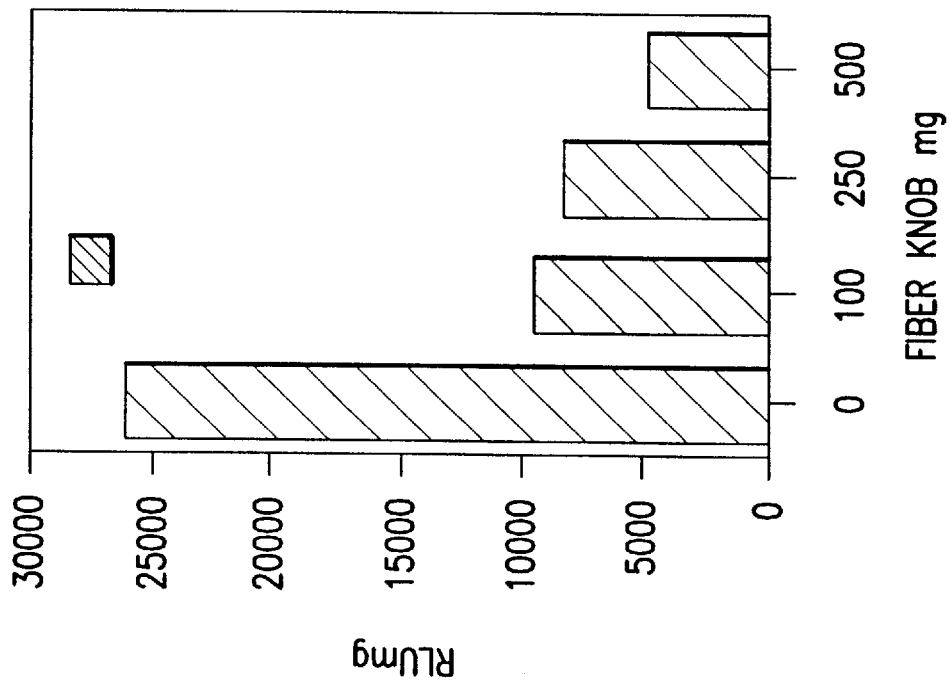
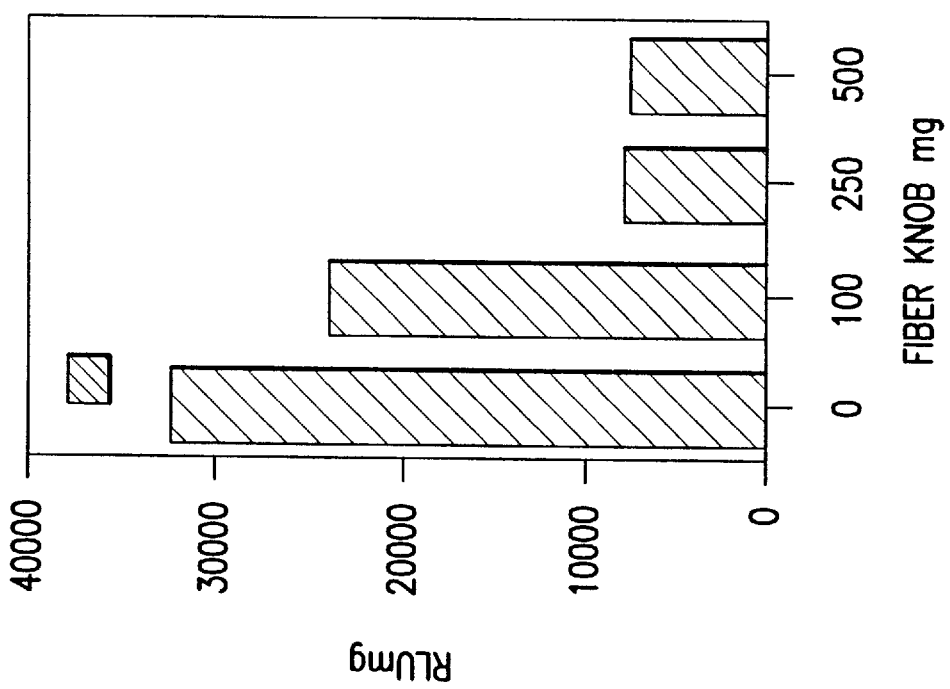

SEQUENCE LISTING

```
<160> NUMBER OF SEQ ID NOS: 25

<210> SEQ ID NO 1
<211> LENGTH: 15
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 1

Lys Gly Gly Cys Arg Gly Asp Met Phe Gly Cys Gly Asp
 1               5                   10

Gly Cys
    15

<210> SEQ ID NO 2
<211> LENGTH: 16
<212> TYPE: PRT
```

-continued

```
<213> ORGANISM: bordetell pertussis
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 2

Lys Ala Thr Ile Arg Arg Gly Asp Ala Leu Ala Asp Gly
 1               5                  10

Gly Ala Cys
    15

<210> SEQ ID NO 3
<211> LENGTH: 12
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 3

Lys Pro Ala Arg Gly Asp Ser Ser Val Asp Gly Cys
 1               5                  10

<210> SEQ ID NO 4
<211> LENGTH: 14
<212> TYPE: PRT
<213> ORGANISM: viper
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 4

Lys Gly Arg Ala Arg Gly Asp Asn Pro Asp Gly Asp Gly
 1               5                  10
      Cys

<210> SEQ ID NO 5
<211> LENGTH: 13
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 5

Lys Ala Cys Arg Gly Asp Gly Trp Cys Gly Asp Gly Cys
 1               5                  10

<210> SEQ ID NO 6
<211> LENGTH: 15
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 6

Lys Ala Cys Pro Ser Arg Leu Asp Ser Pro Cys Gly Asp
 1               5                  10
```

```
Gly Cys
    15

<210> SEQ ID NO 7
<211> LENGTH: 15
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 7

Lys Ala Cys Asp Cys Arg Gly Asp Cys Phe Cys Gly Asp
 1               5                  10

Gly Cys
    15

<210> SEQ ID NO 8
<211> LENGTH: 13
<212> TYPE: PRT
<213> ORGANISM: human
<220> FEATURE:
<221> NAME/KEY: DISULFID
<222> LOCATION: (0)...(0)
<221> NAME/KEY: PEPTIDE
<222> LOCATION: (0)...(0)

<400> SEQUENCE: 8

Lys Cys Asp Cys Arg Gly Asp Cys Phe Gly Asp Gly Cys
 1               5                  10

<210> SEQ ID NO 9
<211> LENGTH: 7
<212> TYPE: PRT
<213> ORGANISM: human
<220> FEATURE:
<221> NAME/KEY: PEPTIDE
<222> LOCATION: (0)...(0)

<400> SEQUENCE: 9

Gly Arg Gly Asp Ser Pro Cys
 1               5

<210> SEQ ID NO 10
<211> LENGTH: 5
<212> TYPE: PRT
<213> ORGANISM: human
<220> FEATURE:
<221> NAME/KEY: PEPTIDE
<222> LOCATION: (0)...(0)

<400> SEQUENCE: 10

Arg Gly Asp Phe Cys
 1               5

<210> SEQ ID NO 11
<211> LENGTH: 7
<212> TYPE: PRT
<213> ORGANISM: human
<220> FEATURE:
<221> NAME/KEY: PEPTIDE
<222> LOCATION: (0)...(0)

<400> SEQUENCE: 11

Cys Arg Gly Asp Cys Leu Cys
```

```
                            1               5

<210> SEQ ID NO 12
<211> LENGTH: 9
<212> TYPE: PRT
<213> ORGANISM: human
<220> FEATURE:
<221> NAME/KEY: PEPTIDE
<222> LOCATION: (0)...(0)

<400> SEQUENCE: 12

Cys Asp Cys Arg Gly Asp Cys Phe Cys
  1               5

<210> SEQ ID NO 13
<211> LENGTH: 12
<212> TYPE: PRT
<213> ORGANISM: human
<220> FEATURE:
<221> NAME/KEY: PEPTIDE
<222> LOCATION: (0)...(0)

<400> SEQUENCE: 13

Cys Asn Arg Cys Val Ser Gly Cys Ala Gly Arg Cys
  1               5                  10

<210> SEQ ID NO 14
<211> LENGTH: 5
<212> TYPE: PRT
<213> ORGANISM: human
<220> FEATURE:
<221> NAME/KEY: PEPTIDE
<222> LOCATION: (0)...(0)

<400> SEQUENCE: 14

Cys Asn Gly Arg Cys
  1               5

<210> SEQ ID NO 15
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 15

Thr Thr Asp Phe Tyr Tyr Ala Leu Arg Ala Leu Ala
  1               5                  10

<210> SEQ ID NO 16
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 16

Thr Thr Asp Phe Tyr Tyr Ala Leu Arg Ala Leu Ala
  1               5                  10

<210> SEQ ID NO 17
<211> LENGTH: 12
```

```
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 17

Leu Pro Lys Met Ala Ser Val Gln Arg Asn Leu Ala
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 18

His Glu Thr Phe Tyr Ser Met Ile Arg Ser Leu Ala
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 19

His Asp Thr Phe Leu Tyr Gly Leu Gln Arg Leu Val
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 20

Leu Thr Phe Asp Gln Thr Pro Leu Thr Ala Gln Ile
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 21

Ile Thr Phe Asn Gln Thr Val Thr Thr Ser Tyr Met
 1               5                  10

<210> SEQ ID NO 22
```

```
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 22

Glu Thr Phe Ser Asp Pro Leu Ala Gly Ser Ser Ser
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: randomly synthesized peptide
<220> FEATURE:
<221> NAME/KEY: PEPTIDE
<222> LOCATION: (0)...(0)

<400> SEQUENCE: 23

Ser Asp Gln Leu Ala Ser Pro Tyr Ser His Pro Arg
 1               5                  10

<210> SEQ ID NO 24
<211> LENGTH: 18
<212> TYPE: PRT
<213> ORGANISM: Artificial Sequence
<220> FEATURE:
<223> OTHER INFORMATION: positively charged peptide artificially
      synthesized
<220> FEATURE:
<221> NAME/KEY: PEPTIDE
<222> LOCATION: (0)...(0)

<400> SEQUENCE: 24

Cys Gly Ser Gly Ser Gly Ser Gly Ser Gly Ser Lys Lys
 1               5                  10

Lys Lys Lys Lys Lys
       15

<210> SEQ ID NO 25
<211> LENGTH: 32
<212> TYPE: PRT
<213> ORGANISM: Artificial Sequence
<220> FEATURE:
<223> OTHER INFORMATION: positively charged peptide artificially
      synthesized
<220> FEATURE:
<221> NAME/KEY: PEPTIDE
<222> LOCATION: (0)...(0)

<400> SEQUENCE: 25

Cys Gly Ser Gly Ser Gly Ser Gly Ser Gly Ser Lys Lys
 1               5                  10

Lys Lys Lys Lys Lys Lys Lys Lys Lys Lys Lys Lys
       15                  20                  25

Lys Lys Lys Lys Lys Lys
         30
```

NUCLEIC ACID DELIVERY VEHICLES

This application is a continuation-in-part of International Application No. PCT/US99/02680, filed Feb. 8, 1999, which claims priority to U.S. Provisional Application No. 60/107,471, filed Nov. 6, 1998 and of the U.S. application Ser. No. 09/020,483, filed on Feb. 9, 1998, and was converted to a provisional application 60/135,092 via petition filed on Nov. 3, 1998, which is now abandoned.

FIELD OF THE INVENTION

This invention relates to nucleic acid delivery vehicle constructs that have an enhanced capability of recognizing and entering target cells.

BACKGROUND OF THE INVENTION

The ability to deliver nucleic acids carried by delivery vehicles, e.g., recombinant viruses (adenovirus, adeno-associated virus, herpesvirus, retrovirus); lipid vehicles, poly-lysine vehicles, synthetic polyamino polymer vehicles which are used with nucleic acid molecules, such as a plasmid, comprising a transgene, to a transfect a target cell; molecular conjugate vectors; and modified viral vectors (adenovirus dodecahedron and recombinant adenovirus conglomerates) to specific cell types is useful for various applications in oncology, developmental biology and gene therapy.

Adenovirus is a non-enveloped, nuclear DNA virus with a genome of about 36 kb. See generally, Horwitz, M. S., "Adenoviridae and Their Replication," in *Virology*, 2nd edition, Fields et al., eds., Raven Press, New York, 1990. Recombinant adenoviruses have advantages for use as expression systems for nucleic acid molecules coding for, inter alia, proteins, ribozymes, RNAs, antisense RNA that are foreign to the adenovirus carrier (i.e. a transgene), including tropism for both dividing and non-dividing cells, minimal pathogenic potential, ability to replicate to high titer for preparation of vector stocks, and the potential to carry large inserts. See Berkner, K. L., 1992, *Curr. Top. Micro Immunol*, 158:39–66; Jolly D., 1994, *Cancer Gene Therapy*, 1:51–64.

Adenoviruses have a natural tropism for respiratory tract cells, which has made them attractive vectors for use in delivery of genes to respiratory tract cells. For example, adenovirus vectors have been and are being designed for use in the treatment of certain diseases, such as cystic fibrosis (CF): the most common autosomal recessive disease in Caucasians. In CF, mutations in the cystic fibrosis transmembrane conductance regulator (CFTR) gene disturb cAMP-regulated chloride channel function, resulting in pulmonary dysfunction. The gene mutations have been found to encode altered CFTR proteins which cannot be translocated to the cell membrane for proper functioning. The CFTR gene has been introduced into adenovirus vectors to treat CF in several animal models and human patients. Particularly, studies have shown that adenovirus vectors are fully capable of delivering CFTR to airway epithelia of CF patients, as well as airway epithelia of cotton rats and primates. See e.g., Zabner et al., 1994, *Nature Genetics*, 6:75–83; Rich et al., 1993, *Human Gene Therapy*, 4:461–476; Zabner et al., 1993, *Cell*, 75:207–216; Zabner et al., 1994, *Nature Genetics* 6:75–83; Crystal et al., 1004, *Nature Genetics*, 8:42–51; Rich et al., 1993, *Human Gene Therapy*, 4:461–476.

However, it would be useful to alter the tropism of a virus, such as adenovirus, to allow it to be used to deliver a nucleic acid molecule to a variety of cells for which the virus is normally non-tropic.

Adenoviruses are about 65–80 nm in diameter and are regular icosahedrons, having 20 triangular surfaces and 12 vertices. A "fiber" projects from each vertex. There are currently approximately 42 known serotypes of adenovirus. The individual serotypes have different properties such as different fiber lengths. The protein coat, or capsid, of the adenovirus has approximately 252 subunits: 240 "hexons" and 12 "pentons". The pentons each have a penton base on the surface of the capsid and a fiber which projects from the base. Each fiber is surrounded by 5 hexons. The hexons and pentons are derived from 25 different viral polypeptides. Horwitz, M. S., "Adenoviridae and Their Replication", in *Virology*, 2nd ed., Fields et al., eds., Raven Press, New York, 1990, p. 1680.

As presently understood, adenovirus enters cells, e.g., in the respiratory tract, by attaching via the fiber to a cell surface receptor (known as CAR for Coxsackie adenovirus receptor) on the cell membrane of the host cell. The virus attached to its receptor migrates into the cell, within the plasma membrane to clathrin-coated pits, which form endocytic vesicles or receptosomes. Horwitz, M. S., "Adenoviridae and Their Replication", in *Virology*, 2nd ed., Fields et al., eds., Raven Press, New York, 1990, p. 1680. When the virus reaches the nuclear pores, the viral DNA enters the nucleus, leaving many virion proteins in the cytoplasm. Horwitz, M. S., "Adenoviridae and Their Replication", in *Virology*, 2nd ed., Fields et al., eds., Raven Press, New York, 1990, p. 1680.

It would be useful to mediate infection of the host cell by controlling the targeting of the adenovirus to cell surface molecules to which adenovirus does not normally bind. In this way the rate of infection can be controlled and the adenovirus can be targeted to certain cells or tissues within an organism.

Like adenoviruses, retroviruses have also been used for delivery of transgenes to target cells. As set forth above, a transgene is a nucleic acid molecule that codes for, inter alia, a protein, RNA, ribozyme, antisense RNA not produced by the virus. Retrovirus virions range in diameter from 80 to 130 nm and are made up of a protein capsid that is lipid encapsulated. The viral genome is encased within the capsid along with the proteins integrase and reverse transcriptase. The retrovirus genome consists of two RNA strands. After the virus enters the cells, the reverse transcriptase synthesizes viral DNA using the viral RNA as its template. The cellular machinery then synthesizes the complementary DNA which is then circularized and inserted into the host genome. Following insertion, the viral RNA genome is transcribed and viral replication is completed.

Examples of retroviruses include Moloney murine leukemia virus (Mo-MuLV), HTLV and HIV retroviruses. Mo-MuLV vectors are most commonly used and are produced simply by replacing viral genes required for replication with the desired transgenes to be transferred. The genome in retroviral vectors contains a long terminal repeat sequence (LTR) at each end with the desired transgene or transgenes in between. The most commonly used system for generating retroviral vectors consists of two parts, the retroviral vector and the packaging cell line.

Retroviruses are typically classified by their host range. For example, ecotropic viruses are viruses which bind receptors unique to mice and are only able to replicate within the murine species. Xenotropic viruses bind receptors found on all cells in most species except those of mice. Polytropic and amphotropic viruses bind different receptors found in both murine and nonmurine species. The host range is determined primarily by the binding interaction between viral envelope glycoproteins and specific proteins on the host cell surface that act as viral receptors. For example, in murine cells, an amino acid transporter serves as the receptor for the envelope glycoprotein gp70 of ecotropic Moloney murine leukemia virus (Mo-MuLV). The receptor for the amphotropic MoMuLV has recently been cloned and shows homology to a phosphate transporter. There are six known receptors for retroviruses: CD4 (for HIV); CAT (for MLV-E (ecotropic Murine leukemic virus E); RAM1/GLVR2 (for murine leukemic virus-A (MLV-A)); GLVRI (for Gibbon Ape leukemia virus (GALV) and Feline leukemia virus B (FeLV-B). RAM1 and GLVR1 receptors are broadly expressed in human tissues.

Retrovirus packaging cell lines provide all the viral proteins required for capsid production and the virion maturation of the vector, i.e., the gag, pol and env genes. For the MMLV vectors, it is the packaging cell line that determines whether the vector is ecotropic, xenotropic or amphotropic. The choice of the packaging cell line determines the cells that will be targeted. Thus, the usefulness of retroviruses for gene transfer is limited by the fact that they are receptor specific.

However, retroviruses are useful for gene delivery systems because they have a high infection efficiency and the retroviral nucleic acid (after reverse transcription) integrates into the host genome resulting in sustained expression of the transgenes carried by the vector. However, typical retroviral vectors are limited in that they require dividing cells for infectivity. Furthermore, in vivo delivery of these vectors is poor and is effective only when infecting helper cell lines. Thus, it would be useful to have a system for increasing the efficiency of retroviral infection.

Certain situations exist where it would be useful to modify the tropism of viruses to target the vector to cell surface molecules other than the virus' normal cells surface receptor. For example, certain cells are normally refractory to infection by certain viruses. It would be useful to have a method of overcoming the inability of these cells to be infected. Similarly, in cancer cells, many receptors are up-regulated. Therefore, it would be useful to be able to specifically target vectors to these up-regulated receptors to increase the uptake of nucleic acids providing for antitumor agents for treatment of such cancers. For example, in Karposi's sarcoma (Prism), there is an increase in the number and activity of receptors for fibroblast growth factor. Thus, this receptor would function as a useful target for infection/transfection. There are a number of additional cell surface molecules that are also specific for various cell types and it would be useful to employ these molecules for targeted infection/transfection as well.

In cystic fibrosis (CF) studies, airway epithelial cells have been infected with adenovirus comprising DNA encoding for CFTR. However, the efficiency of infection of such vectors has proven to be low, leading to a low efficiency of CFTR DNA expression in cells. Furthermore, in practice, in order to achieve effective transgene transfer into affected cells, the viral vector comprising the transgene is repeatedly administered over a course of time. Such readministration of the viral vector can trigger an immune response within the subject to whom the vector is given, which requires subsequently higher doses or an elimination of infection. If the efficiency of uptake of virus is increased, a lower dose of virus can be used to alleviate certain conditions, which, in turn, may help alleviate the immune response problems which are associated with the readministration of vectors. Thus, it would be useful to have a mechanism by which the targeting of the viral vector can be controlled.

Other delivery vehicles comprising cationic amphiphiles such as lipids, synthetic polyamino polymers (Goldman et al., 1997, *Nat. Biotechnol.* 15:462–466), and poly-lysine (Kollen et al., 1996, *Hum. Gene. Ther.* 7:1577–1586), vehicles which are used with nucleic acid molecules, such as a plasmid, comprising a transgene, to transfect a target cell, are useful for delivery of nucleic acids to cells (herein after described as lipid vehicle, synthetic polyamino polymer vehicles, and poly-lysine vehicles). Most of these delivery vehicles suffer from nonspecificity and inefficiency of delivery. Therefore, a method for targeting these systems to cells would also be useful.

Additionally, modified viral systems utilizing the adenovirus dodecahedron which consists of a dodecahedron made of adenovirus pentons or penton bases which are a complex of a penton base and a fiber and allow for internalization and liberation of virus into the cytoplasm (Fender et al., 1997, *Nature Biotechnology* 15:52–56), and recombinant adenovirus conglomerates where the transgene to be transferred is in the genome of a recombinant replication-incompetent adenovirus which also acts as the endosomolytic agent (Schwarzenberger et al., 1997, *J. Virol*; 71:8563–8571) are useful for the delivery of nucleic acids to cells. These delivery vehicles suffer the same inadequacies as discussed above for virus delivery vehicles (e.g. low infectivity). A system which allows for specific targeting of these delivery vehicles would be advantageous.

U.S. Pat. No. 5,574,146 ('146) discloses a method for targeted oligonucleotide delivery to cells utilizing proteolytically cleavable peptides to link an oligodeoxynucleotide (ODN) to a targeting moiety. The '146 invention is dependent upon the proteolytically cleavable peptide being cleaved upon entry into the cell by lysosomal proteases, thereupon releasing the ODN within the cell. Furthermore, the invention in the '146 patent requires the use of automated techniques to synthesize the ODN sequences in order to produce an ODN whose nucleotide sequence comprises a reactive group capable of linking to a reactive group of the proteolytically cleavable peptide. This synthesis requirement limits the length of the ODN in the range of 5 to 100 nucleotides due to the limits of automated synthesis. Such short ODNs generally would not be sufficient to encode a full-length protein or polypeptide molecule capable of replacing an endogenous mutated molecule or providing for an otherwise desirable non-existent full-length protein, RNA, DNA, antisense molecule in the cell. Moreover, the '146 patent necessitates the use of a lysosomotropic agent for the internalization of the ODN into the cell. Therefore, the invention disclosed in the '146 patent is significantly limited in scope to the delivery of small nucleic acid molecules (5 to 100 nucleotides in length) through the use of proteolytically cleavable peptides via lysosomotropic agents.

Additionally, WO 98/39464, WO 98/39465, and WO 98/39467 disclose a method for targeting specific cell populations to express a protein of interest. This is achieved by the use of a recombinant adenovirus vector, which comprises a first adenovirus gene under transcriptional control of a first heterologous transcriptional regulatory element (TRE), and at least a second gene under control of a second heterologous TRE, wherein the first heterologous TRE is cell-specific, and both heterologous TREs are functional in the same cell. The first adenovirus gene is essential for adenovirus replication and the second gene may be a transgene of interest. The recombinant adenovirus vectors are thereby limited to replicating only in the target cell, although all cells may be infected with the recombinant adenovirus vector. The invention also provides for a method whereby the immunogenicity of the recombinant adenovirus vector is masked by being complexed with35 a non-immunogenic hydrophilic polymer which may be complexed to the recombinant adenovirus vector by covalent or non-covalent attachment to the capsid proteins of the virus. The preferred hydrophilic polymer is polyethylene glycol covalently linked through a tresyl-MPEG (TMPEG) to adenovirus ("linked through ε-amino groups on lysine residues on the adenovirus using TMPEG). Such treatment of the virus is not involved in the targeting mechanism and solely achieves the task of reducing the immunogenicity of the recombinant virus vector. The three aforementioned patent applications all employ a similar method although the TREs vary among them. The potential problem with such an invention is that it cannot ensure that cells that are not being targeted but may be infected will not exhibit any leaky expression of the transgene. Where the transgene of interest is a cytotoxic gene, leaky expression would be highly undesirable.

It would be useful to have a method of linking nucleic acid delivery systems capable of delivering a nucleic acid molecule, regardless of composition and size, to specific cell surface molecules to stimulate uptake of the delivery vehicle into the cells such that only the cells that are targeted will internalize the delivery vehicle.

For example, major histocompatibility complex ("MHC") molecules are found in on essentially all nucleated cells and assist in T-cell mediated immune response. In human cells, MHC molecules are also called human-leukocyte antigens ("HLA antigens"), There are two classes of MHC molecules, class I and class II. Class I MHC molecules are polymorphic integral membrane proteins that bind a diverse group of foreign antigens or self-antigens for presentation to T cells. The extracellular portion of Class I MHC heavy (H) chains comprises three structural domains, $\alpha_1$, $\alpha_2$ and $\alpha_3$. These H chains are noncovalently associated in an equimolar ratio with $\beta_2$-microglobulin, a soluble, nonpolymorphic protein. Helper T cells react against foreign Class II glycoproteins. The Class II glycoproteins are composed of two noncovalently bonded polypeptide chains: an α-chain with a molecular weight of about 33,000 and a β-chain with a molecular weight of about 28,000. MHC molecules are found on a wide variety of cell types and are efficiently internalized by endocytosis in numerous cell types.

Alberts, et al. indicates that antigens seen by T cells are degraded inside a host cell before they are presented to the T cell on the surface of the host sell. The fragments of viral proteins wind up on the surface of the infected cell by associating with MHC molecules either on the surface of the cells or perhaps inside the cell. Alberts, et al., 1986, *Molecular Biology of the Cell*, $2^{nd}$ ed., p. 1043.

Class I MHC molecules are continuously shuttling peptides back and forth from the endoplasmic reticulum (ER) to the plasma membrane at the surface of the cell. The MHC peptide complex can bind to the T-cell receptor complex which in turn leads to activation of the T-cell. The structure and the fate of Class I MHC molecules in both the ER and on the cell surface are regulated by peptides in the cell and $\beta_2$-microglobulin. For example, a high local concentration of $\beta_2$-microglobulin plays an important role in maintaining Class I MHC chains in a conformation accessible to peptides. This high level of $\beta_2$-microglobulin in the ER can increase the efficiency with which Class I MHC molecules bind peptides for transport to the cell surface. Conversely, the inherent instability of free Class I MHC H chains in the presence of low $\beta_2$-microglobulin concentrations serves to limit the number of cell surface class I molecules that can capture extracellularly derived antigenic peptides for presentation to T-cells.

Roux et al. described an approach to target nucleic acid molecules to specific cell types using retroviruses. Roux, P., et al., 1989, *Proc. Nat. Acad. Sci. USA*, 86, 9079–9083. This approach used biotinylated antibodies to the retroviral envelope protein connected to biotinylated antibodies to specific cell membrane markers by streptavidin. According to this method, a first bifunctional antibody complex containing a biotinylated anti-major histocompatibility complex (MHC) antibody is added to the cells which are to be infecteditransfected. The cells are then washed and incubated with streptavidin, and then washed again. This process results in a cell/anti-MHC-biotin/streptavidin complex. Then the retrovirus of interest is incubated with biotinylated anti-gp-70 antibodies to create precoated retroviruses. Gp-70 is a virus-encoded glycoprotein which binds to specific cell membrane receptors. The precoated retroviruses are then added to the MHC-streptavidin complex. The result is a linking of the retrovirus to the MHC cell receptor via a biotinylated anti-MHC antibody/streptavidinlbiotinylated anti-gp-70 antibody bridge. As stated by the authors, a major limitation of this approach is the relatively low infection yield. Roux, P., et al., 1989, *Proc. Nat. Acad. Sci. USA*, 86, 9079–9083. Thus, the usefulness of this approach is rather limited. Furthermore, this approach cannot be used in vivo because the target cells in vivo cannot be pre-incubated with streptavidin. Furthermore, streptavidin is known to be immunogenic. Marshall, D., et al., 1996, *British Journal of Cancer*, 73 (5):562–72.

Other examples of useful specific cell surface receptors include the following: (1) The folate receptor. The folate receptor is over-expressed on the cell surface of a variety of human tumors, including those of the ovary, kidney, uterus, testis, brain, colon, lung and myelocytic blood cells, and can be used as a receptor for targeted delivery vehicles. Either folate, or an antibody against the folate receptor (Melani et al., 1998, *Cancer Res.* 58(18):4146–4154) can be bound to the receptor for use as cell surface binding portions. (2) The transferrin receptor. The expression of the transferrin receptor correlates with cellular proliferation, its levels being highest among dividing cells, including a variety of tumor cells. Shindelman et al., 1981, Int J Cancer 27:329–334. In breast tissue, transferrin receptor expression has been related to the presence of malignancy (Faulk et al., 1980, *Lancet* 2:390–392). Transferrin receptor expression also occurs in lung and colon adenocarcinomas, some sarcomas and some forms of Hodgkin's disease. Gatter et al., 1983, *J. Clin. Pathol.* 36:539–545. Transferrin, or an antibody against the transfernin receptor, for example HB21, a Fab fragment of a monoclonal antibody directed against the human transferrin receptor (Debinski and Pastan, 1992, *Cancer Res.* 52:5379–5385), can be used for targeting the transferrin receptor. (3) The fibroblast growth factor (FGF) receptor. FGF receptors are endogenously expressed on the cell surface of Karposi sarcoma cells. Goldman et al., 1997, *Cancer Res.* 57:1447–1451. Karposi sarcoma is a major AIDS related malignancy associated with a significant morbidity and mortality.

Fibroblast growth factor (FGF2) can be used to target cells expressing the FGF receptor. (4) Epidermal growth factor (EGF) receptor. As with the FGF receptor, the EGF receptor may be targeted by the epidermal growth factor (EGF). Bell et al., 1986, *Nucleic Acids Res.* 21:8427–8447. (5) The c-kit receptor may also be targeted by molecules that bind to it. Schwarzenberger et al., 1996, *Blood* 87:472–478. (6) The erythrocyte growth factor receptor is also up-regulated on the cell surface of many tumor cells. It can be targeted using an antibody to the receptor, e.g. monoclonal antibody B4G7. Shimizu et al., 1996, *Cancer Gene Therapy* 3:113–120. The receptor may also be targeted using the erythrocyte growth factor. (7) Polymeric Ig Receptor. The polymeric Ig receptor is expressed on the basal cell surface of respiratory epithelial cells and are therefore particularly advantageous for targeting since they represent an alternative mechanism for entry into the cell via the bloodstream which is potentially more amenable for therapeutics. Fab fragments against the polymeric Ig receptor may be used for targeting respiratory epithelial cells. (8) The erythropoietin (EPO) receptor can also be used for targeting cells via erythropoietin. Yoshimura and Misawa, 1998, *Curr Opin Hematol.* 5:171–176. (9) The purinoceptor. O'Reilly et al., 1998, *Br. J. Pharmacol.* 124:1597–1606. The purinoceptor can be targeted with purine or purine analogs (e.g. ATP, UTP, ATP-γ-S, AMP-PNP, and INS 365) which bind to the purinoceptor. INS 365 is a purinoceptor agonist described by Shaffer et al. Shaffer et al., 1998, *Pediatric Pulmonology*, Supplement 17, Abstract 198.

Additionally, certain enzymes are found on the cell surface (e.g. metalloproteases) which could also serve as targets of delivery vehicles via small molecules, peptides, or antibodies that bind to these cell surface molecules Small molecules may be particularly useful in targeting delivery vehicles to cells as they may circumvent proteolysis problems that may interfere with the usefulness of peptides, proteins, and antibodies as targeting molecules.

SUMMARY OF THE INVENTION

The present invention relates to a nucleic acid delivery vehicle construct for transfecting/infecting a target cell comprising a delivery vehicle (e.g. virus, modified virus, plasmids, nucleic acid molecules, lipid vehicles, poly-lysine vehicle, or synthetic polyamino polymer vehicles which are used with nucleic acid molecules, such as a plasmid, comprising a transgene, to transfect a target cell) and a bifunctional complex for linking the delivery vehicle to a target cell in order to increase transfection/infection efficiency of the cell with the delivery vehicle. The bifunctional complex comprises (1) a molecule or fragment thereof that binds to the delivery vehicle ("delivery vehicle binding portion"), (2) a molecule or fragment thereof that binds to a cell surface molecule on the target cell ("cell surface molecule binding portion") and a linker which connects the delivery vehicle binding and cell surface binding portions. The cell surface molecule-binding portion is capable of binding to the target cell in vivo and in vitro.

The delivery vehicle can be any delivery vehicle useful for delivery of a nucleic acid into a recipient host cell (e.g. viral vector, plasmids, nucleic acid molecules, lipid vehicle, poly-lysine vehicle, and synthetic polyamino polymer vehicle which complexed with nucleic acid molecules, such as a plasmid, comprising a transgene, to transfect a target cell; and modified viral vehicle). Preferred viral vectors include adenovirus, retrovirus, herpes simplex virus, adeno associated virus or poxvirus, with adenovirus being particularly preferred.

In any one aspect of the invention, the delivery vehicle binding portion of the bifunctional complex comprises a molecule or fragment thereof that binds the delivery vehicle, such as an antibody or a fragment thereof, a peptide, a small molecule, or other ligands, e.g., cationic molecules, such as polycations or cationic lipids. In one preferred embodiment, the delivery vehicle is an adenovirus and the delivery vehicle-binding portion is a ligand that binds to the adenovirus at the hexon or fiber protein. In particular, the molecule or fragment thereof that binds the a adenovirus is an antibody or fragment thereof that binds to the adenovirus hexon or fiber protein.

In other preferred embodiments the virus is a retrovirus and the delivery vehicle-binding portion binds to a retroviral envelope glycoprotein. In a preferred embodiment, the molecule or fragment thereof that binds the retrovirus is an antibody or fragment thereof that binds to the retroviral envelope glycoprotein gp70.

In yet other embodiments, the delivery vehicle comprises an adeno-associated virus (AAV) and the delivery vehicle-binding portion binds to an AAV coat protein. In a preferred embodiment, the molecule or fragment thereof that binds the AAV is an antibody or fragment thereof that binds to AAV coat protein VP1, VP2, or VP3. Similarly, in embodiments in which the delivery vehicle comprises HSV, the HSV binding portion binds to an HSV envelope glycoprotein. For example, the delivery vehicle binding portion comprises an antibody or fragment thereof that binds to one or more of the 10 HSV glycoproteins of the viral envelop, e.g. gD, gC, gB, gH, or gL.

In embodiments in which the delivery vehicle is poxvirus, the delivery vehicle-binding portion binds to the poxvirus outer membrane. Preferably, the poxvirus-binding portion comprises an antibody or fragment thereof, that binds to a poxvirus envelope protein, e.g. ABF11.

In other preferred embodiments, the delivery vehicle-binding portion comprises a cationic molecule, which associates with the negatively charged portion of the delivery vehicle (e.g. a plasmid or a nucleic acid molecule). In another preferred embodiment, the delivery vehicle is a lipid/plasmid complex wherein the lipid portion of the delivery vehicle has been chemically modified to incorporate a charged molecule and the delivery vehicle binding portion of the bifunctional complex comprises another charged molecule which associates with the charged molecule of the chemically modified lipid. In other preferred embodiments of the invention, the charged molecule of the bifunctional complex binds to charged molecules of the poly-lysine, synthetic polyamino polymer, and/or modified viral vehicles.

Cell Surface Molecule Binding Portion:.

The cell surface molecule-binding portion of the bifunctional complex comprises a molecule or fragment thereof that binds the cell surface molecule of the target cell of interest. In certain embodiments of the construct of the present invention, the molecule or fragment thereof that binds the cell surface molecule is an antibody or a fragment thereof which binds to a receptor on the cell surface. The receptor preferably comprises a major histocompatibility complex (MHC) molecule, transferrin receptors and integrins, or other cell surface receptors of interest. In a preferred embodiment, the molecule or fragment thereof that binds the cell surface receptor is an antibody or a fragment thereof that binds to an MHC molecule. In particular, the cell surface molecule-binding portion comprises an anti-$\beta_2$-microglobulin antibody/Fab fragment.

In other embodiments, the cell surface molecule comprises an antigen such as AF20 antigen, which is associated with carcinoma cells especially with hepatocarcinoma cells, lung adenocarcinoma cells and colorectal carcinoma cells. In a preferred embodiment, the cell surface molecule-binding portion comprises an antibody or a fragment thereof that binds to the AF20 antigen of carcinoma cells. In an especially preferred embodiment, the cell surface molecule-binding portion comprises the AF20 antibody, or a fragment thereof, which is directed to the AF20 antigen.

In further certain embodiments, the cell surface molecule preferably comprises a receptor, such as the folate receptor, which is over-expressed on a variety of tumors including those of the ovary, kidney, uterus, testis, brains, colon, lung and myelocytic blood cells. In preferred embodiments, the cell surface molecule-binding portion comprises folate or an antibody or a fragment thereof to the folate receptor.

In other embodiments, the cell surface molecule preferably comprises a receptor, such as the transferrin receptor, which is associated with cellular proliferation, especially in breast cancer cells, colon adenocarcinomas, some sarcomas, and some cells associated with Hodgkin's disease. In preferred embodiments, the cell surface molecule binding portion comprises transferrin, an antibody to the transferrin receptor, or a Fab fragment of a monoclonal antibody to the transferrin receptor such as HB21.

In still other certain embodiments, the cell surface molecule preferably comprises a receptor, such as the FGF receptor, which is associated with Karposi sarcoma cells. In preferred embodiments, the cell surface molecule-binding portion comprises fibroblast growth factor-2 (FGF2) or an antibody to the FGF receptor. In further embodiments, the cell surface molecule preferably comprises a receptor, such as the EGF receptor, which is associated with epidermal cells. In preferred embodiments, the cell surface molecule-binding portion comprises epidermal growth factor (EGF) or an antibody to the EGF receptor. In other embodiments, the cell surface molecule preferably comprises the c-kit receptor. In preferred embodiments, the cell surface molecule-binding portion comprises c-kit or an antibody to the c-kit receptor.

In further embodiments, the cell surface molecule preferably comprises a receptor, such as erythrocyte growth factor receptor, which is associated with many tumor cells. In preferred embodiments, the cell surface molecule-binding portion comprises erythrocyte growth factor or an antibody to the erythrocyte growth factor receptor such as, monoclonal antibody B4G7. In certain other embodiments, the cell surface molecule preferably comprises a receptor, such as VEGF receptor, which is found on vascular endothelial cells. In preferred embodiments, the cell surface molecule-binding portion comprises VEGF or an antibody to the VEGF receptor.

In still other certain embodiments, the cell surface molecule preferably comprises a receptor which is associated with respiratory epithelial cells (e.g. polymeric immunoglobulin receptor which is expressed on the basal lateral surface of the cell). In preferred embodiments, the cell surface molecule-binding portion comprises a Fab antibody fragment to the polymeric immunoglobulin receptor. In yet further embodiments, the cell surface molecule preferably comprises the purinoceptor. In preferred embodiments, the cell surface molecule binding portion comprises a purine or a purine analog (ATP, UTP, ATP-γ-S, AMP-PNP, INS 365) or an antibody to the purinoceptor.

In still other certain embodiments, the cell surface molecule preferably comprises the endogenous receptors or co-receptors of adenoviruses. In preferred embodiments, the cell surface molecule binding portion comprises a peptide identified by phage biopanning of a displayed peptide library on separate domains of wild-type and mutant adenovirus penton capsomeres (Hong et al., 1995, *EMBO* 14:4714–4727).

In still further preferred embodiments, the cell surface molecule binding portion comprises a peptide with avidity for the target cell of interest. In preferred embodiments, the peptide is identified by phage biopanning techniques (Smith, G. P. and Scott, J. K., 1993, *Methods in Enzymol.* 217:228–257) or other techniques which select for peptides capable of cell surface binding. In especially preferred embodiments of the invention, the peptide has avidity for differentiated, ciliated human airway cells, isolated by phage biopanning techniques.

The invention further relates to bi-functional linkers which link the delivery vehicle binding portion to the cell surface molecule-binding portion. In preferred embodiments of the present invention, the linker comprises a chemical linker, including covalent or ionic linkages. Examples of covalent linkers include, but are not limited to, sulfhydryl and maleimide linkages. Examples of ionic bond linkages include, but are not limited to, cationic molecules such as poly-L-lysine (PLL) and polyethylene glycol-PLL (PEG-PLL).

Additional linkers include biocompatible polymers having an average weight of 200 to 20,000 daltons which may be chemically modified to be used as linkers.

In a particularly preferred embodiment, the delivery vehicle comprises adenovirus and the cell surface molecule binding portion comprises MHC I molecules. In one preferred construct of the present invention, the bifunctional complex comprises an anti-hexon Fab fragment covalently attached to an anti-$\beta_2$-microglobulin Fab fragment.

In another particularly preferred embodiment, the delivery vehicle comprises adenovirus and the cell surface molecule-binding portion comprises a peptide directed to airway epithelial cells selected by phage biopanning techniques.

In another particularly preferred embodiment, the delivery vehicle comprises adenovirus and the cell surface molecule-binding portion comprises the AF20 antibody.

In further preferred embodiments, the delivery vehicle comprises adenovirus and the delivery vehicle binding portion comprises an anti-hexon antibody, such as monoclonal antibody 2Hx-2 which is, in turn, linked to the cell surface molecule binding portion which comprises the AF20 antibody, thus forming a bifunctional antibody.

Any cell surface molecule which may be bound by another molecule is potentially useful in this invention. Included are those cell surface molecules which are ubiquitously expressed as well as those selectively expressed on the surface of one or a few cell types.

The invention further relates to a method of making a construct for delivering nucleic acids to a target cell which comprises:

a) providing a bifunctional complex comprising
  i) a molecule or fragment thereof that binds a nucleic acid delivery vehicle;
  ii) a molecule or fragment thereof that binds a cell surface molecule on the target cell; and
  iii) a linker which connects the molecules or fragments thereof, and
b) associating the bifunctional complex with the nucleic acid delivery vehicle.

The invention also relates to the method of making the construct wherein the step of creating the bifunctional complex further comprises chemically modifying the molecules to create the chemical linker. In certain preferred embodiments, the chemical linker comprises a maleimide-sulfhydryl linkage. The chemical linker preferably contains a pyridal disulfide group, a disulfide group, or a maleimide group.

The invention further relates to a method of infecting/transfecting cells with a nucleic acid delivery vehicle comprising contacting the cells with a an infection/transfection construct comprising a delivery vehicle and a bifunctional complex for linking the delivery vehicle to the target cell, wherein the bifunctional complex comprises: a) a molecule or fragment thereof that binds the nucleic acid delivery vehicle (delivery vehicle binding portion); b) a molecule or fragment thereof that binds a cell surface molecule on the target cell (cell surface molecule binding portion); and c) a linker which connects the delivery vehicle binding and cell surface molecule binding portions. This method can be practiced in vitro or in vivo.

BRIEF DESCRIPTION OF THE DRAWINGS

FIGS. 14A–D are graphs showing the ability of a bifunctional antibody (2Hx-AF20) to stimulate the uptake of adenovirus in FOCUS cells as measured by β-galactosidase expression levels. The ability of fiber knob to inhibit the infection efficiency of the adenovirus is competed by the addition of increasing amounts of 2Hx-AF20.

DETAILED DESCRIPTION OF THE INVENTION

The nucleic acid delivery vehicle constructs of the present invention enable the transport of a nucleic acid delivery vehicle of interest, e.g., virus (retrovirus; adenovirus; adeno-associated virus (AAV); or herpes simplex virus (HSV)); lipid vehicles, poly-lysine vehicles, synthetic polyamino polymer vehicles which are used with nucleic acid molecules, such as a plasmid, comprising a transgene, to transfect a target cell; and modified viral vehicles into a target cell.

Typically, the delivery vehicle carries a transgene (as set forth above, a transgene is a nucleic acid molecule that codes for, inter alia, a protein, RNA, ribozyme, antisense RNA not produced by the virus to be expressed into target cell) e.g., CFTR, alpha-1-antitrypsin AAT, β-glucocerebrosidase, or suicide gene products. Examples of suicide genes include, inter alia, those that encode HSV thymidine kinase (TK), modified TK, cystine deamninase, E. coli nitroreductase, xanthine-guanine phosphoribosyl transferase, mammalian Pf50 2B1, purine nucleoside phosphorylase, thyridine phosphorylase, deoxycytidine kinase and Varicella Zoster virus thymidine kinase. In a preferred embodiment, the delivery vehicle e.g., an adenovirus, is associated, either covalently or non-covalently, with a bifunctional complex which links the delivery vehicle to a cell surface molecule on the target cell.

The bifunctional complex of the construct of the present invention comprises (a) a portion that specifically binds the nucleic acid delivery vehicle ("delivery vehicle binding portion"), (b) a portion that binds a cell surface molecule on the target cell ("cell surface molecule binding portion") and (c) a linker which connects the delivery vehicle binding and cell surface binding portions. The delivery vehicle-binding portion of the complex binds to the delivery vehicle while the cell surface molecule binding portion binds to a molecule on the surface of the targeted cell. The bifunctional complex thereby targets the delivery vehicle to the cell of interest. The term "cell surface molecule" is used herein to describe any molecule present on the surface of a target cell to which another molecule can be bound, such as, but not limited to, receptors (e.g. MHC molecules, transferrin receptors, folate receptors, fibroblast growth factor receptors, epidermal growth factor receptors, erythrocyte growth factor receptors, c-kit receptor, vascular endothelial growth factor receptor, endogenous receptors and co-receptors of adenoviruses, polymeric immunoglobulin receptors, erythropoietin receptors, purinoceptors) integrins, AF20 antigen, molecules that have affinity for peptides selected by phage biopanning techniques, negatively charged cell membrane molecules, and cell surface enzymes.

Figure 1:
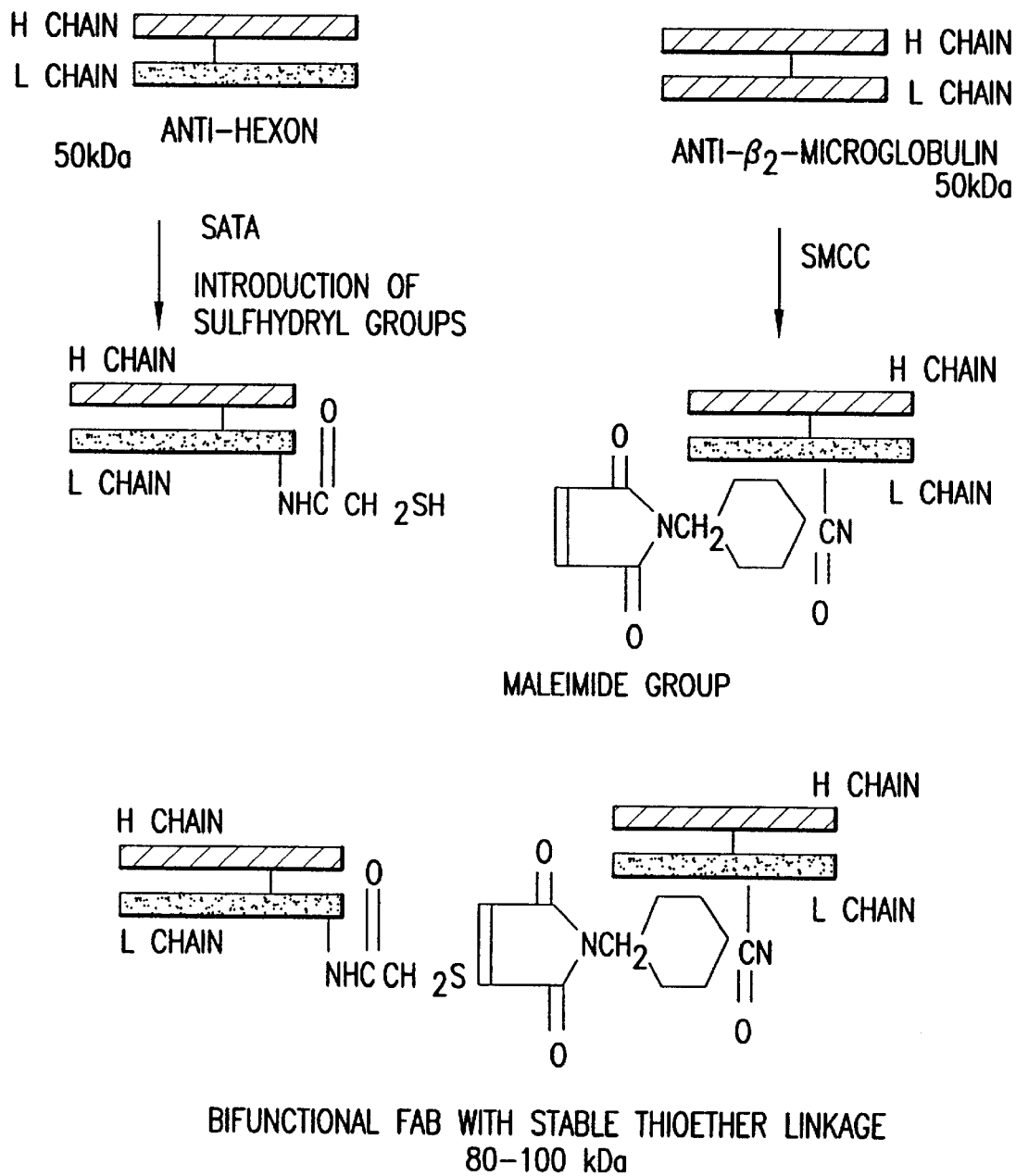
FIG. 1 shows a diagram of the introduction of sulfhydryl groups and sulfhydryl reactive groups into Fab fragments using heterobifunctional reagents.

The methods of the present invention enable the delivery vehicle to be specifically targeted to the cell via the binding to cell surface molecules, e.g., the MHC molecule, transferrin receptors, integrins, antigens such as AF20 antigen, molecules that have affinity for peptides selected by phage biopanning techniques, negatively charged cell membrane molecules, folate receptors, fibroblast growth factor receptors, epidermal growth factor receptors, erythrocyte growth factor receptors, c-kit receptor, endogenous receptors and-co-receptors of adenoviruses, polymeric immunoglobulin receptors, erythropoietin receptors, purinoceptors, and cell surface enzymes. FIG. 1 shows a schematic diagram of an exemplary bifunctional complex. It has been discovered that, after binding to the cell surface molecule, in this case an MHC molecule, the delivery vehicle and bifunctional complex are then taken up by the cell. The construct of the present invention surprisingly increases the efficiency of cellular uptake of the nucleic acid delivery vehicle. The constructs of the present invention also enable the transfection/infection of cells that are normally refractory to transfection/infection by targeting cell receptors that are present on such cells.

Any viral delivery vehicle that is known to be useful in the art for infection is useful in the present invention. Examples of such viral delivery vehicles include: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family (Φ6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; Plant virus satellites.

Additionally, delivery vehicles include, but are not limited to, lipid vehicles, poly-lysine vehicles, synthetic polyamino polymer vehicles, and modified viral vehicles which are used with nucleic acid molecules, such as a plasmid, comprising a transgene, to transfect a target cell.

Particularly preferred delivery vehicles are those delivery vehicles previously employed for the delivery of transgenes including, for example, retrovirus, adenovirus, adeno-associated virus, herpes virus and poxvirus. In a preferred embodiment, the delivery vehicle is an adenovirus or retrovirus, and most preferably the delivery vehicle is an adenovirus.

In certain preferred embodiments of the present invention, the delivery vehicle of interest to be used for infecting cells is an adenovirus. Normally adenoviruses bind to a cell surface receptor (CAR) of susceptible cells via the knob domain of the fiber protein on the virus surface. The fiber knob receptor is a 45 kDa cell surface protein which has potential sites for both glycosylation and phosphorylation. (Bergelson, et al., 1997, *Science* 275:1320–1323. A secondary method of entry for adenovirus is through integrins present on the cell surface. Arginine-Glycine-Aspartic Acid (RGD) sequences of the adenoviral penton base protein bind integrins on the cell surface.

In other preferred embodiments of the present invention, the delivery vehicle of interest is a retrovirus. As previously described, retroviruses normally bind to a species specific cell surface receptor, e.g., CD4 (for HIV); CAT (for MLV-E (ecotropic Murine leukemic virus E); RAM1/GLVR2 (for murine leukemic virus-A (MLV-A)); GLVR1 (for Gibbon Ape leukemia virus (GALV) and Feline leukemia virus B (FeLV-B). However, if the cells of interest do not have such surface receptors, the virus can not infect such cells. The method of the present invention allows the infection of normally refractory cells with a virus of interest. Similarly, if the viral receptors are broadly expressed, e.g., RAM1 and GLVR1 receptors, the constructs of the present inventions are useful for limiting infection to the tissue of interest by specifically targeting the virus to cell surface molecules expressed only on the cell surface of the target tissue.

Other viruses for use in the present invention include adeno-associated viruses (AAV). In vitro production of AAV vectors requires co-infection of producer cells with either adenovirus or herpes simplex virus (HSV). AAV are parvoviruses and are extremely small icosahedral virions, 18–26 nanometers in diameter and contain a single strand DNA molecule 4–5 kilobases in size. AAV have three coat proteins, VP1, VP2 and VP3. The viruses contain either the sense or antisense strand of the DNA molecule and either strand is incorporated into the virion. The DNA molecule contained within the AAV has a palindromic sequence at each end, referred to as the inverted terminal repeat (ITR). These ITRs enable the site-specific integration of AAV DNA into human chromosome 19 which has made them an attractive candidate for the production of a gene therapy vector. The nature of the receptor for AAV is not known but the receptor appears to contain sialic acid since pretreatment of the cells with neuraminidase prevents viral attachment to the cell surface. Cotmore, S. F., et al., 1987, *Adv. Virus Res.* 33:91.

AAV vectors are useful for the delivery of transgenes to cells because they allow for stable integration of transgenes into a target cell, and they infect a range of cells. However, their usefulness has been limited until now. AAV vectors are particularly useful in the present invention since their inherent infection pathway can be inhibited by pre-incubation with neuraminidase. Once the inherent infection pathway is inhibited, only those cells expressing the cell surface molecule which is targeted by the present invention will be infected. This creates a delivery vehicle that only enters the cells of interest and avoids the complication of delivering transgenes to healthy cells. If the object of the delivery vehicle is for the expression of a transgene (such as a suicide gene) which would effectively eliminate a particular cell population (as might be the objective in cancer treatment) such a targeted delivery system is particularly advantageous to reduce undesired cell destruction.

Another preferred delivery vehicle for use in the present invention comprises Herpes Simplex Virus (HSV). Herpes simplex virions have an overall diameter of 150 to 200 nm and a genome consisting of one double-stranded DNA molecule which is 120 to 200 kilobases in length. Glycoprotein D (gD) is a structural component of the HSV envelope which is essential for virus entry into host cells. The initial interaction of HSV with cell surface heparin sulfate proteoglycans is mediated by another glycoprotein, glycoprotein C (gC) and or glycoprotein B (gB). This is followed by interaction with one or more of the viral glycoproteins with cellular receptors. Recently it has been shown that glycoprotein D of HSV binds directly to Herpes virus entry mediator (HVEM) of host cells. HVEM is a member of the tumor necrosis factor receptor superfamily (Whitbeck, J. C. et al., 1997, *J. Virol.*; 71:6083–6093). Finally, gD, gB and the complex of gH and gL act individually or in combination to trigger pH-independent fusion of the viral envelope with the host cell plasma membrane. The virus itself is transmitted by direct contact and replicates in the skin or mucosal membranes before infecting cells of the nervous system for which HSV has particular tropism. It exhibits both a lytic and a latent function. The lytic cycle results in viral replication and cell death. The latent function allows for the virus to be maintained in the host for an extremely long period of time.

HSV can be modified for the delivery of transgenes to cells by producing a vector that exhibits only the latent function for long-term gene maintenance. However, because of its tropism, the virus is limited to expression in cells of the central nervous system. Use of this virus with constructs of the present invention enables the infection of other types of cells with HSV. HSV vectors are useful for transgene delivery because they allow for a large DNA insert of up to or greater than 20 kilobases; they can be produced with extremely high titers; and they have been shown to express transgenes for a long period of time in the central nervous system so long as the lytic cycle does not occur. However, one major disadvantage is that HSVs have low infection efficiency. Thus, use of methods of the present invention with these vectors will circumvent poor infection efficiencies.

Yet another preferred delivery vehicle is poxvirus. These viruses are very complex, containing more than 100 proteins, although the detailed structure of the virus is presently unknown. Extracellular forms of the virus have 2 membranes while intracellular particles only have an inner membrane. The outer surface of the virus is made up of lipids and proteins which surround the biconcave core. Poxviruses are very complex antigenically, inducing both specific and cross-reacting antibodies after infection. Poxvirus receptors are not presently known, but it is likely that there exists more than one given the ability of poxvirus to infect a wide range of cells. Poxvirus gene expression is well studied due to the interest in using vaccinia virus as a vector for expression of transgenes.

When poxvirus is used as a delivery vehicle in the methods and constructs of the present invention, the delivery vehicle binding portions preferably bind to proteins on the outer viral membrane, e.g. envelope proteins. An example of a viral envelope protein of poxvirus which could be used for targeting vaccinia virus is a 14 K envelope protein called AbF11. Rodriguz et al., 1985, *Journal of Virology* 56:482–488. Most preferably, the delivery vehicle-binding portion comprises an antibody or fragment thereof that binds to AbF11.

In preferred embodiments of the bifunctional complex construct of the present invention, the delivery vehicle-binding portion comprises a molecule, or fragment thereof, that binds to the delivery vehicle at sufficiently low concentrations.

Preferably, the delivery vehicle-binding portion does not interfere with the transport and internalization of the delivery vehicle by the target cell or the functioning of the delivery vehicle once it is inside the cell.

In some embodiments of the present invention, the delivery vehicle-binding portion comprises an antibody, or fragment thereof, that specifically binds to the delivery vehicle. In a preferred embodiment, the delivery vehicle-binding portion binds to the adenovirus hexon or fiber protein. In an especially preferred embodiment, the delivery vehicle-binding portion comprises a Fab fragment of an antibody specifically reactive with the hexon protein such as monoclonal antibody 2Hx-2. Other antibodies for use as delivery vehicle binding portions in certain embodiments of the present invention include antibodies or fragments thereof that bind to the penton base protein or the fiber protein of the adenovirus.

In embodiments in which the delivery vehicle is a retrovirus, the delivery vehicle binding portion binds to molecules on the surface of the virus, e.g., viral envelope glycoproteins. In preferred embodiments, the delivery vehicle-binding portion comprises an antibody or fragment thereof that binds to the envelope glycoprotein. For example, for Mo-MuLV, antibodies or fragments thereof against gp-70 can be used for the delivery vehicle-binding portion. An antibody against gp-70 is commercially available (Quality Biotech, Inc., USA) and can be used as part of a bifunctional antibody targeting amphotropic and ecotropic retroviruses. Other useful antibodies to other envelope glycoproteins can be obtained by one of ordinary skill in the art by known methods.

When the virus comprises an AAV, the delivery vehicle-binding portion preferably binds proteins of the viral coat. More preferably, the delivery vehicle binding portion comprises an antibody or fragment thereof that binds to coat proteins. For example, commercial antibodies are available against each of the coat polypeptides VP1, VP2 and VP3. (American Research Products, Belmont, Mass.).

When the delivery vehicle comprises HSV, the delivery vehicle-binding portion preferably binds to one of the virus encoded envelope glycoproteins. More preferably, the delivery vehicle binding portion comprises an antibody or fragment thereof that binds to one of the 10 virus encoded envelope glycoproteins.

In other embodiments of the present invention, the delivery vehicle binding portion of the bifunctional complex comprises other ligands, e.g., cationic molecules. Examples of cationic ligands include e.g., poly-L-lysine (PLL), DEAE-dextran, poly-D-lysine (PDL), poly-ethyleneimine (PEI), and polyethylene glycol-poly-L-lysine (PEG-PLL). These cationic molecules charge-associate with the negatively charged molecule of the delivery vehicle. These embodiments are further described below.

Where the delivery vehicle is a lipid vehicle which is complexed with nucleic acid molecules, such as a plasmid, comprising a transgene, to transfect a target cell, the delivery vehicle-binding portion is an anionic molecule that can bind to positively charged molecules of the lipid portion of the lipid vehicle. The lipid portion may be chemically modified with an amine group which provides the positive charge for binding to the anionic molecule of the bifunctional complex.

Similarly, where the delivery vehicle is a poly-lysine vehicle or a synthetic polyamino polymer vehicle, the bifunctional complex may be bound via a charged molecule in a similar maimer described above for lipid vehicles.

Cell surface molecules which can be targeted by the cell surface molecule binding portion include, e.g., MHC molecules (both class 1 and class 2) especially $\beta_2$ microglobulin, integrins, transferrin receptors, antigens on the surface of certain cells, e.g. AF20 carcinoma cell antigen, molecules which can bind peptides, folate receptors, fibroblast growth factor receptors, epidermal growth factor receptors, erythrocyte growth factor receptors, c-kit receptor, vascular endothelial growth factor receptor, endogenous receptors and co-receptors of adenoviruses, polymeric immunoglobulin receptors, erythropoietin receptors, purinoceptors, cell surface enzymes, etc. The cell surface molecule to be targeted preferably comprises either ubiquitous molecules, such as MHC molecules, or cell specific molecules. Examples of cell specific molecules include for example proteins present in cancerous cells, such as endoglin, a 180 kilodalton (KDa) a homodimer which functions in binding TGF-$\beta$1 and TGF-$\beta$3 to the TGF-$\beta$ receptor, endosialin, a 165-KDa surface glycoprotein expressed on tumor endothelium, and human osteosarcoma cell surface-associated antigen. Other cell specific molecules include E-selecting, a leukocyte adhesion molecule which is upregulated in endothelial cells associated with breast cancer, fibroblast growth factor receptors and vascular endothelial growth factor receptor (VEGF receptor) and AF20 antigen which is expressed on the cell surface of carcinoma cells especially hepatocarcinoma cells, lung adenocarcinoma cells and colorectal carcinoma cells.

The cell surface molecule-binding portion of the bifunctional complex comprises a molecule, or fragment thereof, that effectively binds to the cell surface molecule at sufficiently low concentrations. Preferably, the cell surface molecule binding portion of the construct not only has an affinity for the cell surface molecule which enables targeting to the cell, but also dissociates from the cell surface molecule after the construct is transported across or through the cell membrane. Preferably, the cell surface molecule-binding portion has a dissociation constant of at least $10^{-8}$ M. In preferred embodiments, the cell surface molecule-binding portion has a dissociation constant of at least $10^{-9}$ M. Different applications of the constructs of the present invention will require different dissociation constants, e.g., applications for different tissues will require different degrees of dissociation. The appropriate degree of dissociation, i.e., strength of binding, can be determined by one of skill in the art by routine experimentation.

Examples of useful cell surface molecule binding portions comprise, inter alia, a peptide, ligand, antibody, small molecule, etc., having specific affinity for the cell surface molecule on the target cell. As described above, preferred targeted cell surface molecules include the MHC 1 molecules, the AF20 antigen, as well as molecules that have affinity for peptides selected by phage biopanning techniques, negatively charged cell membrane molecules, folate receptors, fibroblast growth factor receptors, epidermal growth factor receptors, erythrocyte growth factor receptors, c-kit receptor, endogenous receptors and co-receptors of adenoviruses, polymeric immunoglobulin receptors, erythropoietin receptors, purinoceptors. Thus, the present invention will be further described in relation to these molecules. However, the invention is not to be construed to be limited to these molecules. In one preferred embodiment, the cell surface molecule binding portion comprises an antibody, or fragment thereof, having specific affinity for the cell surface molecule. It is preferred that the cell surface molecule-binding portion comprises an antibody, or a fragment thereof to $\beta_2$-microglobulin. In an especially preferred embodiment, the cell surface molecule-binding portion comprises a Fab fragment of an antibody to $\beta_2$-microglobulin.

In other embodiments of the bifunctional complex, the cell surface molecule binding portion comprises an antibody, or fragment thereof, to an a chain of the MHC molecule. As discussed above, the polymorphic nature of the MHC molecule results in different haplotypes throughout the population. Because the majority of humans are HLA-A (40%) as compared to HLA-B and HLA-C, in these embodiments, it is preferred that the MHC binding portion comprises antibodies, or antibody fragments, to the MHC haplotype coitesponding to HLA-A.

Alternatively, constructs of the present invention having cell surface molecule binding portions directed to different types of molecules, e.g., different MHC class I molecules, or multiple cell surface antigens such as AF20 antigen can be mixed in a cocktail to selectively target multiple loci on the cells of interest. The use of a cocktail of delivery vehicle constructs enables the targeting of a variety of receptors at one time. For example, a cocktail of antibodies to non-conserved regions of the various haplotypes of MHC I molecules, and/or AF20 antigen can be used to target multiple loci. Such "cocktails" can be administered together or separately.

As described above, the delivery vehicle constructs can be designed to target molecules specific to particular cell types. For example, a rapidly internalized 180 KDa homodimeric glycoprotein (AF20) has been found to be strongly expressed on the surface of human hepato-cellular carcinoma (HCC) cell lines, as well as other cancer cells such as lung adenocarcinoma and colorectal carcinoma cells. Moradpour, D., et al., "Specific Targeting of Human Hepatocellular Carcinoma Cells by Immunoliposomes In Vitro", *Hepatology*, Vol. 22, No. 5, p. 1527–1537. In another embodiment of the present invention, the cell surface molecule binding portion comprises antibody AF-20 which binds this glycoprotein expressed on the surface of human hepatocellular carcinoma (HCC) cell lines. Other cell types, as known in the art, can be targeted as needed for a particular application.

Additionally, constructs of the present invention have cell surface molecule binding portions selected by phage bio-panning techniques. See, e.g. Smith, G. P. and Scott, J. K., 1993, *Methods in Enzymol.* 217:228–257. These selection methods can isolate peptides with an avidity for a cell type of interest. The use of a selection process enables the targeting to any cell of interest. For example, the cell of interest may be used during the selection process to ensure for the selection of peptides with an affinity for the cell of interest and not for other cells. Peptides selected by biopanning can be used to direct a delivery vehicle (e.g. a virus or lipid vehicle which is used with nucleic acid molecules, such as a plasmid, comprising a transgene) to the target cell.

Also within the scope of the invention are cell surface molecule binding portions comprising charged peptides which may have an affinity for oppositely charged molecules on the cell surface. For example, but not by way of limitation, positively charged peptides may have affinity for the negatively charged nature of cellular membranes.

In another embodiment of the present invention, the cell surface molecule-binding portion comprises a molecule or a fragment thereof that binds to the folate receptor. In an especially preferred embodiment, the cell surface molecule-binding portion comprises folate or a Fab fragment of the MOV19 folate receptor antibody, or any other antibody that binds the folate receptor.

In yet another embodiment of the present invention, the cell surface molecule-binding portion comprises a molecule or a fragment thereof that binds to the transferrin receptor. In an especially preferred embodiment, the cell surface molecule-binding portion comprises transferrin or a Fab fragment HB21 of the transferrin receptor antibody or any other antibody that binds the transferrin receptor.

In a further embodiment of the present invention, the cell surface molecule-binding portion comprises a molecule or a fragment thereof that binds to the fibroblast growth factor receptor. In an especially preferred embodiment, the cell surface molecule-binding portion comprises fibroblast growth factor or a Fab fragment of the fibroblast growth factor receptor antibody.

In still a further embodiment of the present invention, the cell surface molecule-binding portion comprises a molecule or a fragment thereof that binds to the epidermal growth factor receptor. In an especially preferred embodiment, the cell surface molecule-binding portion comprises epidermal growth factor or a Fab fragment of the epidermal growth factor receptor antibody.

In certain other embodiments of the present invention, the cell surface molecule-binding portion comprises a molecule or a fragment thereof that binds to the c-kit receptor. In an especially preferred embodiment, the cell surface molecule-binding portion comprises c-kit or a Fab fragment of a c-kit receptor antibody.

In still another embodiment of the present invention, the cell surface molecule-binding portion comprises a molecule or a fragment thereof that binds to the erythrocyte growth factor receptor. In an especially preferred embodiment, the cell surface molecule binding portion comprises erythrocyte growth factor or a Fab fragment of the erythrocyte growth factor receptor monoclonal antibody B4G7, or any other antibody that binds the erythrocyte growth factor receptor.

In a further embodiment of the present invention, the cell surface molecule-binding portion comprises a molecule or a fragment thereof that binds to the polymeric immunoglobulin receptor. In an especially preferred embodiment, the cell surface molecule-binding portion comprises a Fab fragment of an antibody to the polymeric immunoglobulin receptor.

In yet a further embodiment of the present invention, the cell surface molecule-binding portion comprises a molecule or a fragment thereof that binds to the erythropoietin receptor. In an especially preferred embodiment, the cell surface molecule-binding portion comprises erythropoietin or Fab fragment of the erythropoietin receptor antibody.

In certain other embodiments of the present invention, the cell surface molecule-binding portion comprises a molecule or a fragment thereof that binds to the purinoceptor. In an especially preferred embodiment, the cell surface molecule binding portion comprises a purine or a purine analog (ATP, UTP, ATP-γ-S, AMP-PNP, INS 365) or a Fab fragment of the purinoceptor antibody.

In a further embodiment of the present invention, the cell surface molecule-binding portion comprises a molecule or a fragment thereof that binds to cell surface enzymes. In an especially preferred embodiment, the cell surface molecule-binding portion comprises a small molecule that binds to a cell surface enzyme.

The delivery vehicle-binding portion and the cell surface molecule-binding portion of the present invention are coupled by a linker to form the bifunctional complex. Preferred linkers do not invoke an immune response and have low toxicity. Moreover, they are not easily degraded, e.g., hydrolyzed prior to delivery to the target cell, but are also capable of being broken down or excreted from the cell, without any harmful effect.

One preferred type of linker comprises chemical linkage. Any chemical linkage as known in the art can be used, provided the chemical modification does not affect the reactivity of the delivery vehicle binding portion and cell surface molecule binding portion of the complex and does not otherwise prevent uptake of the delivery vehicle-bifunctional complex by the target cell. One example of a linker comprises a covalent bond through a maleimide-sulfhydryl linkage. In the preferred embodiment, a sulfhydryl group is introduced to the delivery vehicle-binding portion and a sulfhydryl reactive group is introduced to the cell surface molecule-binding portion. For example, N-succinimidyl S-acelythioacetate (SATA) was used to introduce a sulfhydryl group onto an anti-hexon Fab fragment and sulfosuccinimidyl 4-(N-maleimidomethyl) cyclo hexane-1-carboxylate (sulfo-SMCC) was used to introduce a maleimide group onto an anti-$\beta_2$-microglobulin Fab fragment. The binding portions were incubated together resulting in a crosslinked bifunctional complex, with a stable thioether linkage. This linkage is further described in Example 2 below. Of course, the sulfhydryl group can be introduced into the cell surface molecule binding portion and the sulfhydryl reactive group into the delivery vehicle-binding portion. Other linkages comprise disulfide bonds.

Additional linkers include polymers which may be chemically modified to be used as linkers. Polymers are large non-immunogenic, biologically inert molecules comprising a chain of smaller molecules linked by covalent bonds. Polymers useful in accordance with the present invention are those polymers which, when covalently or noncovalently bound to a delivery vehicle, provide a polymer-modified delivery vehicle that retains detectable levels of infection/transfection efficiency and is substantially non-immunogenic. The polymers preferably have an average molecular weight of from about 200 to about 20,000 daltons, are biocompatible, and may be linear or branched. The polymers may be homopolymers or heteropolymers. Suitable polymers for use in the present invention include polyalkalene compounds such as polyalkalene oxides and glycols. Polyalkalene compounds include polyoxymethylene, polyethylene glycols (PEG) and oxides, and methoxypolyethyleneglycols, and derivatives thereof including for example polymethyl-ethylene glycol, polyhydroxypropylene glycol, polypropylene glycol, polymethyl propylene glycol, and polyhydroxypropylene oxide.

A preferred polymer in accordance with the present invention is PEG, which is a water-soluble polymer having the formula $H(OCH_2CH_2)_nOH$, wherein n is the number of repeating units and determines the average molecular weight. PEGs having average molecular weights of from 200 to 20,000 daltons are commercially available. In accordance with the present invention, PEG having an average molecular weight of from 200 ($PEG_{200}$) to 20,000 ($PEG_{20,000}$) may be used to prepare delivery vehicles modified by PEG. In a preferred embodiment, the PEG has an a average molecular weight of from about 2000 to about 12,000. In a more preferred embodiment, the PEG has an average molecular weight of about 5000. In an especially preferred embodiment, the PEG molecule is a bifunctional PEG molecule comprising an amine reactive moiety and a sulfhydryl reactive moiety.

Other chemical compounds that can be used to couple the delivery vehicle binding portion and the cell surface molecule-binding portion to form the bifunctional complex comprise heterofunctional molecules that have both amine reactive and sulfhydryl-reactive groups. Examples of such heterofunctional molecules include, for example, N-succinimidyl 3-(2-pyridyldithio) propionate (SPDP), succinimidyloxycarbonyl-α-methyl-(α-2-pyridyldithio) toluene (SMPT), m-maleimidobenzoyl-N-hydroxysuccinimide ester (MBS), N-succinimidyl (4 iodoacetyl)aminobenzoate (SIAB), succinimidyl-4-(p-maleimidophenyl)butyrate (SMPB), N-(γ-maleimidobutyryloxy)succinimide ester (GMBS), succinimidyl-6-((iodoacetyl)amino)hexonate) (SIAX), succininmidyl-4(((iodoacetyl)amino)methyl) (SIAC), and (p-Nitrophenyl iodoacetate)(NPIA). These molecules may also contain sulfo groups, which will increase the solubility of these molecules in water.

Examples include: sulfo-SPDP, sulfo-SMPT, sulfo-SIAB, sulfo-SMPB and sulfo-GMBS.

When using N-succinimidyl-3-(2-pyridyldithio) propionate (SPDP), the activated N-hydroxysuccinimidyl (NHS) ester end of SPDP reacts with amine groups in proteins, e.g., the cell surface molecule binding portion of the complex, to form an amide linkage. The 2-pyridyldithiol group at the other end reacts with sulfhydryl groups on the other binding portion, e.g., on the delivery vehicle-binding portion, to form a disulfide linkage. The binding can be reversed in alternative embodiments. That is, the activated NHS ester end of SPDP reacts with the delivery vehicle-binding portion and the 2-pyridyldithiol group at the other end reacts with a sulfhydryl group on the cell surface molecule-binding portion.

When using succinimidyloxycarbonyl-a-methyl-(2pyridyldithio) toluene (SMPT), the amine reactive NHS ester at one end reacts with a binding portion of the complex, e.g., cell surface molecule binding portion, and with the delivery vehicle binding portion via a sulfhydryl-reactive pyridyldisulfide group. The delivery vehicle-binding portion has a sulfhydryl group. Again the positioning of the reactive groups can be reversed, as described above.

When using m-maleimidobenzoyl-N-hydroxysuccinimide ester (MBS), the amine reactive NHS ester at one end reacts with amine groups in proteins, e.g., the cell surface molecule binding portion of the complex, to form an amide linkage, and at the other end is a sulfhydryl reactive group. The delivery vehicle-binding portion has a sulfhydryl group. The binding can be reversed, as described above.

When using N-succinimidyl (4-iodoacetyl) aminobenzoate (SIAB), the NHS ester of SIAB couples to primary amines on the cell surface molecule binding portion and iodoacetyl group at the other end can couple to a sulfhydryl residue in the delivery vehicle binding portion. The positioning of the reactive groups can be reversed, as described above.

When using succinimidyl-4-(p-maleimidophenyl) butyrate (SMPB), having an amine reactive NHS ester on one end to bind to the cell surface molecule binding portion and a sulfhydryl-reactive maleimide group on the other end, the delivery vehicle binding portion contains a sulfhydryl group. The positioning of the reactive groups can be revered as described above.

When using N-(γ-maleimidobutyryloxy)-succinimide ester (GMBS), a heterobifunctional crosslinker that contains an NHS ester on one end to bind to the cell surface molecule binding portion and a sulffiydryl-reactive maleimide group on the other end, the delivery vehicle binding portion contains a sulfhydryl group. The positioning of the reactive groups can be reversed as described above.

When using succinimidyl 6-((iodoacetyl)amino) hexonate) (SIAX), which contains an NHS ester on one end to bind to the cell surface molecule binding portion and an iodoacetyl group which can react with sulfhydryls on the other end, the delivery vehicle binding portion contains a sulfhydryl group. The positioning of the reactive groups can be reversed as described above.

When using succinimidyl 4(((iodoacetyl)amino)methyl) (SIAC), which has a cyclohexane-1-carboxylate NHS ester on one end of the molecule which can react with amines of the cell surface molecule binding portion, and an iodoacetyl group on the other end which can couple to sulfhydryl groups, the delivery vehicle binding portion contains a sulfhydryl group. The positioning of the reactive groups can be reversed as described above.

When using (p-nitrophenyl iodoacetate) (NPIA), which has an activated carboxylic acid group with a p-nitrophenyl ester, the p-nitrophenyl ester couples to amine containing proteins of the cell surface molecule binding portion. The other end can react with sulfhydryl groups to give thioether bonds. The delivery vehicle-binding portion contains a sulfhydryl group. The positioning of the reactive groups can be reversed as described above.

In the embodiments described above, the sulfhydryl group is added to either the delivery vehicle binding portion or the cell surface molecule binding portion by methods known in the art, such as by using SATA (N-Succinimidyl S-Acetythioacetyl).

Other heterofunctional reagents for use in chemically linking the delivery vehicle binding portion and the cell surface molecule binding portion such as the MHC binding portion include both carbonyl-reactive and sulfhydryl reactive groups. These reagents are especially useful for conjugating carbohydrate-containing molecules such as glycoproteins to sulfhydryl containing molecules. These chemical linkers are useful for linking delivery vehicle binding portions comprising antibodies other than Fab fragments, e.g., intact antibodies. In intact antibodies, the Fc portion is glycosylated. A preferred carbonyl reactive functional group on these linkers is a hydrazide group that can form hydrazone bonds with aldehydes on sugars. The preferred sulfhydryl reactive functional group on the linkers comprises either a pyridal disulfate group, a disulfide group or a maleimide group. These groups react with a sulfhydryl group on the receptor-binding portion. Examples include 4-(4-N-maleimidophenyl) butyric acid hydrazide (MPBH), 4-(N-maleimidomethyl)cyclohexane-1-carboxyl-hydrazide ($M_2C_2H$ and 3-2(2-pyridyldithio) proprionyl hydrazide (PDPH). As discussed above, the order of the linking with the delivery vehicle binding portion and the cell surface molecule-binding portion can be reversed.

Other useful heterofunctional reagents have an NHS ester on one end and a photoreactive aryl azide group on the other, such as N-hydroxysuccinimidyl-4-azidosalicylic acid (NHS-ASA). Other similar linkers include SANPAH and sulfo-SANPAH (N-succininmidyl-6-(4azido-2'-nitrophenylamino)hexanoate). These linkers contain an NHS ester and a photoreactive phenylazide group. Other similar linkers include sulfosuccinimidyl-2-(m-azido-o-nitrobenzamido)-ethyl-1,3'-dithioproprionate (SAND), N-Succinimidyl-4(4-Azidophenyl) 1,3'dithiopropionate (SADP) and sulfo-SADP. SADP is a photoreactive heterobifunctional cross-linker that is cleavable by treatment with a disulfide reducing agent. The cross-linker contains an amine reactive NHS ester and a photoactivatable phenylazide group. SADP is first used to modify a protein (e.g., antihexon-Fab fragment) via its amine groups through the reactive NHS ester end of the cross-linker. This leads to the formation of a nucleophile-reactive dehydroazepine intermediate able to covalently couple with further amine containing compounds.

Still other useful heterobifunctional reagents comprise molecules containing sulfhydryl-reactive and photoreactive linkers, e.g. ASIB, 1-(pAzidosalicylamido)-4-(iodoacetamido)butyrane. This linker contains a sulfhydryl-reactive pyridal disulfide group on one end and a photosensitive phenylazide group on the other. Another example is APDPN-(4-(p-Azidosalicylamido)butyl]-3'-(2'-pyridyldithio)propionamide.

Another preferred linker comprises a polymer-type of linker, e.g., a heterofunctional PEG. PEG has been shown in clinical trials to be non-immunogenic.

In one embodiment, the PEG molecule is chemically linked to the delivery vehicle binding portion and the cell surface molecule-binding portion. Preferred heterofunctional derivatives of PEG include a heterofunctional PEG with either a NHS ester or a tresyl group on one end and vinylsulfone or maleimide on the other end. Other heterofunctional derivatives of PEG include a heterofunctional PEG having a protected amine on one end and the PEG would be activated on other end, using e.g. (ω-hydroxy-α-amine, ω-hydroxy-α-carbonyl and ω-amino-α-carbonyl molecules. The binding portions of the complex can be coupled to the linker as described below.

Also within the scope of the invention are branched heterofunctional PEG molecules. Preferred branched heterofunctional derivatives of PEG include a heterofunctional PEG with a tresyl group on one end and multiple maleimide groups on the other end (see FIG. 18).

In a preferred embodiment of the present invention, the delivery vehicle binding portion comprises a Fab fragment of an antibody to the delivery vehicle and the cell surface molecule binding portion comprises a Fab fragment to the cell surface molecule of interest. In one especially preferred embodiment, an adenovirus is bound to a bifunctional complex that comprises a Fab fragment of an anti-hexon antibody linked to a Fab fragment of an anti-$\beta_2$-microglobulin antibody. Preferably, the two Fab fragments are chemically linked together. FIG. 1 is a schematic diagram showing this bifunctional Fab molecule and the schematic steps to its manufacture.

In another preferred embodiment of the present invention, the bifunctional molecule comprises a bifunctional PEG molecule. Preferred heterofunctional derivatives of PEG include a heterofunctional PEG with a tresyl group on one end and a maleimide on the other end. In especially preferred embodiments of the invention, adenovirus is linked to the bifunctional PEG via the tresyl group and the AF20 antibody is linked to the bifunctional PEG molecule via the maleimide group to form the delivery vehicle construct. This is further described below in Example 11.

Figure 18:
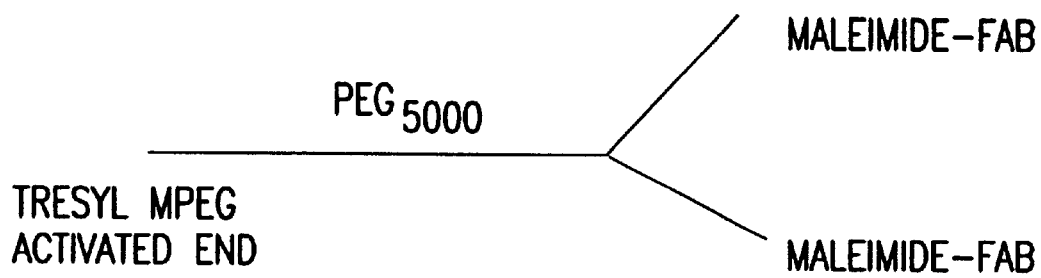
FIG. 18 is a diagrammatic representation of a branched bifunctional PEG molecule.

In certain embodiments of the bifunctional complexes of the present invention, at least one of the binding portion comprises an antibody or a fragment thereof and where the bifunctional molecule is branched, the branched binding portion may comprise multiple antibodies or fragments thereof (FIG. 18). Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragments; and the Fab fragments which can be generated by treating the antibody molecule with papain and a reducing agent. As described above and in Example 2 below, N-succinimidyl S-acelythioacetate (SATA) was used to introduce a sulfhydryl group onto an anti-hexon Fab fragment to create a Fab which is capable of being linked to a sulfhydryl reactive group e.g., a maleimide group, on another binding portion according to the methods described herein. Because Fab' fragments already have a free sulfhydryl group, they can be linked to a sulfhydryl-reactive group without any prior chemical treatment.

Generally, a preferred method for generating antibody fragments comprises digestion of the selected antibody with papain and cysteine to generate IgG, Fab and Fc. A solution of the components is then loaded on a column containing Protein A. IgG and Fc bind the column and Fab is present in the effluent.

Any known chemical linkage of the two Fab fragments can be used in the present invention, provided that the chemical modification does not affect the reactivity of the delivery vehicle and cell surface molecule binding portions of the complex and does not otherwise prevent uptake of the delivery vehicle-bifunctional complex by the target cell, e.g., a thioether linkage. In a preferred embodiment, a sulfhydryl group is introduced onto a Fab fragment, e.g., anti-hexon Fab, and a sulfhydryl reactive group, e.g., a maleimide group, is introduced onto another Fab fragment, e.g., anti-$\beta_2$-microglobulin. The two Fab components are incubated together resulting in a crosslinked bifunctional Fab complex, with a stable thioether linkage. This linkage is further described in Example 2 below.

In another embodiment of the present invention, which uses a linker comprising an ionic bond, the bifunctional complex comprises a cationic molecule, e.g., a poly-L-lysine molecule linked to the cell surface molecule-binding portion by PEG. In this embodiment, the delivery vehicle-binding portion comprises the poly-L-lysine. The positively charged poly-L-lysine charge-associates with the overall negative charge on the cell membrane of the virus. In one example, PEG 5000 was coupled to PLL (poly-L-lysine 55K or 110K) using the N-hydroxysuccinimidyl (NHS) derivative of PEG propionic acid (SPA-mPEG) (Shearwater Polymers Huntsville, Ala.). The other end of the PEG is covalently bound to the cell surface molecule-binding portion of the complex, e.g., via a vinylsulfone or maleimide group. Other cationic molecules, as discussed above, are useful as linkers which link via an ionic interaction.

Another approach to increasing the binding ability of a delivery vehicles, e.g., adenovirus or retrovirus, to a broad range of cell types is to target the delivery vehicle constructs to cell surface integrins, which are commonly found on various different cell types. In such embodiments of the present invention, the cell surface molecule-binding portion of the delivery vehicle construct preferably comprises an RGD-containing peptide. The RGD-containing peptide is linked to a delivery vehicle-binding portion consistent with the present invention. For example, RGD containing peptides, such as, but not limited to those in Table 1 below, were synthesized with cysteine residues containing a free reactive sulfhydryl group, which facilitates coupling to maleimide groups, as described above and as shown in FIG. 1. Linear or cyclic RGD-containing peptides are useful. Cyclization may occur via amide bond formation between lysine and aspartic acid residues in the molecule. Alternatively, these cyclic peptides can be made by omitting the lysine and aspartic acid amino acids and Cyclization occurs via disulfide bonds between cysteine residues. Peptides cyclized using a disulfide bond can be synthesized with a poly-lysine tail (e.g. a poly-lysine tail consisting of 7–12 lysine residues) which allows the RGD peptide to be coupled to a Fab fragment via an amine reactive cross linker such as SPDP or SADP, as described above. Additionally, sulfhydryls can be introduced in the poly-lysine tail using SATA, as described above, to link to maleimide labeled virus.

TABLE 1

A. Cyclic RGD Molecules

| | |
|---|---|
| 1) Cyc-Ac-KGGCRGDMFGCGDGC-amide | (SEQ ID NO:1) |
| 2) Cyc-Ac-KATIRRGDALADGGAC-amide | (SEQ ID NO:2) |
| 3) Cyc-Ac-KPARGDSSVDGC-amide | (SEQ ID NO:3) |
| 4) Cyc-Ac-KGRARGDNPDGDGC-amide | (SEQ ID NO:4) |
| 5) Cyc-Ac-KACRGDGWCGDGC-amide | (SEQ ID NO:5) |
| 6) Cyc-Ac-KACPSRLDSPCGDGC-amide | (SEQ ID NO:6) |
| 7) Cyc-Ac-KACDCRGDCFCGDGC-amide | (SEQ ID NO:7) |
| 8) Cyc-Ac-KCDCRGDCFGDGC-amide | (SEQ ID NO:8) |

B. Linear RGD sequences

| | |
|---|---|
| 9) GRGDSPC | (SEQ ID NO:9) |
| 10) RGDFC | (SEQ ID NO:10) |
| 11) CRGDCLC | (SEQ ID NO:11) |
| 12) CDCRGDCFC | (SEQ ID NO:12) |
| 13) CNORCVSGCAGRC | (SEQ ID NO:13) |
| 14) CNGRC | (SEQ ID NO:14) |

The sequence shown in Table 1 as peptide (2), SEQ ID NO:2 is the RGD sequence which is found in a protein secreted from *Bordetella pertussis* called pertactin. This sequence in pertactin facilitates the binding of *Bordetella pertussis* to lung epithelial cells via integrins. Leninger et al., 1991, *Proc. Natl. Acad. Sci.*, 88:345–349. Similarly the sequence in peptide (4), SEQ ID NO:4 contains the RGD sequence derived from disintegrin. Disintegrins are a family of low molecular weight peptides widely distributed in viper venoms which inhibit the adhesive functions of a variety of integrins on cell surfaces. Most disintegrins contain the RGD recognition sequence which appears to play a central role in their interaction with numerous integrins. Scarborough et al., 1993, *J. Biol. Chem.*, 268:108–2065.

A delivery vehicle binding portion, such as an anti-hexon Fab fragment, containing a maleimide group (prepared as described above and according to Examples 1 and 2 below), was coupled to these RGD peptides via the free sulfhydryl group on the C-terminal cysteine residues of the RGD containing molecules. RGD containing peptides cyclized via disulfide bonds with a poly-lysine tail can be cross-linked to the anti-hexon Fab fragment using amide reacting cross-linkers such as SPDP.

Alternatively, the RGD containing peptides are coupled to maleimide groups which are covalently attached to poly-L-lysine (PLL). PLL has been shown to associate with adenovirus and increase its infectivity in a non-specific manner into different cell types (Fasbender, A., et al., 1996, *J. Biol. Chem.* 272: 6479–6489; WO 98/22144 incorporated herein by reference). Coupling RGD peptides of different sequences to PLL before coupling with the delivery vehicle confers specificity to this cationic molecule which will allow for more selective targeting of adenovirus—PLL conjugates.

These delivery vehicle constructs can be used to target cells, which express integrins such as, but not limited to, HT-29 colon carcinoma cells, lymphocytes and monocytes, blood platelets, SMC-90 human lung fibroblast, MG (63) (osteosarcoma cell line), vascular endothelial cells and melanoma cells. See Table 2 below.

TABLE 2

| Cell | Integrins |
|---|---|
| HT-29 colon carcinoma | $\alpha v\text{-}\beta_5$ |
| Lymphocytes/monocytes | $\alpha 4\text{-}\beta_1$ |
| Blood Platelets | $\alpha 11b\text{-}\beta_3$ |
| IMR-90 Human lung fibroblast | $\alpha v\text{-}\beta_3$ |
| MG (63) (Osteosarcoma cell line) | $\alpha v\text{-}\beta_3$ |
| Vascular Endothelial cells | $\alpha v\text{-}\beta_3$ |
| Melanoma cells | $\alpha v\text{-}\beta_3$ |
| Human VCIA-P3-lung carcinoma | $\alpha v\text{-}\beta_5$ |

A further approach to increasing the binding ability of a delivery vehicle to a specific cell type is to target the delivery vehicle to the specific cell type with a peptide that has been selected for its high avidity for the target cell. In such embodiments of the present intention, the cell-surface molecule-binding portion of the delivery vehicle construct preferably comprises a peptide which has been selected for its high avidity of the target cell. For example, high avidity peptides, such as, but not limited to those in Table 3 below, were selected by phage biopanning techniques. As shown in Table 3, four subgroups of displayed peptides were identified based on their homologies. Any technique for such selection known to those in the art may be employed to isolate peptides with high avidity for target cells. In one preferred embodiment of the invention, phage biopanning was employed to select for peptides (Table 3) which have a high avidity for differentiated, ciliated human airway cells. The cell surface molecule-binding portion of the bifunctional complex preferably comprises the high avidity peptides. The high avidity peptides are linked to the bifunctional complex consistent with the present invention as described above for the RGD peptides. This is further described in Example 8 below.

TABLE 3

| | | | |
|---|---|---|---|
| 1) | sss.10 | TTDFYYALRALA | (SEQ ID NO:15) |
| 2) | sss.14 | TTDFYYALRALA | (SEQ ID NO:16) |
| 3) | sss.8 | LPKMASVQRNLA | (SEQ ID NO:17) |
| 4) | sss.9 | HETFYSMIRSLA | (SEQ ID NO:18) |
| 5) | sss.5 | HDTFLYGLQRLV | (SEQ ID NO:19) |
| 6) | sss.9 | HETFYSMIRSLA | |
| 7) | sss.6 | LTFDQTPLTAQI | (SEQ ID NO:20) |
| 8) | sss.7 | ITFNQTVTTSYM | (SEQ ID NO:21) |
| 9) | sss.16 | ETFSDPLAGSSS | (SEQ ID NO:22) |
| 10) | sss.17 | SDQLASPYSHPR | (SEQ ID NO:23) |

Other useful peptides for use as cell-surface molecule binding portions of the present invention include charged peptides. Any charged peptide which may increase the transfection/infection efficiency of a delivery vehicle in a target cell is contemplated by the invention. In one embodiment, the cell-surface molecule binding portion of the invention comprises a positively charged poly-lysine peptide (CGSGSGSGSGSKKKKKKK, P7 (SEQ ID NO:24); and CGSGSGSGSGSKKKKKKKKKKKKKKKKKKKK, P21 (SEQ ID NO:25)). In a particularly preferred embodiment, the cell-surface molecule binding portion comprises SEQ ID NO:25.

Another target molecule on the surface of specific cells is the AF20 antigen which is selectively expressed on the cell surface of carcinoma cells, especially hepatocarcinoma cells, lung adenocarcinoma cells and colorectal carcinoma cells. In certain embodiments of the invention, the cell surface binding portion of the bifunctional complex preferably comprises the AF20 IgG antibody. The antibody is linked to the delivery vehicle portion of the bifunctional complex as described above via a maleimide group consistent with the present invention. For example, antibodies, such as, but not limited to, AF20 IgG antibody are labeled with Traut's reagent (2-iminothiolane hydrochloride) using a 10-fold molar excess. The resulting SH-labeled antibody (AF20-SH) is cross-linked to the tresyl-Ad-PEG-maleimide complex. Delivery vehicles, such as, but not limited to, adenovirus are added to the solution with the antibody and the bifunctional complex and the delivery vehicle construct is then isolated by techniques known to those in the art (e.g. gel filtration chromatography, centrifugation, etc.). This is further described in Example 11 below.

In other preferred embodiments of the invention, a bifunctional antibody may be employed to target the delivery vehicle to the target cell. In particularly preferred embodiments, the bifunctional antibody comprises the AF20 antibody covalently linked to 2Hx-2 (anti-hexon) monoclonal antibody (see Example 10 below). This bifunctional antibody can target a recombinant adenovirus to hepatocarcinoma cells, lung adenocarcinoma cells, and colorectal carcinoma cells.

Still another target molecule on the surface of cells is the transferrin receptor which is expressed at higher levels in the transformed cells. In certain embodiments of the invention, the cell surface molecule binding portion of the delivery vehicle construct comprises a small transferrin receptor binding peptide or a Fab fragment of a transferrin receptor antibody. The small transferrin receptor binding peptide is linked to the delivery vehicle-binding portion of the bifunctional complex consistent with the present invention as discussed above.

Other cell surface target molecules useful for targeting the delivery construct of the present invention include the following. Serpin enzyme complex receptor (SEC-R) found on hepatoma cells which can be targeted using a synthetic peptide ligand (C1315) based in sequence on amino acids 346–374 of human $\alpha_1$-antitrypsin (Ziady et al., 1997, *Am. J. Phys.* 273:G545–G552) as the cell surface molecule binding portion. The C1315 peptide can be synthesized with a cysteine residue with a free sulfhydryl group and linked to the maleimide group of a bifunctional PEG complex (attached to a delivery vehicle) as already described for sss.17 peptide in Example 8 below. For targeting retroviruses the c-Met receptor on hepatocytes may be the cell surface molecule. This binds the hepatocyte growth factor (HGF) (Nguyen et al., 1998, *Hum. Gene. Ther.* 9:2469–2479) which may be used as the cell surface binding portion of the present invention. Additionally, the mannose-6-phosphate receptor cell surface molecule may be targeted using monosaccharide mannose as the cell surface molecule-binding portion.

The cell surface molecule-binding portion of the delivery construct may alternatively comprise basic fibroblast growth factor (bFGF). BFGF may be coupled to the bifunctional complex which in turn is coupled to a delivery vehicle. Such a bFGF-bifunctifonal PEG-delivery vehicle construct may be used to target tumor cells since it is up-regulated in many tumor cell lines and it is therefore a versatile targeting molecule. Other useful tumor cell lines which may be targeted include: BxPC-3 (pancreatic adenocarcinoma), HCT116 (colon carcinoma), K-562 (chronic myelogonous leukemia), KM-12 and KM20L2 (colorectal carcinoma), OVCAR-5 (ovarian carcinoma), Panc-1 (pancreatic epitheloid carcinoma), B16FO (melanoma), and RENCA (renal carcinoma).

Additionally, delivery vehicles may be targeted to cells via the binding of small molecules to cell surface receptors. In certain embodiments of the invention, the small molecule comprises a purine or a purine analog (ATP, UTP, ATP-γ-S, AMP-PNP, INS 365) which has affinity for the purinoceptor, an airway epithelial cell surface receptor. The small molecule may be linked to the delivery vehicle-binding portion by chemically modifying the small molecule with a reactive group (e.g. a sulfhydryl group) which can be attached to a bifunctional complex.

In another embodiments of the invention, the delivery vehicle is associated with the delivery vehicle-binding portion of the bifunctional complex. For example, the surface of the delivery vehicle, e.g. adenovirus, is associated with the anti-hexon Fab fragment using bifunctional linkers such as those listed above, e.g., NHS-PEG-maleimide. The NHS would couple to the virus while the maleimide would react with free sulfhydryl groups on the Fab fragment. The Fab fragment in turn would be coupled to maleimide containing ligands, antibodies or RGD sequences. Other cross-linkers such as SPDP, could also be used. Similarly the PLL could be covalently attached to the adenovirus by introducing maleimides into the PLL which could in turn couple to sulfhydryls introduced onto the surface of the virus. An alternative approach would be to couple the PLL to the surface of the virus with a cross-linker such as SPDP.

The delivery vehicle constructs of the present invention can be made in a number of ways. The preferred method comprises first synthesizing the bifunctional complex and then incubating the complex with the delivery vehicle, e.g., adenovirus. The delivery vehicle/bifunctional complex construct is then introduced into the target cells. In embodiments in which the delivery vehicle/bifunctional complex construct is used in vivo, the construct is administered to an individual, as known in the art, for the delivery of transgenes, e.g. IV, IM, SC, etc.

The constructs of the present invention are useful for introducing selected transgenes into specific target cells. Target cells include any cell type of interest, including bacterial, plant and animal cells. In preferred embodiments, the target cells are mammalian cells, e.g., human, monkey, rabbit, mouse or rat cells.

Figure 5A:
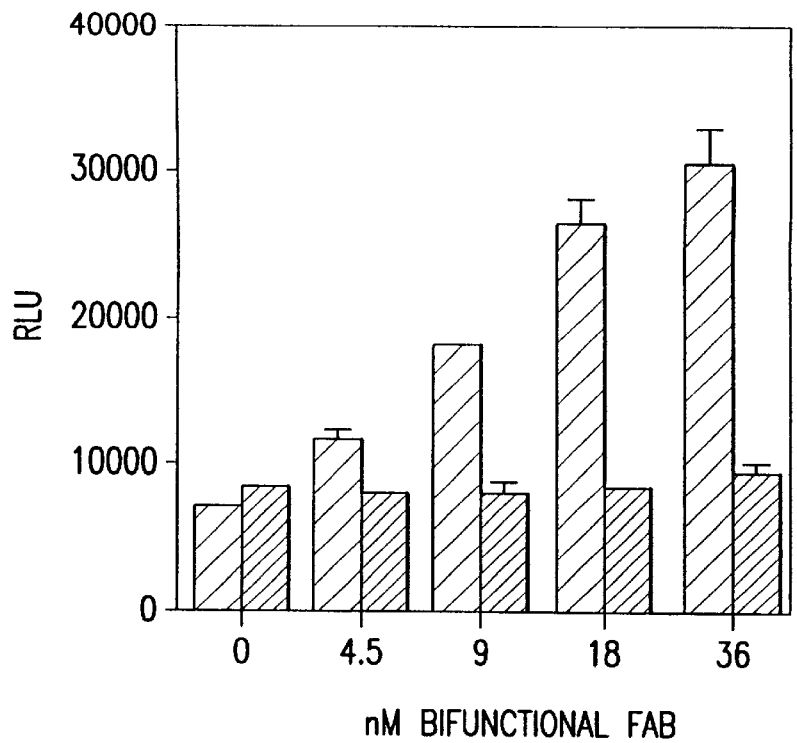
FIGS. 5A–B are graphs showing the increase in the infection of HUVEC cells by adenovirus in the presence of bifunctional Fab conjugates.
Figure 5B:
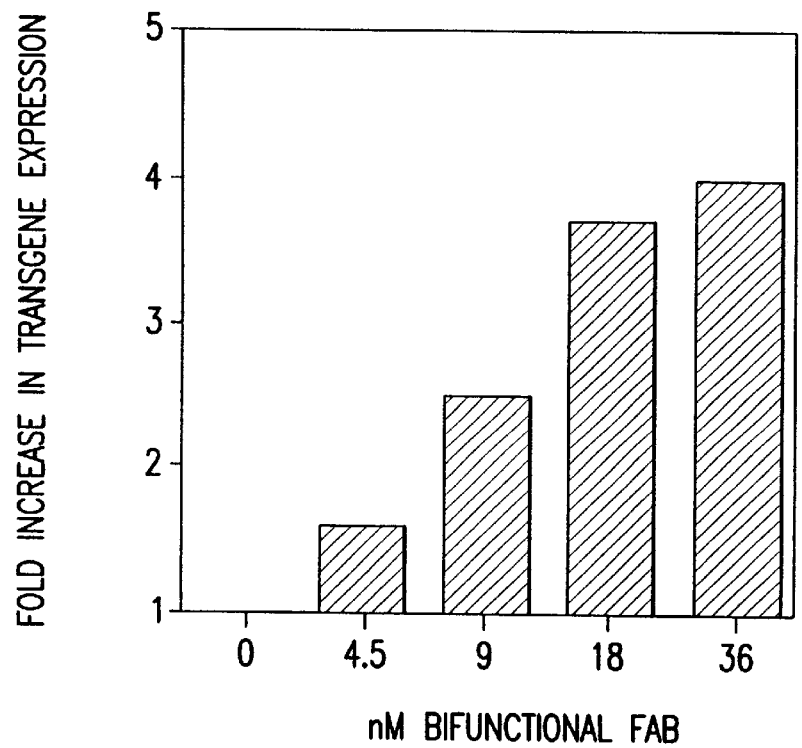

The usefulness of the present invention can be demonstrated, for example, by incubating the delivery vehicle/bifunctional complex construct with target cells, e.g., human umbilical vascular endothelial cells ("HUVEC cells") which are normally refractory to infection by adenovirus. As shown in FIG. 5, HUVEC cells were infected with adenovirus (Ad2/βgal4; Armentano, D. et al., 1997, *J. Virol.* 71:2408–2416) in the presence of increasing amounts of a bifunctional Fab complex. Increasing the amount of bifunctional Fab led to a corresponding increase in infection of HUVEC cells suggesting that the bifunctional complex could mediate adenoviral infectivity in these cells. FIG. 5A compares the transgene (β-galactosidase) expression in HUVEC cells infected with the Ad2-βgal4 vector in the presence of a reactive bifunctional Fab complex (solid bars) with the expression in HUVEC cells infected with Ad2-βgal4 vector in the presence of a non-reactive bifunctional complex (dotted bars). (The reactive bifunctional Fab complex was shown to recognize both hexon and β2-microglobulin in an ELISA format, while the non-reactive complex failed to recognize hexon in the ELISA). There was significant increase in transgene expression (up to 4 fold over expression measured with the Ad2-β gal-4 vector alone) in HUVEC cells infected with vector in the presence of the targeting complex (FIG. 5B). This result suggests that bispecific complexes can be successfully used to target adenovirus to a specific cellular receptor and thereby increase the efficiency of gene transfer.

Similarly, the delivery vehicle constructs of the present invention are useful for transducing human dendritic cells. Human dendritic cells are very effective antigen presentation cells due to a high density of MHC 1 molecules on their cell surface. Thus, these cells have clinical use as antigen presentation cells, in the delivery of nucleic to tumor cells, wherein, expression therein, e.g., may be toxic to cells. However, one of the main disadvantages of these cells, e.g. for use in cancer therapy, is that they are not easily infected by adenovirus, presumably due to a low abundance of the adenovirus fiber receptor on the cell surface. It has been found that use of a bifunctional Fab construct of the present invention which recognizes the $\beta_2$-microglobulin subunit of MHC class I molecules complexed with adenovirus, increased the efficiency of adenoviral infection in these cells. As described in Example 6 below, and FIG. 7, human dendritic cells treated with adenovirus, pretreated with a bifunctional Fab complex show a ten-fold increase in expression of the transgene (green fluorescence protein) compared to cells infected with adenovirus alone.

Additionally, the deliver vehicle constructs of the present invention have been shown to be effective in infecting primary cultures of well-differentiated human airway epithelial cells (see Example 9 below). A specific cell surface receptor for airway epithelial cells is not known and these cells lack the appropriate adenovirus receptors necessary for efficient viral entry via the fiber knob penton base-mediated entry pathways. Thus, targeted nucleic acid delivery to these cells has obstacles although these cells are particularly important in the treatment of cystic fibrosis through the delivery of a nucleic acid molecule encoding for wild-type CFTR. Phage biopanning can lead to the identification and isolation of peptides which have a high avidit for human airway epithelial cells (see FIGS. 7 and 8 and Example 7, 8, and 9 below). NHBE cells used in phage biopanning experiments yielded several peptides with an avidity for human airway epithelial cells. See FIG. 7 and 8. The infection efficiency of well-differentiated airway cells by adenovirus expressing the β-galactosidase gene, the virus having been complexed with PEG and a peptide isolated from phage biopanning, sss.17 (SEQ ID NO:23), was increased fourfold in comparison to infection by an adenovirus that was modified by PEG alone (as measured in the amount of β-galactosidase activity in the cells). See FIG. 10A. Furthermore, infection of HeLa cells is not affected by the presence of the peptide indicating that the peptide is specific for primary cultures of well-differentiated human airway epithelial cells. See FIG. 10B. FIG. 11 demonstrates that increased amounts of peptide can compete for the infection efficiency in well-differentiated human epithelial cells. These results also suggested that the increased infectivity of the modified viral complex is mediated by the coupled peptide. Moreover, when cystic fibrosis epithelial cells, which have defective chloride channels, were infected with an adenovirus comprising a transgene encoding for CFTR, the chloride channel defect was corrected. See FIG. 16.

In vivo applications for the use of the sss.17 peptide to enhance the infection efficiency of delivery vehicles comprising a transgene encoding for CFTR may be assessed in mouse airway epithelia cells. See Scaria et al., 1998, *J. Virol.* 72:7302–7309. Scaria et al. describe methods for the assessment of functional expression of CFTR in nasal epithelia of CFTR mice. Such a model system could be used with the delivery vehicle constructs of the present invention to determine the in vivo advantages in treating disease.

Figure 12A:
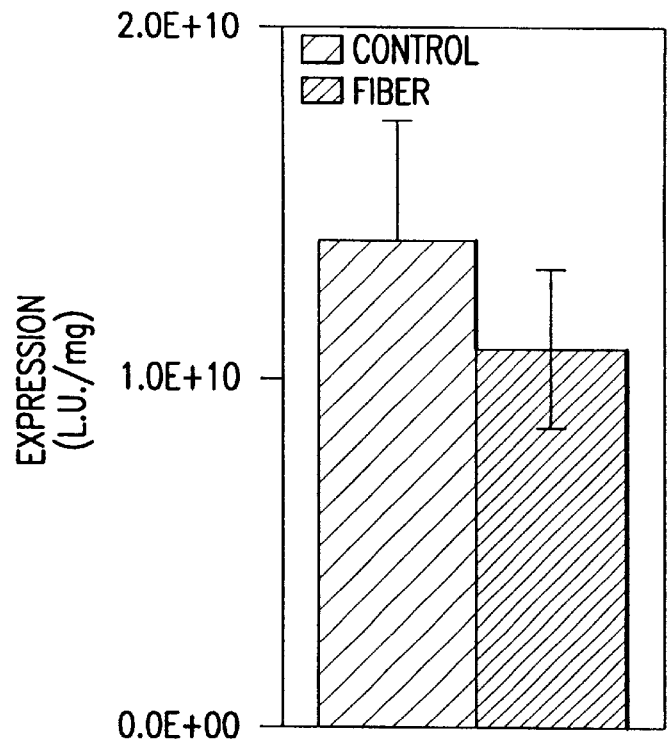
FIGS. 12A–B are graphs of the competition of PEG-peptide modified adenovirus infection efficiency by excess fiber knob measured by the ability of the infected cell to express β-galactosidase. (A) Primary cultures of well-differentiated human airway epithelial cells. (B) HeLa cells.
Figure 12B:
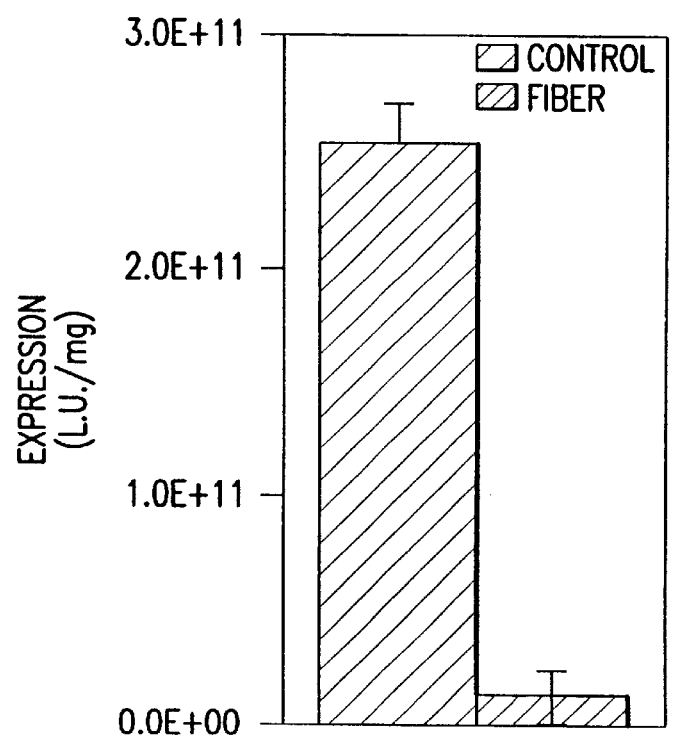

Normally, the efficient adenoviral entry into target cells requires viral attachment to the Coxsackie-adenovirus receptor (CAR) at the cell surface and internalization via integrin receptor-mediated endocytosis. Though it has been shown that well differentiated human airway cells lack CAR for efficient viral entry via the fiber knob/penton base-mediated pathways, it is believed that sss.17, is mediating the infection efficiency. In order to further confirm that sss.17 mediated the infection efficiency, and did not simply provide increased residence time at the cell surface and thus promoting viral entry via a low abundant fiber knob and penton base receptors, the infection efficiency of Ad2/PEG/sss.17 was tested in the presence of excess fiber knob which should compete for receptor mediated infection dependent on fiber knob. Well-differentiated human airway epithelial cells on ALIs were infected in the presence of absence of competing fiber knob protein. Cells grown on ALIs differentiate in a pseudo-stratified layer, with a histology resembling in vivo airway epithelia. Gray, T. E. et al., 1996, *Am. J. Respir. Cell Mol. Biol.* 14:104–112; Yamaya, M. et al., 1992, *Am. J. Physiol.* 262:L713–724. FIG. 12A shows that infection of well-differentiated human airway epithelial cells by Ad2/PEG/sss.17 could not be competed by excess fiber knob. This supports that entry of Ad2/PEG/sss.17 occurs via a novel pathway of viral entry mediated by the coupled peptide. In contrast, infection of HeLa cells (which have CAR on their cell surface) by Ad2/PEG/sss.17 could be competed by excess fiber knob (FIG. 12B).

Figure 15:
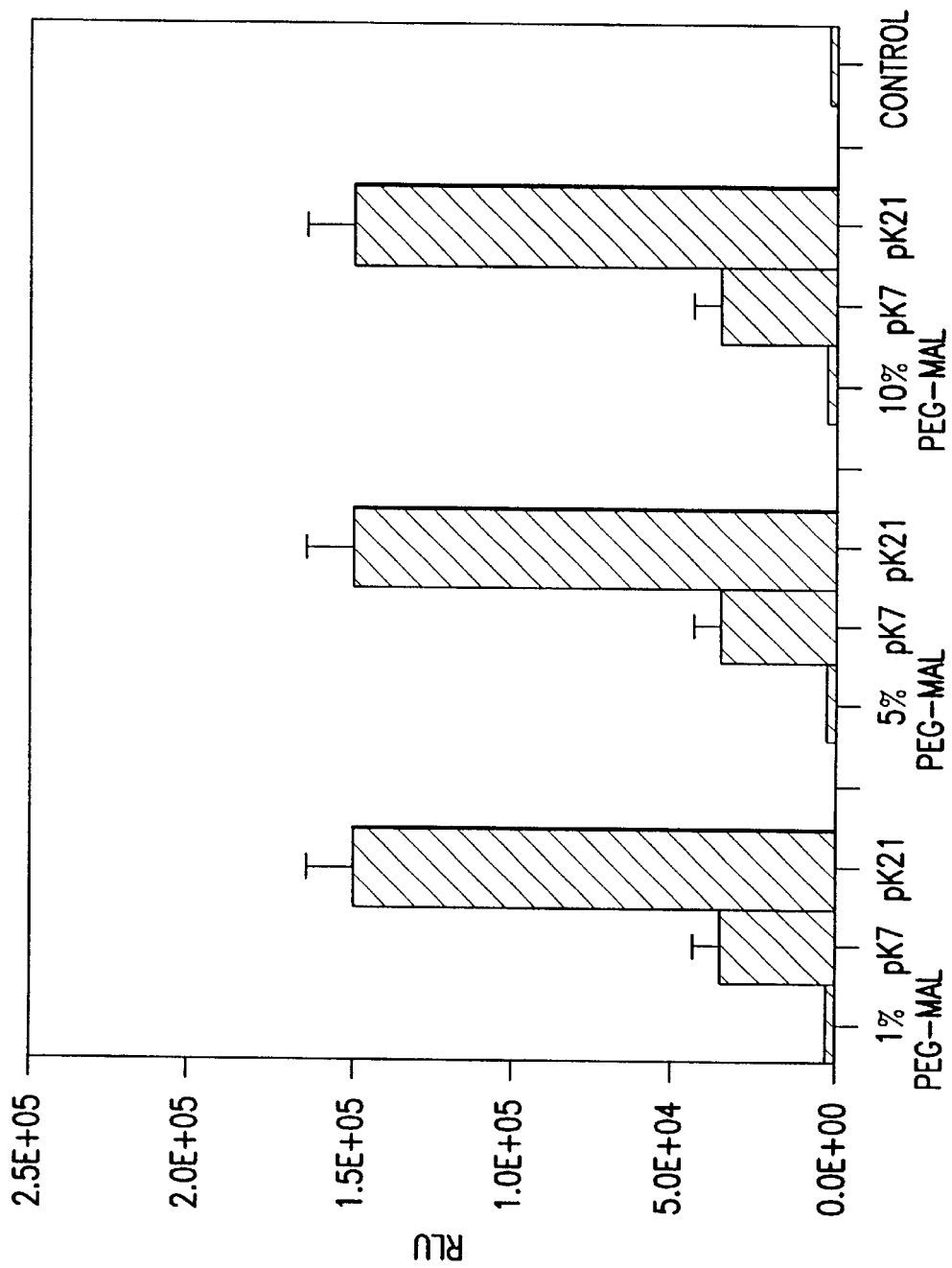
FIG. 15 is a graph showing the infection efficiency of bifunctional PEG-poly-lysine peptide modified adenoviruses. Infection efficiency was measured by the ability of NIH 3T3 cells to express the gene product (β-galactosidase).

Other useful cell-surface molecule binding portions of the invention comprise poly-lysine peptides (p7 (SEQ ID NO:24) and p21 (SEQ ID NO:25)). FIG. 15 shows that a peptide having SEQ ID NO:24, and particularly a peptide having SEQ ID NO:25 can improve the infection efficiency of adenovirus in NIH 3T3 cells by at least 2 logs.

Similarly, the delivery vehicle constructs of the present invention are useful for infecting/transfecting human carcinoma cells. Human carcinoma cells (especially hepatocarcinoma cells, lung adenocarcinoma and colorectal carcinoma cells) have a high density of AF20 antigen molecules on their cell surface. Therefore, a targeted delivery system via the AF20 antigen is a useful tool in the delivery of transgenes to these cells. The bifunctional complex of the present invention can be utilized to create a delivery vehicle associated with the bifunctional complex which links the delivery vehicle to the AF20 antibody (see Example 11 below). FIG. 13 shows that FOCUS cells were infected with adenovirus linked to the AF20 antibody via a bifunctional PEG molecule. These data show that adenovirus treated with MPEG can still infect cells. But, when the adenovirus is modified with 10% TMPEG, its infection efficiency is substantially reduced. When adenovirus is then modified with 10% TMPEG-AF20, the infection efficiency is restored. To assess whether the infection efficiency is mediated by the AF20 antibody, FOCUS cells were incubated with the either the MPEG-modified adenovirus or 10% TMPEG-AF20-modified adenovirus in the presence of increasing amounts of fiber knob protein (FIG. 13B). Fiber knob was able to compete for the binding of the MPEG-modified adenovirus, but had no significant effect on the 10% TMPEG-AF20-modified adenovirus, indicating that infection by 10% TMPEG-AF20-modified adenovirus is mediated via a pathway dependent upon the AF20 antibody.

Additionally, the use of a bifunctional antibody construct comprising an AF20 antibody linked to an antihexon monoclonal antibody (2Hx-2), can target to and increase infection efficiency of recombinant adenovirus in carcinoma cells. As described in Example 10 below, and FIG. 14, hepatocellular carcinoma cells (FOCUS cells) treated with adenovirus which had been pretreated with the AF20/2Hx-2 bifunctional antibody complex, exhibited an increase in expression of the β-galactosidase gene compared to cells infected with adenovirus in the absence of the bifunctional antibody complex. Moreover, the infection efficiency was not competed by the addition of excess fiber knob protein.

Targeting moieties (or cell surface binding molecules of the invention) may also be attached to adenoviral vectors using the carbohydrate on fiber via the use of the heterobifunctional reagent 4-(4-N-maleimidephenyl) butyric acid hydrazide (MPBH). MPBH combines a nucleophilic hydrazide with an electrophilic maleimide. The carbohydrate moiety on fiber contains O-linked N-acetylglucosamine which can be oxidized and coupled to targeting moieties. Such a modified adenovirus delivery vehicle is useful to deliver nucleic acids to a target cell.

The constructs of the present invention thus may be used to target of specific tissues, organs, or tumors for transgene delivery to achieve a phenotypic alteration in the target cells. For example, such phenotypic alteration in the target cells and tissue could be the presence of a functional chloride ion channel in airway epithelial cells from a cystic fibrosis patient to whom a CFTR gene has been delivered. Other such phenotypic changes include cell death in the case of a tumor cell targeted with a suicide gene encoding a toxic molecule. Other examples are known by those skilled in the art. Lung epithelium in Cystic Fibrosis patients and hepatocarcinoma cells can be specifically targeted. Preferred adenovirus constructs also are useful for targeting transgenes to cardiovascular tissues, specific tumors, or cells and organs in which lipids and/or carbohydrates are stored in lysosomes deficient in lysosomal enzymes.

It is known that gamma interferon increases expression of MHC molecules on the surface of the cells. Bikoff, EX, et al., 1991, *Nature*, 354:235–238. It has been found that the presence of gamma interferon increases the in vitro uptake of the adenovirus. One embodiment of this invention further comprises the use of gamma interferon to enhance adenovirus/bifunctional complex uptake. In this embodiment, the effective amount of gamma interferon can range from about $2.5 \times 10^3$ units per kg to about $2.5 \times 10^8$ units per kg. Preferably, the gamma interferon is present in the amount of from about $2.5 \times 10^4$ units per kg to about $2.5 \times 10^6$ units per kg. The dosages are administered over an appropriate time period, e.g., 3 weeks, depending on the dosage and other factors. The gamma interferon should be present in less than about $2.5 \times 10^8$ units, in order to prevent cell death. A preferred dose level comprises $1 \times 10^5$ units/kg daily.

The infection/transfection complexes may be formulated into suitable compositions for administration to a subject in need of the delivery of the transgene. Such compositions comprise constructs, which typically are made as described previously by combining the delivery vehicle, e.g., an adenovirus, with the bifunctional complex and admixing the same with a suitable carrier.

Such carriers include any suitable physiological solutions or dispersant or the like. The physiologic solutions include any acceptable solution or dispersion media, such as saline, or buffered saline. The carrier may also include antibacterial and antifungal agents, isotonic and absorption delaying agents, and the like. Except insofar as any conventional media, carrier or agent is incompatible with the active ingredient, its use in the compositions is contemplated.

Routes of administration for the compositions containing the delivery vehicle constructs of the present invention include any conventional and physiologically acceptable routes, such as, for example, intranasal, inhalation, aerosol inhalation, intravenous, intramuscular, subcutaneous, intradermal, oral and other parenteral routes of administration.

The invention is further directed to methods for using the compositions of the invention for in vivo or ex vivo applications in which it is desirable to deliver one or more transgenes into cells to achieve a particular phenotypic effect. In vivo applications involve, e.g., the direct administration of the delivery vehicle construct of the present invention formulated as a composition to the cells of an individual. Ex vivo applications involve, e.g., the transfer of the delivery vehicle construct directly to autologous cells which are maintained in vitro, followed by re-administration of the infected/transfected cells to a recipient.

Dosage of the delivery vehicle construct of the present invention to be administered to an individual in order to achieve a phenotypic effect is determined with reference to various parameters, including the condition being targeted, the age, weight and clinical status of the individual, and the particular physiological condition requiring phenotypic alteration. Dosage also depends upon the location of the cells to be targeted. For example, target cells of the lung may require different dosages than administration into the blood stream of a patient.

The dosage is preferably chosen so that administration causes an effective result, as measured by molecular assays or phenotypic alteration. For example, determination of the level of expression of the transgene product of interest, as well as persistence of such expression over time can be performed by molecular assays including the measurement of the protein of interest produced, as detected by Western blot, immunoprecipitation, immunocytochemistry, or other techniques known to those skilled in the art. Relevant studies that can be used to assess phenotypic alteration from delivery of the trausgene, e.g., CFTR, include determining the presence of a functional chloride channel in cells harboring the CFTR transgene, as well as PFT assessment of lung function and radiological evaluation of the lung. The persistence of transgene expression in other conditions can be assayed analogously, using the phenotypic alteration correlated to amelioration of the condition. For example, in a lysosomal storage disease, such as Gaucher disease, not only can levels of biologically active enzyme (e.g.β-glucocerebrosidase) be measured, but also a decrease in stored lipid in the cells' lysosomes.

Exemplary dosage ranges for administering adenoviral vectors have been reported (see e.g., Zabner et al., 1996, *J. Clin. Invest.*, 97:1504–1511; incorporated by reference herein). Accordingly, dosage of an adenovirus vector according to the invention will generally fall about within the reported ranges.

Preferably, at least 5 molecules of the bifunctional complex, e.g., a BiFab, per molecule of hexon is used for adenovirus. Because there are 720 moles, of hexon per virus particle, there will be at least about 3600 molecules BiFab per virus particle. Typically, the upper useful limit is about 2000 molecules of bifunctional complex per hexon molecule or about 1,440,000 bifunctional complexes per virus particle, due to potential for immune response. However, some special applications can require higher ratios. A preferred concentration range is from about 5 to about 30 bifunctional complexes per adenovirus hexon. More preferably the concentrations about 25 bifunctional complexes per hexon or 18,000 BiFabs per virus particle (mole:mole).

It is especially advantageous to formulate parenteral compositions in dosage unit form for ease of administration and uniformity of dosage. Dosage unit form, as used herein, refers to physically discrete units suited as unitary dosages for the subjects to whom the constructs of the invention are given, each unit containing a predetermined quantity of active ingredient calculated to produce the desired biochemical or phenotypic effect in association with the required carrier. The specification for the novel dosage unit forms of the invention are dictated by and directly depend on the unique characteristics of the transgene expression system and the limitations inherent in the art of compounding. The principal active ingredient (the virus-bifunctional complex construct) is compounded for convenient and effective administration in effective amounts with the acceptable carrier in dosage unit form as discussed above.

Maximum benefit from administration of the delivery vehicle construct of the present invention may require repeated administration, e.g., as the host cells die or lose their ability to express the factors of interest.

The following examples are provided to more clearly illustrate the aspects of the invention and are not intended to limit the scope of the invention.

EXAMPLE 1
PREPARATION OF FAB FRAGMENTS

Fab fragments were prepared using IMUNOPURE™ Fab Preparation Kit (Pierce Chemical Company, Cat. #44885) according to the following procedure:

A. Preparation of Digestion Buffer: Cysteine-HCl (42 mg) was dissolved in 12 ml of the supplied sodium phosphate buffer. The pH was checked to be 7.0

B. Equilibration of the Immobilized Papain:
0.5 ml of immobilized papain was added to a 16×100 mm polystyrene tube. Digestion buffer (4 ml) was added to the tube. Papain was separated from the buffer using the supplied separator tube and the buffer was discarded. This wash procedure was repeated. The papain was resuspended with 0.5 ml of digestion buffer.

C. Preparation of Antibody:
The antibody was buffer exchanged into 20 mM NaPO$_4$, 10 mM EDTA, pH 7.0. The antibody (0.5 ml) was diluted with digestion buffer (up to 10 mg of IgG).

D. Generation of Fab Fragments:
IgG (1 ml) in digestion buffer was added to the immobilized papain and incubated (5 hrs to overnight) at 37° C. with constant rotation. The digested IgG was recovered from the papain using a separator tube. The papain was washed once with 1.5 ml of IgG Binding Buffer (supplied in kit). Undigested IgG and Fc fragments were removed using immobilized Protein A.

E. Fab Purification:
A protein A column was equilibrated with 13 ml of IgG Binding Buffer. 3 ml of digest was applied and the flow-through was discarded. The column was washed with 6 ml of Binding Buffer and the eluate was collected. The eluate contained pure Fab fragments.

F. Regeneration of Protein A Column:
The Protein A column was regenerated with 10 ml of 0.1 M Citrate, pH 3.0. The column was stored by flushing with 10 ml of PBS+0.02% NaN$_3$.

EXAMPLE 2
CROSS-LINKING OF FAB FRAGMENTS USING HETEROBIFUNCTIONAL REAGENTS

A. Preparation of SATA-Labeled 2Hx-2-Fab:
Fab fragments were buffer exchanged into SATA (N-Succinimidyl S-Acetythioacetate) reaction buffer containing 50 mM NaHPO$_4$, 1 mM EDTA pH 7.5. (Pierce Chemical Co., Cat. #26102). The protein concentration was determined by BCA Assay (Pierce Chemical Co.) and molarity calculated using MW=50,000 Kd.

A 200 mM SATA stock of SATA was prepared in DMSO. SATA was added to equal a 2 to 10 fold molar excess over Fab. About 4 fold molar excess is preferred.

This solution was incubated for up to 30 minutes (but no more) at room temperature. Meanwhile, a PD-10 column (Pharmacia) was pre-equilibrated with 3×5 ml SATA reaction buffer After a 30 minute incubation, SATA-Fab was immediately applied to the PD-10 column. The column was eluted with 10×1 ml SATA reaction buffer and 1 ml fractions were collected. Fractions were assayed for protein by BCA (10 μl of fractions). The fractions containing protein were pooled.

The number of sulfhydryls per Fab fragment was determined using a Thiol and Sulfide Quantification Kit (T-6060) according to the manufacturer's instructions. (Molecular Probes, Inc., Oregon).

B. Preparation of Deacetylation Buffer (fresh):
Hydroxylamine (1.74g) and 0.475g EDTA was dissolved in 45 ml 62.5 mM NaHPO$_4$, pH 7.5. pH was adjusted to 7.5 and then brought to 50 ml, with 62.5 mM NaHPO$_4$.

C. Deacetylation:
Deacetylation solution was added 1:10 (100 μl to ml) to SATA-Fab. This solution was incubated for 2 hours at room temperature. The solution was buffer exchanged on PD-10 column as above.

D. Preparation of SMCC-Labeled anti-$\beta_2$ microglobulin Fab:
Fab fragments were buffer exchanged into SMCC reaction buffer containing PBS, pH 7.2. Protein concentration was determined by BCA Assay (Pierce Chemical Co.) and molarity was calculated using MW=50,000 Kd. A 42.5 mM Sulfo-SMCC stock (Sulfosuccinimidyl 4-(N-maleimidomethyl)cyclohoxane-1-carboxylite; (Pierce Chemical Co., Cat. #22322)) in dH$_2$O was prepared. SMCC was added to equal a 10-fold molar excess over Fab. The solution was incubated for up to 30 minutes (no more than) at room temperature.

Meanwhile, a PD-10 column was pre-equilibrated with 3×5 ml SMCC reaction buffer. After 30 minute incubation, SMCC-Fab was immediately applied to CD-10 column. The column was eluted with 10×25 1 ml SATA reaction buffer and 1 ml fractions were collected. Fractions were assayed for protein by BCA (10 μl of fractions). Fractions containing protein were pooled.

E. Preparation of Bifunctional Fab:
Equimolar amounts of SATA-Fab and SMCC-Fab were combined (e.g. equivalent OD units from BCA Assay were combined) and incubated overnight at 4° C. The reaction was stopped by adding 0.5 M Cysteine, 0.5 M Tris 1:10 to sample. The extent of cross-linking was determined by non-denaturing SDS-PAGE (4%–20%).

F. Purification of Bifunctional Fab:
The sample was concentrated using Ultrafree® 4 30,000 NMWL (Millipore Corp.) to a final volume of approximately 200 μl. A Superose® 12 HR 10/30 column (Pharmacia) was equilibrated with 75 ml PBS pH 7.2 @ 1 ml//min. The sample was loaded (up to 200 μl) at 1 ml/min.

Fractions were then collected (25×1 ml fractions) The fractions (100 μl) were assayed by non-denaturing SDS-PAGE (4%–20%). The fractions that contained monomeric (50 Kd) Fab were discarded and the fractions that appeared to be mostly 100 Kd (bifunctional) were kept.

Figure 2:
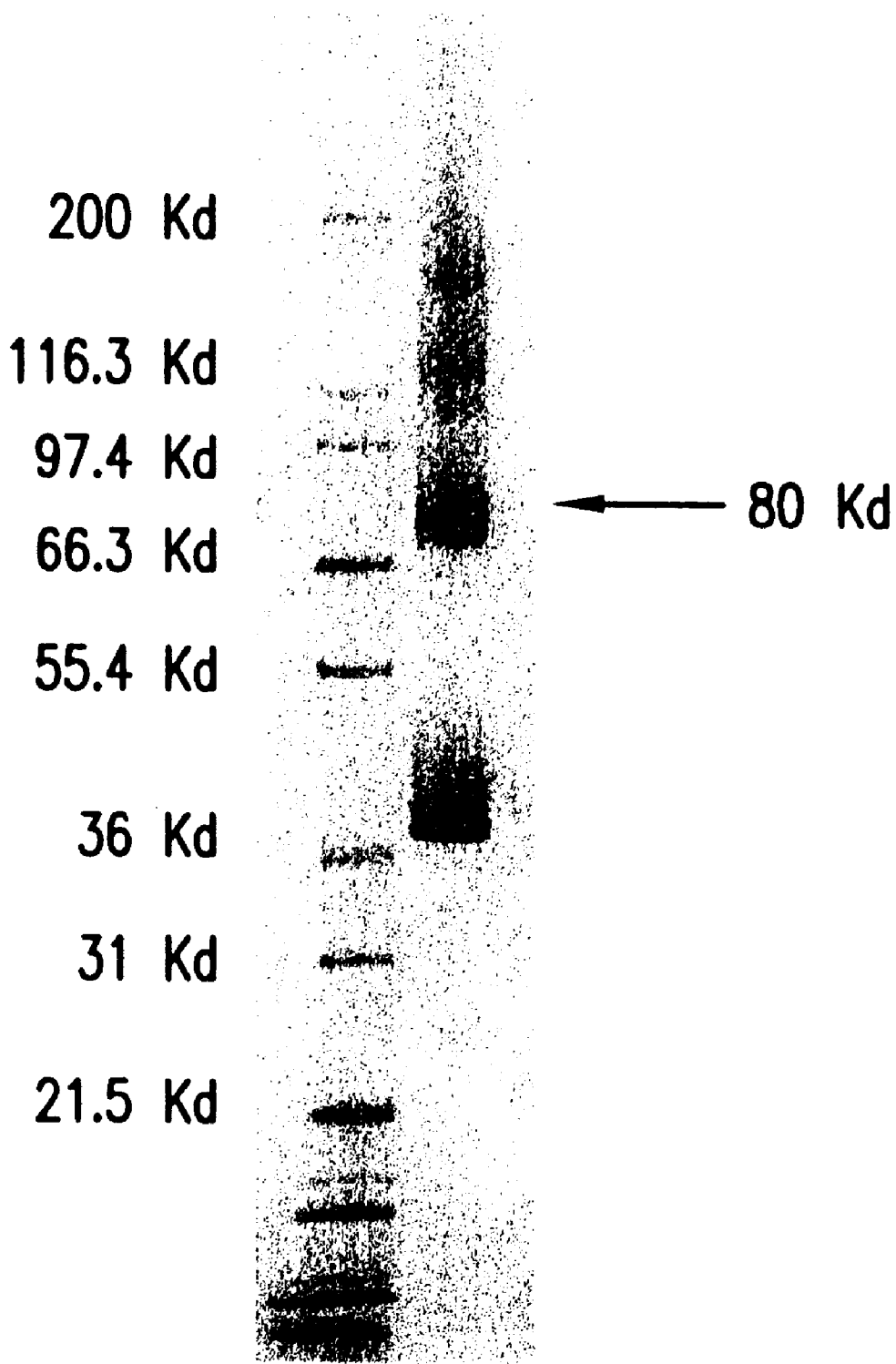
FIG. 2 is a SDS-PAGE gel which shows the generation of bifunctional Fabs using SMCC-Fab and SATA-Fab.

FIG. 2 shows the generation of bifunctional Fab complex using SMCC-Fab and SATA-Fab, having a molecular weight of approximately 80 Kd to 100 Kd.

Figure 3:
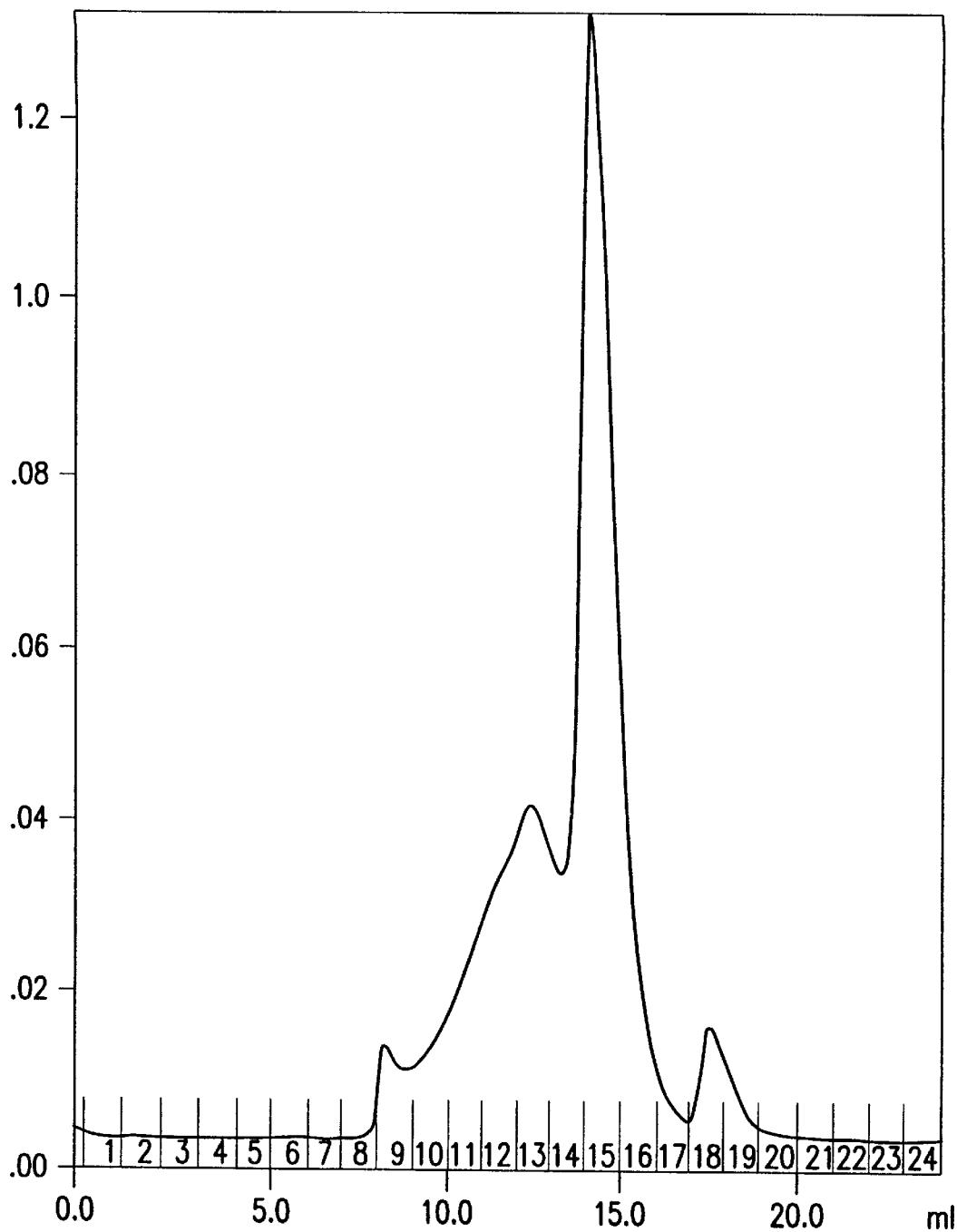
FIG. 3 is a graph showing the gel filtration of bifunctional Fab fragments which results in the separation of the dimeric bifunctional species from monomeric Fab fragments.
Figure 4:
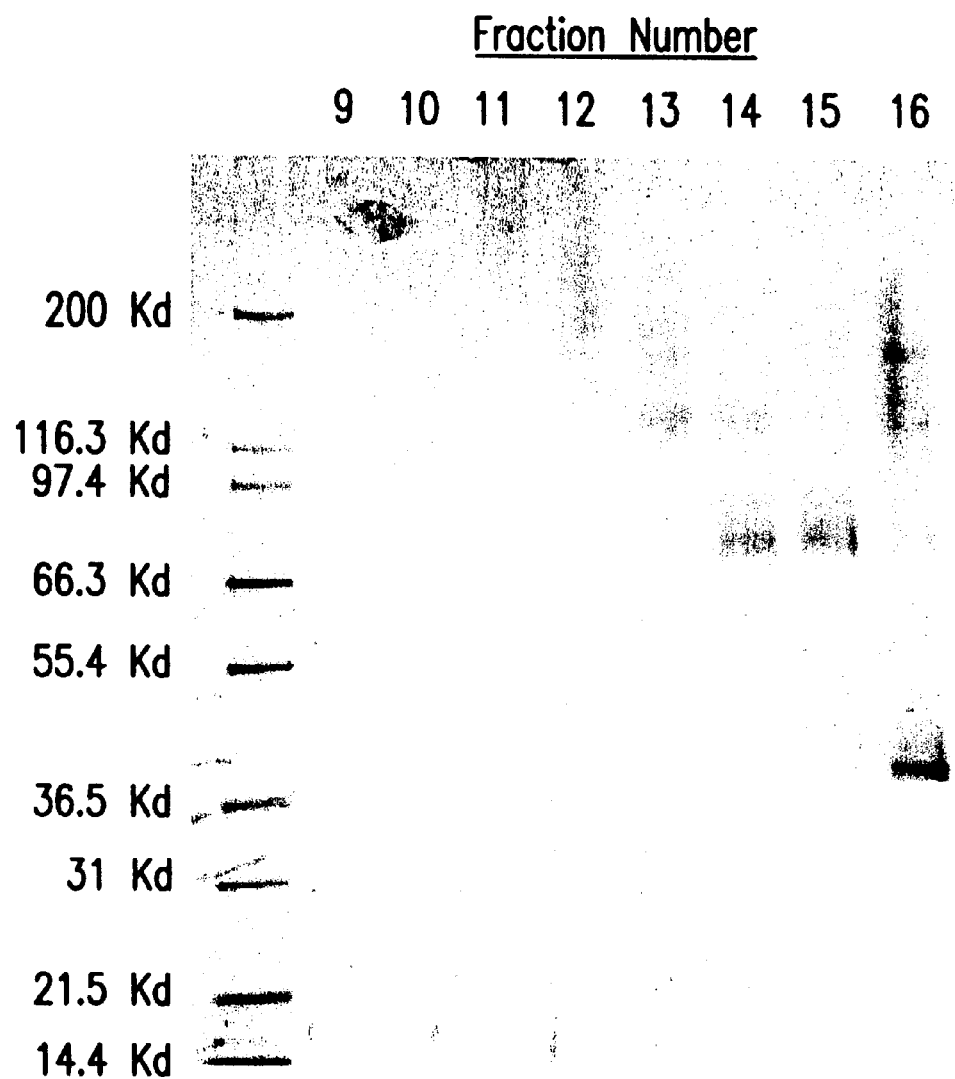
FIG. 4 is a SDS-PAGE gel of the fractions generated from gel filtration of bifunctional Fab fragments as shown in FIG. 3.

FIG. 3 shows the results from gel filtration chromatography of the bifunctional Fab fragments which results in the separation of the bifunctional Fab, complex from monomeric Fab fragments. Gel filtration was performed using a Superose® 12 resin (Pharmacia). SDS-PAGE analysis as shown in FIG. 4, of the fractions generated from gel filtration chromatography of the bifunctional Fab complex/monomeric Fab mixture (FIG. 3) show that a pure bifunctional Fab complex was recovered in fraction 13 while the monomeric Fab species was recovered in later fractions eluted from the resin. The apparent molecular weight of the bifunctional Fab complex species was 100 kDa.

EXAMPLE 3

MEASUREMENT OF THE AFFINITY OF BIFUNCTIONAL FAB FOR ANTIGENS.

The bifunctional hexon-Fab /$β_2$-microglobulin-Fab complex is coated on an ELISA plate. according to methods known in the art. Either biotinylated hexon or biotinylated $β_2$-microglobulin is added to the plate, and incubated for 60 minutes.

The binding of either biotinylated hexon or $β_2$-microglobulin to the plate-bound bi-Fab complex is determined by methods known in the art.

Kinetic parameters for the binding of intact IgG, Fab fragments and bifunctional Fab complexes to their respective antigen were determined using Biacore® (Biacore AB). Purified adenovirus hexon protein or purified $β_2$-microglobulin was immobilized on a CM-5 sensor chip according to manufacture's recommendations. Data was evaluated using Biacore® Evaluation software (Biacore AB) and the results set forth in Tables 4 and 5.

Table 4 shows the affinity of binding of parental 2Hx-2 intact IgG, its Fab fragments and bifunctional Fab complexes to immobilized hexon.

TABLE 4

Biacore ® Analysis of Binding to Immobilized Hexon

| | $k_a$ | $k_d$ | $k_D$ |
|---|---|---|---|
| 2Hx-2 IgG | 8.56 E + 04 | 7.77 E − 05 | 1 nM +/− 0.4 nM |
| 2Hx-2 Fab | 1.47 E + 05 | 1.47 E − 05 | 1.13 nM |
| Bifunctional Fab | 8.41 E + 04 | 5.00 E − 05 | 0.6 nM +/− 0.4 nM |

Table 5 shows the affinity of binding of parental anti-$β_2$-microglobulin. Protease digestion and chemical modification do not have an adverse effect on the kinetics of either antibody binding to its antigen. The bifunctional Fab complex generated using the Fab monomers of both the anti-hexon 2Hx-2 and the anti-$β_2$-microglobulin binds with high affinity to the respective antigens.

TABLE 5

Biacore ® Analysis of Binding to Immobilized $β$2-microglobulin

| | $k_a$ | $k_d$ | $k_D$ |
|---|---|---|---|
| anti-β2m IgG | 1.98 E + 04 | 2.12 E − 04 | 11.8 nM +/− 5 nM |
| anti-β2m Fab | 7.74 E + 04 | 1.47 E − 04 | 1.9 nM |
| Bifunctional Fab | 1.81 E + 04 | 1.21 E − 04 | 8.3 nM +/− 5 nM |

EXAMPLE 4

INFECTION OF HUVEC CELLS

Adenovirus containing the gene for β-galactosidase (Ad2/βgal 2; See, e.g. U.S. Pat. No. 5,670,488, incorporated herein by reference) was incubated with increasing amounts of the anti-hexon-Fab/anti-$β_2$-microglobulin-Fab complex, 0–500 fold excess of bifunctional Fab to virion hexon.

The resulting adenovirus-bifunctional Fab complex construct was then added to a preparation of HUVEC cells, and incubated as follows.

HUVEC cells were plated in 96 well plates at 2.5×10⁴ cells/well=100 μl of 2.5×10⁵ cells/ml suspension. After plating, cells were left at 37° C. until the virus:bifunctional Fab complex was ready, or overnight if targeting for 4 hours or less. (Media=F 12K, 1% glutanine, 1% Pen/Strep, 30 μg/ml ECGS, 100 μg/ml heparin).

Virus was coated with the bifunctional Fab complex for 1 hour at 37° C. using increasing ratios of bifunctional Fab-:hexon.

After coating, the complex (100 μl) was used to infect cells at multiplicity of virus infection [MOI]=20–100. Infection proceeded for 1, 2.5, 4 or 24 hours. If infecting for 1–4 hours, the complex was aspirated from the cells and media replaced.

The cells were then left for 24–72 hours at 37° C. then assayed for transgene expression using the Galactolight® Assay. Cells infected for 24 hours were assayed for transgene expression immediately after the 24 hours.

The expression of β-galactosidase was measured 24, 48 or 72 hours later using the GalactoLight Plus® assay according to the manufacturer's instructions. (GalactoLight Plus, Tropix Cat. # BL300P)

The results are shown in FIG. 5. HUVEC cells, which are normally refractory to infection by native adenovirus, were infected with adenovirus using the bifunctional Fab complex.

Furthermore, the results show that infection efficiency of the HUVEC cells by the adenovirus bifunctional Fab complex construct increased with increasing amounts of the bifunctional complex.

Finally, there was no infection of the cells by the adenovirus in the presence of a non-reactive IgG-Fab conjugate (IgG α-hexon-Fab α-$β_2$). This conjugate also did not bind biotinylated hexon in a binding ELISA.

EXAMPLE 5

ALTERNATIVE TO USING SATA TO PREPARE FAB' FRAGMENTS WHICH HAVE A FREE SULFHYDRYL

Fab' fragments were prepared using Immunopure® F(ab')₂ Preparation Kit (Pierce Chemical Co., Cat. #44888) according to the following protocol.

1. Preparation of Digestion Buffer: (20 mM NaAcetate pH 4.5)

Sodium acetate trihydrate (2.72 g) was dissolved in 1 L of dH₂O. The pH was adjusted to 4.5.

2. Equilibration of Immobilized Pepsin:

0.25 ml of immobilized pepsin was added to a 16×100 mm polystrene, tube. 4 ml of digestion buffer was added.

Pepsin was separated from buffer using supplied separator tube and the buffer was discarded. The wash procedure was repeated. The pepsin was resuspended with 0.5 ml of digestion buffer.

3. Preparation of Antibody:

Up to 10 mg/ml antibody was buffer exchanged into digestion buffer.

4. Generation of F(ab')$_2$ Fragments:

1 ml of IgG in digestion buffer was added to the immobilized pepsin and incubated for 4 hrs, at 37° C. with constant rotation. Digested IgG was recovered from pepsin using separator tube. Pepsin was washed once with 1.5 ml of IgG Binding Buffer (supplied). Undigested IgG and Fc' fragments were removed using Immobilized Protein A.

5. F(ab')$_2$ Purification:

A Protein A column was equilibrated with 13 ml of IgG Binding Buffer. 3 ml of digest was applied and the flow-through discarded. The column was washed with 6 ml of Binding Buffer and the eluate collected. The eluate contained pure F(ab')$_2$ fragments.

6. Cleaning of Protein A Column:

The column was regenerated with 10 ml of 0.1 M Citrate pH 3.0. The column was prepared for storage by flushing with 10 ml of PBS+0.02% NaN$_3$.

7. Preparation of Fab° Fragments:

Reduction Buffer was prepared as follows: 100 mM NaPO$_4$, 5 mM EDTA pH 6.0. F(ab')$_2$ fragments were buffer exchanged into reduction buffer (up to 10 mg/ml). 1 ml of F(ab')$_2$ was added to 1 vial (6 mg) of 2-mercaptoethylamine. (2-Mercaptoethylamine HCl, Pierce Chemical Co., Cat. #20408). This solution was incubated for 90 minutes at 37° C. The mercaptoethylamine was separated from Fab' using a pre-equilibrated PD-10 column (Pharmacia, Cat. # 17-0851-01 (or equivalent Sephadex® G 25 M)) in PBS containing 1 mM EDTA. Fractions (1 ml) were collected and fractions were assayed for protein using BCA Assay. (BCA Protein Kit, Pierce Chemical Co., Cat. #23225). Fractions containing Fab' were pooled.

EXAMPLE 6
INCREASED INFECTION OF HUMAN DENDRITIC CELLS BY ADENOVIRUS IN THE PRESENCE OF A BIFUNCTIONAL FAB COMPLEX.

Human dendritic cells were prepared as described by Christian Radmayr et al., 1995, *Int. J. Cancer* 63:627–632 and plated out an a 96 well tissue culture plate at a density of 1×10$^4$ cells per well. Fab fragments of both the anti-hexon antibody (2Hx-2) and the anti-β$_2$-microglobulin antibody were prepared as described in Example 1 and cross-linked together as described in Example 2 to generate a bifunctional Fab complex which recognized both adenovirus and β$_2$-microglobulin. Ad2/βgal4 virus encoding the transgene green fluorescence protein was incubated with the bifunctional Fab complex at a ratio of 10:1 and 50:1, bifunctional Fab:hexon (mole:mole) for 1 hour at 37° C.

The adenovirus-bifunctional Fab complex at an MOI of 100 was used to infect dendritic cells for 24 hours. Control dendritic cells were infected with adenovirus alone. After this time, the cells were visualized under a fluorescence microscope and the number of cells expressing green fluorescence protein was determined.

Figure 6:
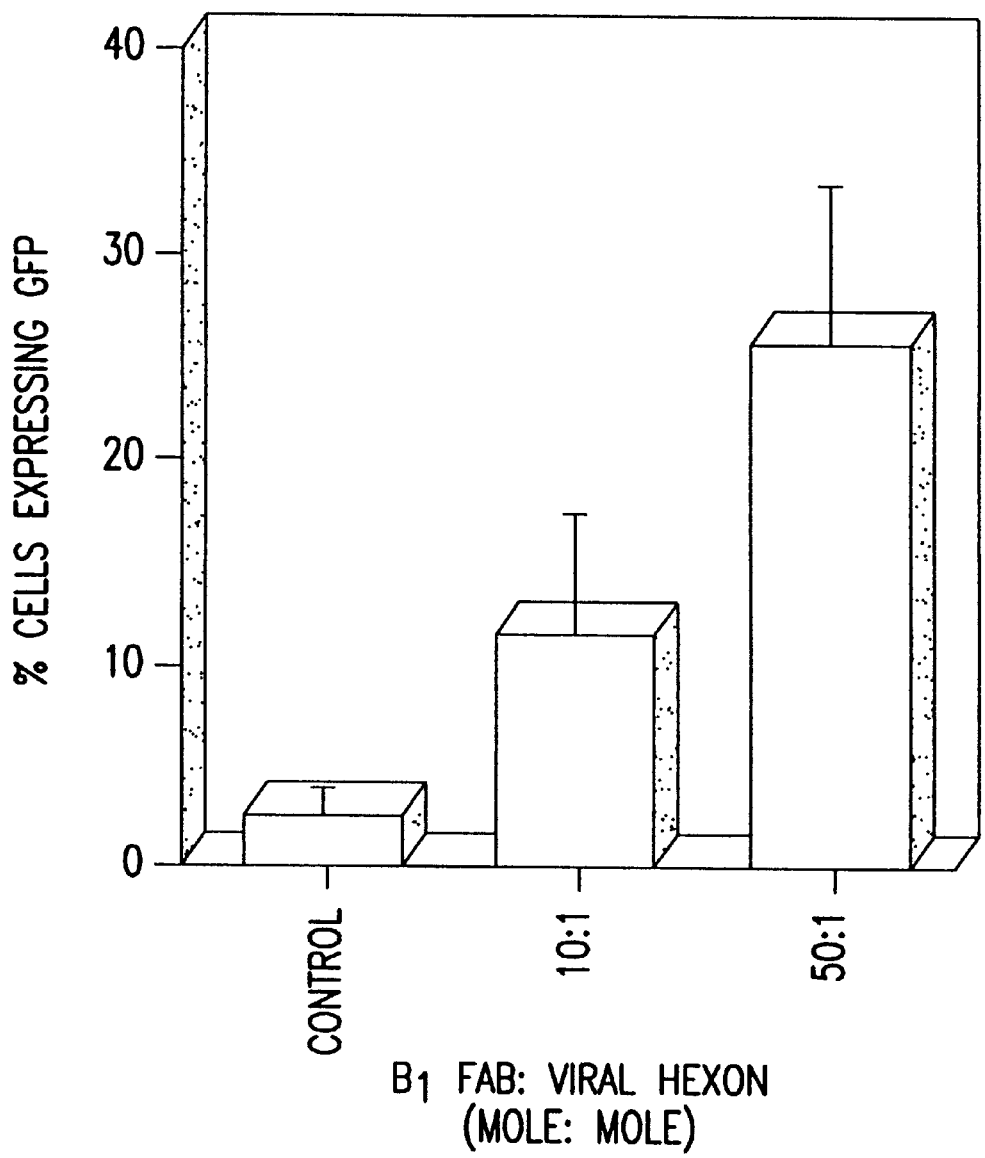
FIG. 6 is a graph showing the increase in infection of human dendritic cells by adenovirus in the presence of bifunctional Fab conjugates.
Figure 7A:
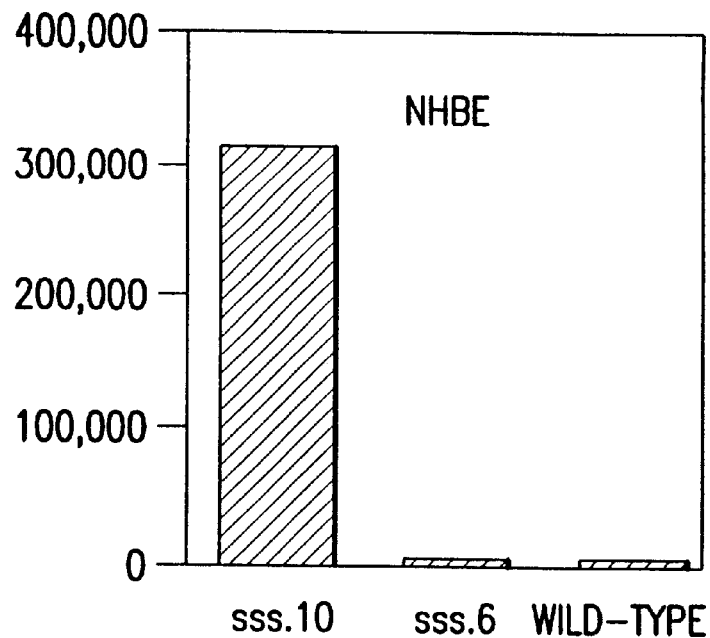
FIGS. 7A–G are bar graphs showing the relative binding of selected phage to cells. A comparison of affinity differences between various cell lines is illustrated with primary human epithelial cells (NHBE, SAEC), transformed cells (HeLa, 293), rat glioblastoma cells (9L), or mouse cells (CV-1, COS).
Figure 7B:
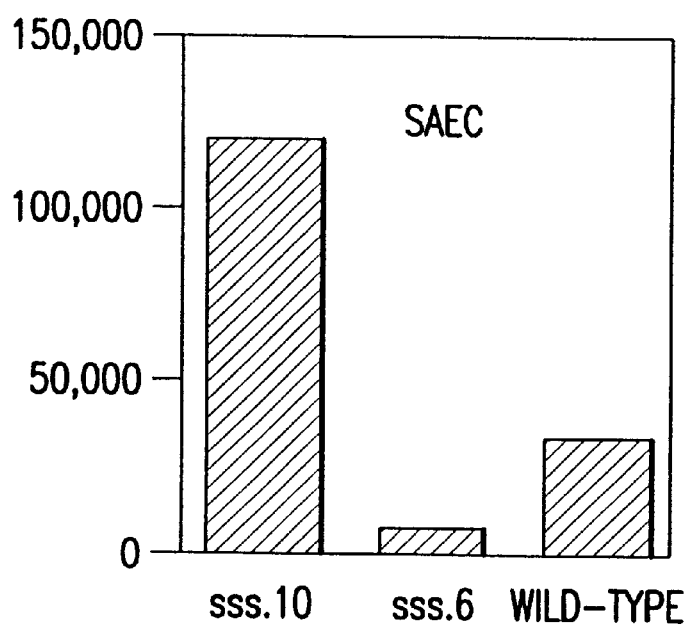
Figure 7C:
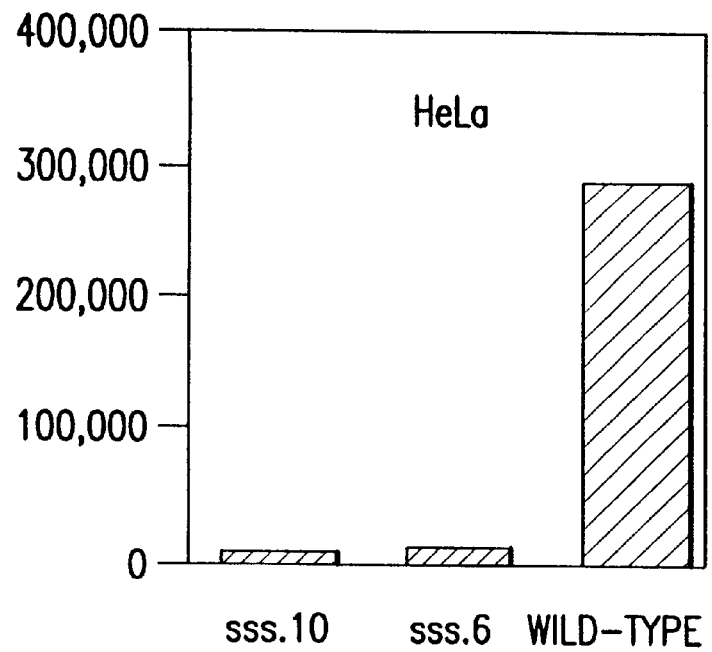
Figure 7D:
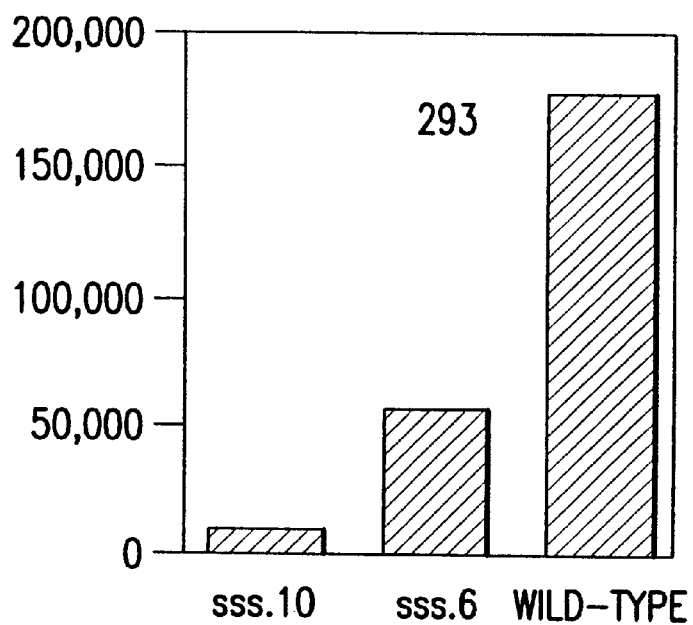
Figure 7E:
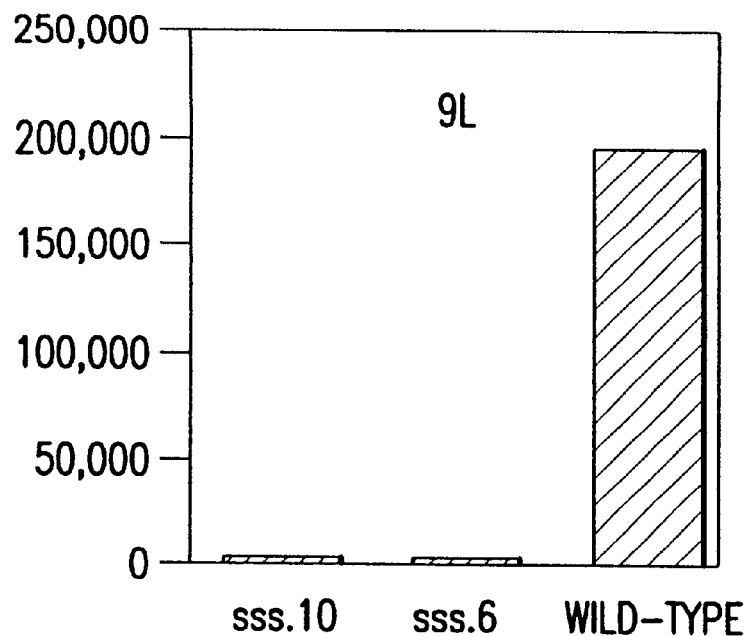
Figure 7F:
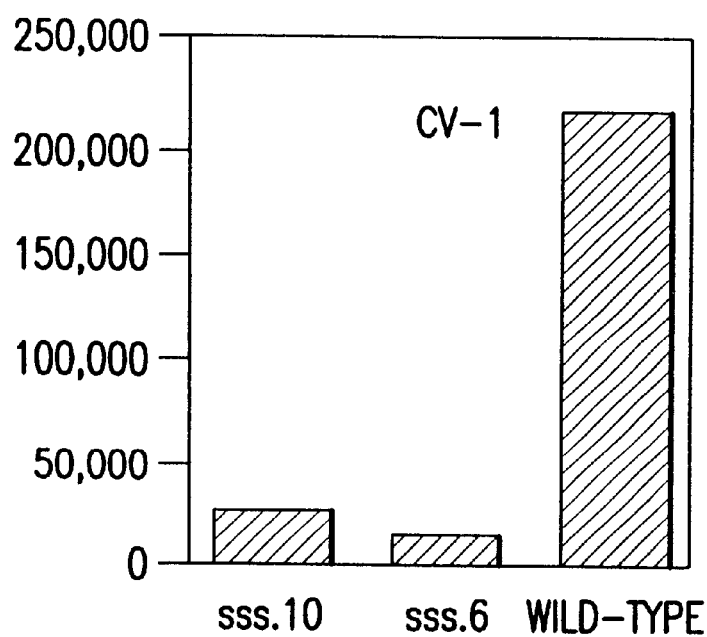
Figure 7G:
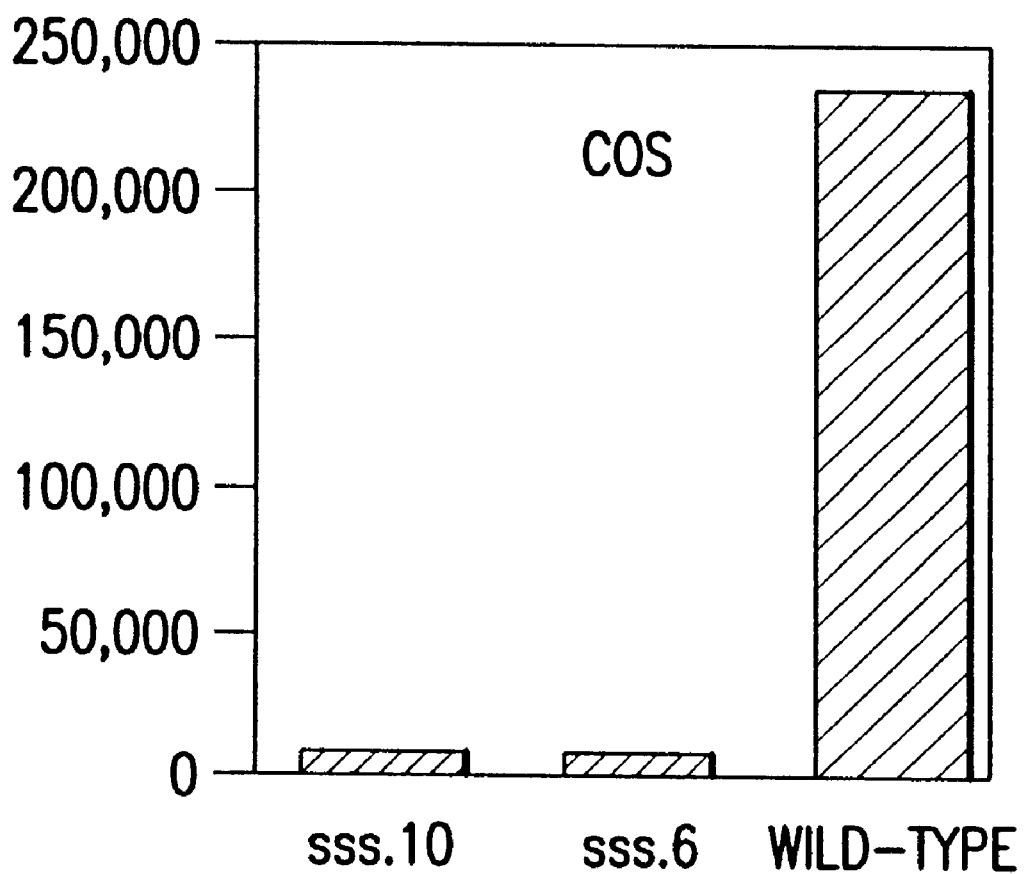

The number of control dendritic cells infected with adenovirus alone was determined by visualizing under a flourescent microscope, the number of cells expressing green fluorescence protein (FIG. 6). Control dendritic cells infected with adenovirus alone were found to have a low percentage of cells expressing green fluorescence protein suggesting that dendritic cells are poorly infected by adenovirus. Cells that were infected with adenovirus pre-treated with the bifunctional Fab fragment (50:1, bifunctional Fab:hexon) showed a ten fold increase in expression of green fluorescence protein compared to control cells infected by adenovirus alone (FIG. 6). Thus, pretreatment of adenovirus with a bifunctional fab fragment which recognizes both adenovirus and MHC I leads to an increase in the infection of dendritic cells that are normally refractory to infection by adenovirus alone at low MOI.

EXAMPLE 7
SELECTION OF PHAGE WITH HIGH AVIDITY FOR NHBE CELLS.

A. Growth of Primary Cell lines

Primary normal human bronchial epithelial (NHBE) cells were purchased from Clonetics (San Diego, Calif.) and grown in BEGM media with added supplements as recommended by the supplier. For biopanning experiments, frozen cells were thawed and centrifuged, then used directly for binding. The NHBE cells used during the course of the experiments were obtained from several donors.

B. Phage Selection and Peptide Isolation

For selection of phage with high avidity for NHBE cells, the cells in suspension were bound with 1×10$^{11}$ infectious units (IU) of a phage library (purchased from New England Biolabs) in a buffer containing 3% bovine serum albumin (BSA), 0.1% hydrolysate cagein, 0.02% azide (to prevent internalization of the bound phage) in HBSS without magnesium or calcium. Non-specific phage were removed by excessive washes with the same buffer. Avid-binding phage were then acid-eluted with 0.12 M glycine pH 2.0./0.5% BSA for 5 minutes at room temperature and then amplified in bacteria. After three rounds of biopanning repetition, phage DNAs from 20 separate plaques were extracted and sequenced in the region of the gene m fusion to identify any amino acid sequence similarities among the peptides. As shown in Table 3, 4 subgroups of peptides were identified, based on their sequence similarities. Two of the displayed peptides, phage sss.10, SEQ ID NO:15 and sss.14, SEQ ID NO:16, had identical amino acid sequences.

C. Preference of Phage Isolated From Phage Biopanning for NHBE Cells

It was also determined whether phage with high avidity for NHBE cells also showed a preference for other human cells or for cells derived from other species. To test for such comparative avidities, phage sss.10, SEQ ID NO:15 and sss.6, SEQ ID NO:21, whose amino acid sequence is quite different from sss.10, SEQ ID NO: 15, were chosen (see Table 3). Each phage was bound, in similar numbers from a master mix, to equal amounts of human cells including NHBE, SAEC, HeLa, and 293 cells, of rat 9L cells, or of monkey cells including COS-1 and CV-1. After extensive washing of non-specifically bound phage, avid binding phage were acid eluted as described above, and neutralized, then measured by titering on lawns of bacteria. FIG. 7 shows that one of the tested phage isolates, sss.10, SEQ ID NO:15, has a high avidity for both NHBE cells and SAEC cells, derived from upper and lower respiratory tracts of human donors, respectively. In contrast, sss.10, SEQ ID NO:15 has no real avidity to the other human cells tested (HeLa, or 293) or for rat (9L) and monkey (COS, CV-1) cells. sss.6, SEQ ID NO:20 did not show a striking avidity for any of the cells tested in this assay.

D. Preference of Phage Isolated From Phage Biopanning for NHBE Cells Grown on Air-Liquid Interfaces (ALIs)

Figure 8:
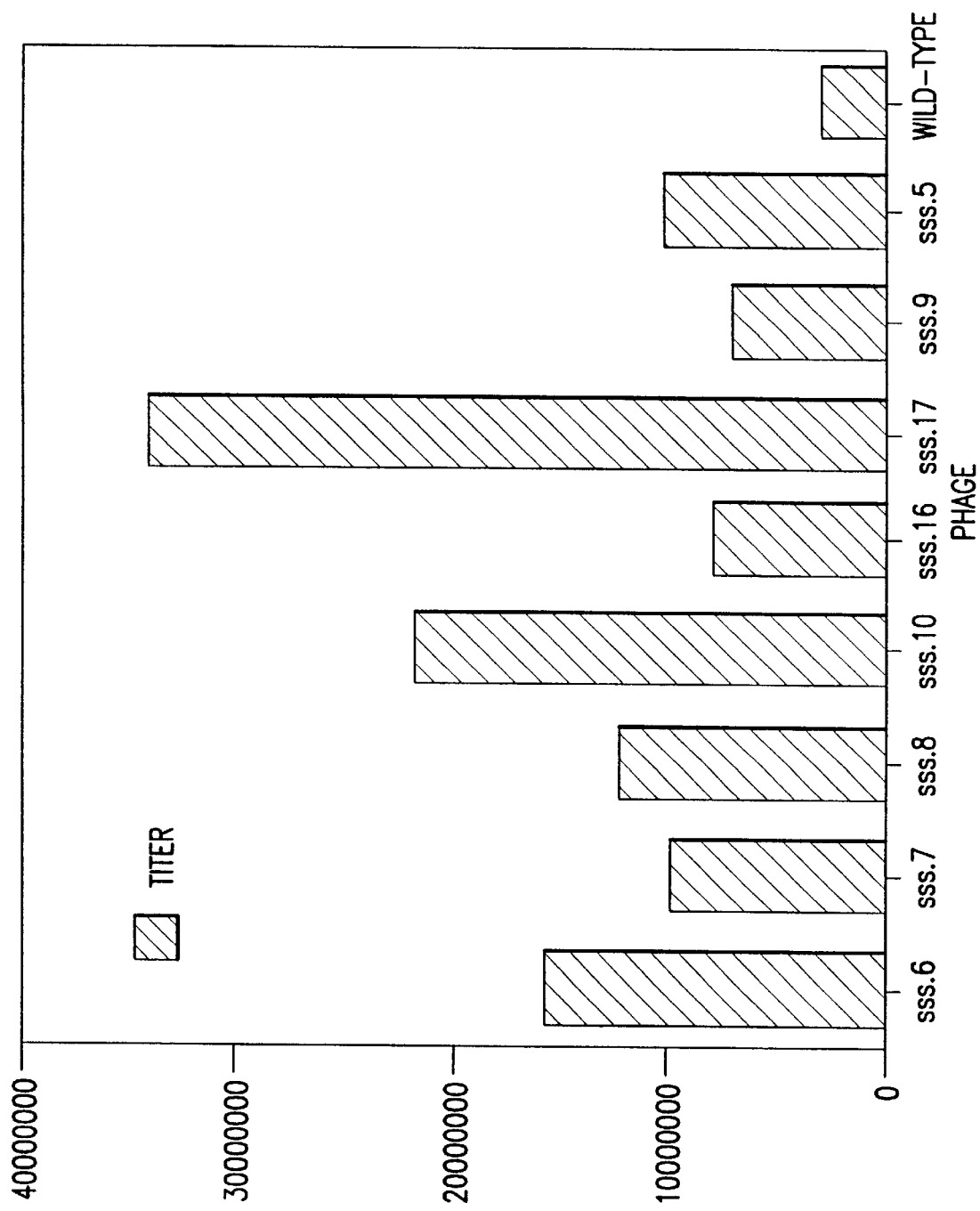
FIG. 8 is a bar graph showing the avidity of various selected phage constructs for differentiated, ciliated primary human airway epithelial cells (NHBE cells). Numbers shown are numbers of plaques from each titer assay.

Because NHBE cells are not representative of a human airway surface, phage avidity was also tested on NHBE cells grown on ALIs. Cells grown in this fashion differentiate in a pseudo-stratified layer, with a histology resembling in vivo airway epithelia. Gray, T. E. et al., 1996, *Am. J. Respir. Cell Mol. Biol.* 14:104–112; Yamaya, M. et al., 1992, *Am. J. Physiol.* 262:L713–724. Each of the phage selected by biopanning in suspension (Table 3) or phage displaying a wild-type filament III, were bound, in equal amounts, to differentiated, ciliated NHBE cells grown on ALIs. Bound phage were washed extensively, then acid-eluted and titered on lawns of bacterial cells to determine the comparative extent of binding as described above. FIG. 8 shows that each of the monoclonal sss phage had a 2 to 10-fold higher avidity than wild-type phage for NHBE cells grown on ALIs, based on comparative binding. sss.10, SEQ ID NO:15 and sss.17, SEQ ID NO:23 had the highest avidities, showing a 7 to 10-fold increased titer in comparison to wild-type phage. Specific binding of the sss.10, SEQ ID NO:15 and sss.17, SEQ ID NO:23 phage to NHBE cells on ALIs was also detected by immunofluorescence.

EXAMPLE 8
CHEMICAL COUPLING OF PEPTIDES TO AN ADENOVIRAL VECTOR

Figure 9:
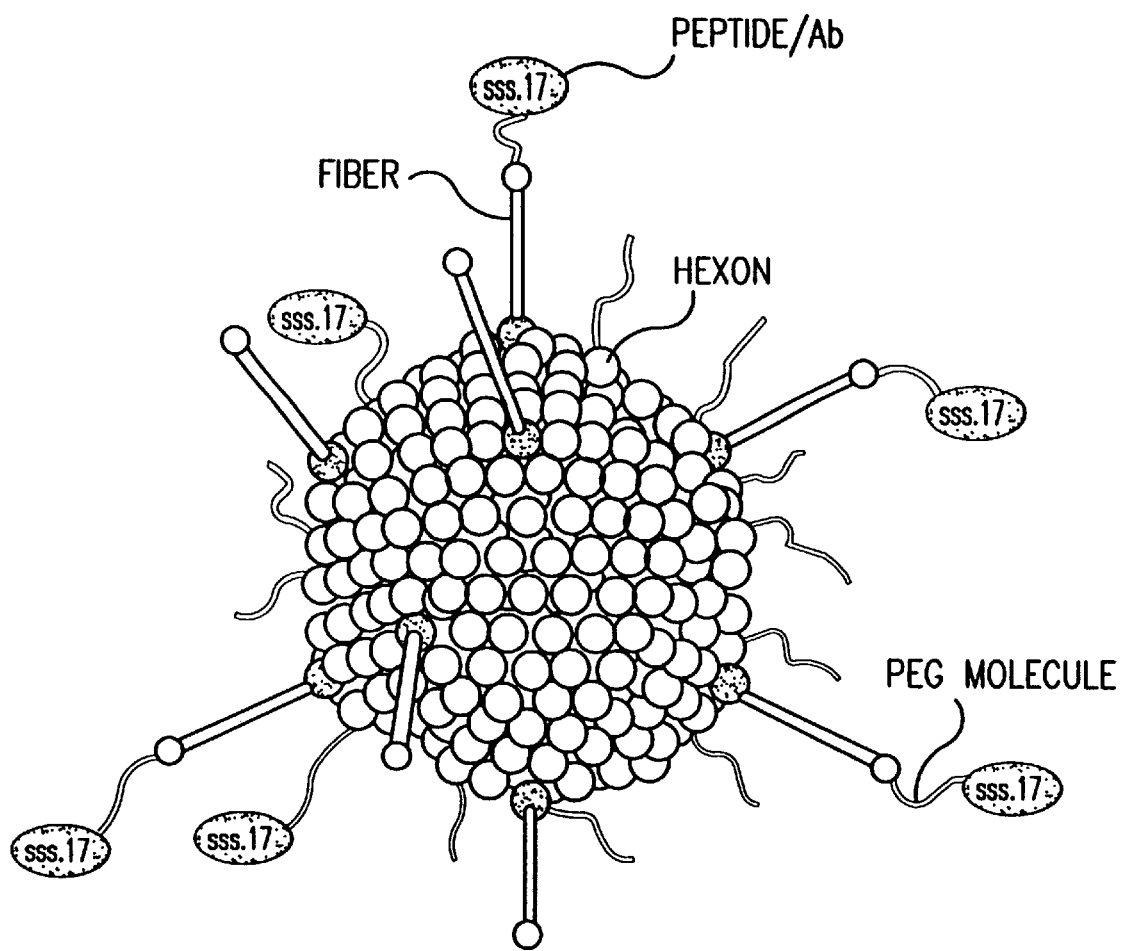
FIG. 9 is a diagrammatic representation of an adenoviral vector modified by the addition of PEG and sss.17 peptide, SEQ ID NO:23.

Recombinant reporter adenovirus vectors, Ad2/βgal-4 (Armentano, D. et al., 1997, *J. Virol.* 71:2408–2416) and Ad-CFTR (Rich, D. P. et al., 1993, *Human Gene Therapy* 4:461–476) was modified by the addition of either NHS-PEG-vinylsulfone (NHS-PEG-VS) or tresyl MPEG-maleimide. The NHS and tresyl moieties of the bifunctional PEG molecules react with amine groups on the surface of the virus, while the vinylsulfone and maleimide groups are selective for reaction with sulfhydryl groups introduced on the sss.17, SEQ ID NO:23 peptide. Ad2/βgal-4 virus in phosphate buffered saline (PBS) pH 7.0 was reacted with NHS-PEG-vinylsulfone or tresyl-PEG-maleimide. Virus and PEG were incubated for one hour, after which time PEGylated virus was reacted with the sss.17 peptide, SEQ ID NO:23. sss.17, SEQ ID NO:23 was commercially synthesized to include a terminal cysteine with a free sulfhydryl-SDQLASPYSHPRC-amide (SEQ ID NO:23). The peptide was coupled to the virus for 4 hours at room temperature or overnight at 4° C. The final modified vector, Ad2/PEG-sss.17, SEQ ID NO:23, is shown diagrammatically in FIG. 9.

EXAMPLE 9
Ad2-PEG-sss.17 BINDING AND INFECTION EFFICIENCY AND BINDING COMPETITION EXPERIMENTS A. Establishing Well-differentiated Human Airway Epithelial from Surgical Specimens.

Airway epithelial cells were obtained from surgical polypectomies of non-CF patients or from trachea and bronchi of lungs removed for organ donation. Cells were isolated by enzyme digestion as previously described. Zabner, J. et al., 1996, *J. Virol.* 70:6994–7003. Freshly isolated cells were seeded at a density of $5 \times 10^5$ cells/cm onto collagen-coated, 0.6 cm$^2$ diameter millicell polycarbonate filters (Millipore Corp., Bedford, Mass.). The cells were maintained at 37° C. in a humidified atmosphere of 7% $CO_2$ and air. Twenty-four hours after plating, the mucosal media was removed and the cells were allowed to grow on an ALI. Yamaya, M. et al., 1992, *Am. J. Physiol.* 262:L713–L724. The culture media consisted of a 1:1 mix of DMEM/Ham's F12, 5% ultraser G (Biosepra SA, Cedex, France), 100 U/ml penicillin, 100 μg/ml streptomycin, 1% nonessential amino acids, and 0.12 U/mi insulin. Fourteen days after seeding, samples of epithelia were tested for transepithelial resistance and for morphology by scanning electron microscopy.

B. Infection of Well-differentiated Airway Epithelia.

Well-differentiated ciliated human airway epithelia ($1 \times 10^6$ cells) were incubated with virus ($10^9$ particles) for 30 minutes, then rinsed twice with PBS.

Forty-eight hours post-infection, β-galactosidase activity was assayed using the Galactolite® assay (Tropic Inc., Bedford, Mass.) and total protein was assayed by calorimetric assay (Bio-Rad Lab, Hercules, Calif.) as previously described. Zabner, J. et al., 1996, *J. Virol.* 70:6994–7003. For competition assays, airway epithelia were incubated with varying concentrations of sss.17 peptide or adenovirus type 2 (Ad2) fiber knob for 15 minutes at 4° C. Recombinant adenoviruses were then added to the apical surface and allowed to bind at 4° C. for 15 minutes. The epithelia were rinsed twice with PBS and incubated at 37° C. for forty-eight hours before assaying for β-galactosidase activity. HeLa cells were grown in 24 well plates to 70% confluence and infected with $10^9$ particles virus in PBS.

C. Infection of CF Epithelia Cells

Human epithelial cells from a nasal polyp of a CF patient were cultured on permeable filter supports (CF epithelia cells). These cells form an electrically tight epithelial monolayer after several days in culture. Eight days after seeding, the cells were exposed to the Ad-CFTR virus vector for 6 hours. Three days post infection, monolayers were mounted in Using chambers and short-circuit current was measured. To determine the presence of functional CFTR, bumetanide (an inhibitor) was added and the change in short circuit current was measured.

D. Ad2-PEG-sss.17 Binding and Infection of Well-differentiated Human Airway Epithelial Cells.

Figure 10A:
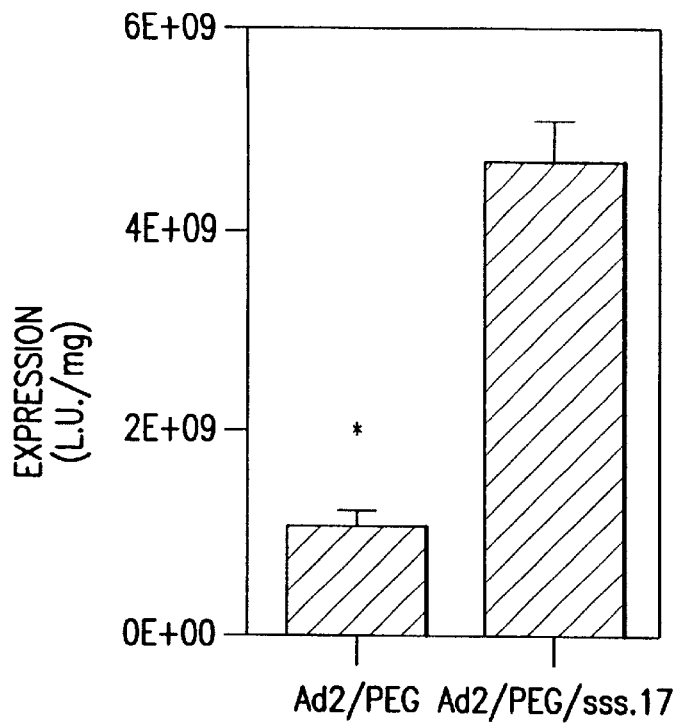
FIGS. 10A–B are graphs showing the infection efficiency of PEG-peptide modified adenoviruses. Infection efficiency was measured by the ability of primary cultures of well-differentiated human airway epithelial cells (A), and HeLa cells (B), to express the gene product (β-galactosidase).
Figure 10B:
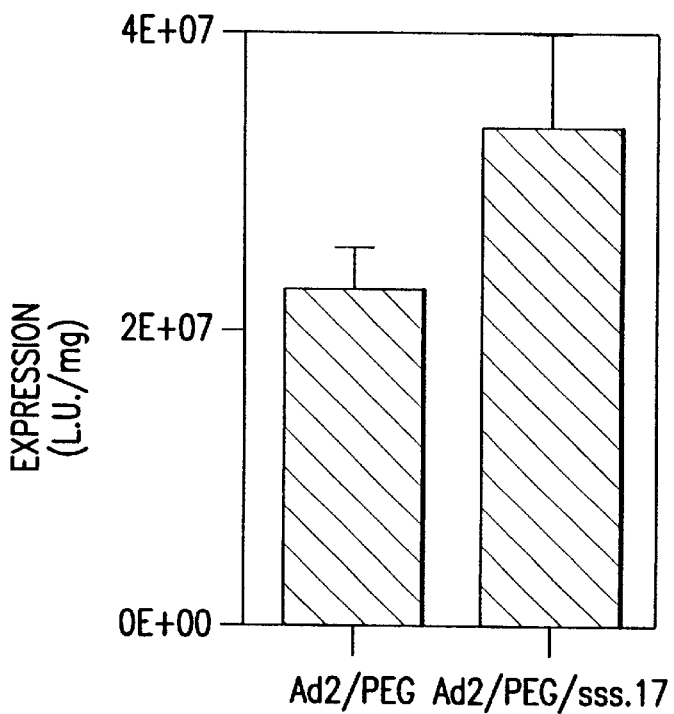
Figure 11A:
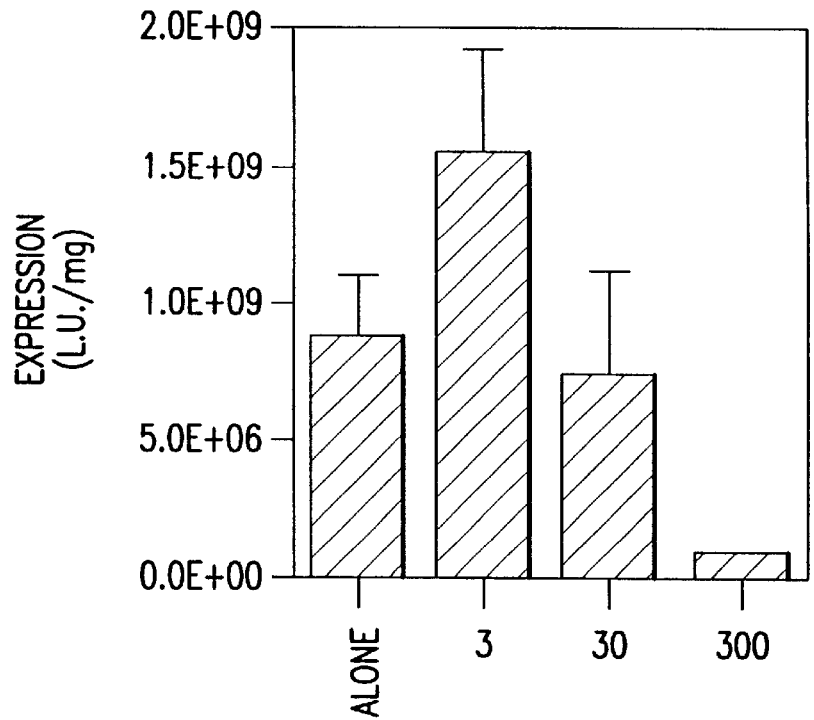
FIGS. 11A–B are graphs of the competition of PEG-peptide modified adenovirus infection efficiency by excess peptide measured by the ability of the infected cell to express β-galactosidase. (A) Primary cultures of well-differentiated human airway epithelial cells. (B) HeLa cells.
Figure 11B:
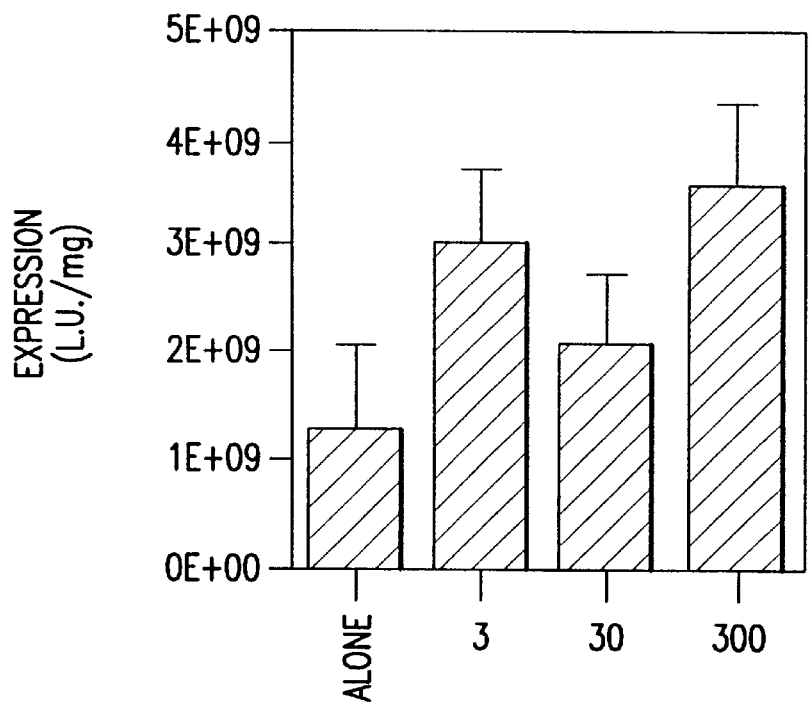

The coupling of sss.17, SEQ ID NO:23 to adenovirus was predicted to increase vector delivery to human airway cells, due to the avidity of the peptide for some component of the epithelial cell surface (FIGS. 7 and 8). FIG. 10A shows that an adenoviral vector expressing the β-galactosidase gene and modified with a bifunctional PEG and sss.17, SEQ ID NO:23 (Ad2-PEG-sss.17) infects well-differentiated airway epithelial cells grown on ALIs with a 4-fold higher efficiency than a vector lacking the peptide (Ad2-PEG) as measured by β-galactosidase activity in the cells. This result indicated that sss.17, SEQ ID NO:23 mediates increased vector infection capacity. This confirms that the use of NHBE cells in the phage biopanning experiments led to obtaining isolated peptides that had an avidity for NHBE airway epithelial cells as well as primary cultures of well-differentiated airway epithelial cells from donors. See FIG. 10A. In contrast, the infection of HeLa cells with Ad2-PEG and Ad2-PEG-sss.17, SEQ ID NO:23 showed no statistically significant difference (FIG. 10B) as measured by the amount of β-galactosidase activity in the cells. These results support the earlier biopanning data, which showed that phage displaying the sss.17, SEQ ID NO:23 peptide have a high avidity for NHBE human airway cells but little avidity for HeLa cells (FIG. 8). The infection of well-differentiated human airway epithelial cells by Ad2-PEG-sss.17 can be competed by excess sss.17, SEQ ID NO:23 peptide (FIG. 11A), further suggesting that the increased infectivity of the modified viral complex is mediated by the coupled peptide. In contrast, sss.17, SEQ ID NO:23 did not compete infection by Ad2-PEG-sss.17 in Hela. See FIG. 11B.

E. Ad2-CFTR-PEG-sss.17 Correction of Chloride Channel Defects in CF Epithelia Cells.

Figure 17:
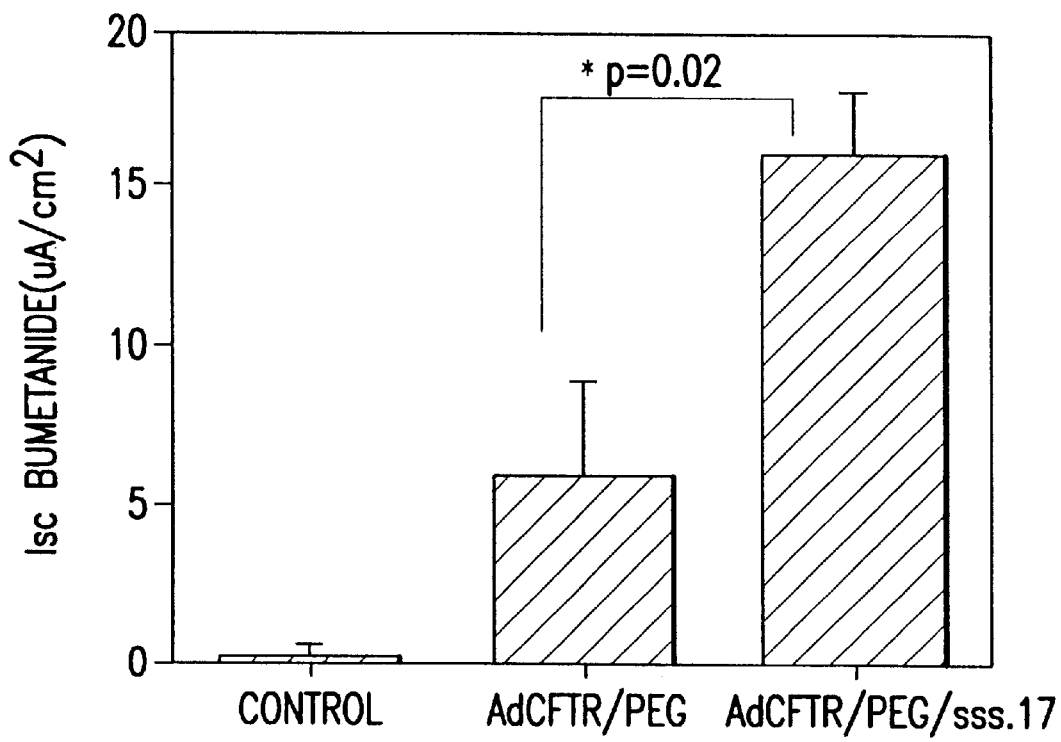
FIG. 17 is a graph showing the ability of a bifunctional PEG-sss.17 modified adenovirus encoding CFTR to correct the chloride channel defect in epithelia cells from an individual with cystic fibrosis.

The ability of Ad-CFTR virus construct coupled to sss.17 via a bifunctional PEG molecule, as described above, to correct chloride channel defects in CF epithelial cells was measured. FIG. 17 demonstrates that Ad-CFTR coupled to sss.17 via a bifunctional PEG molecule was three times more effective in correcting the chloride channel defect in CF epithelial cells than Ad-CFTR alone. The measurements show the change in short circuit current in the presence of bumetanide. A larger change in short circuit current indicates greater levels of CFTR expression. These data indicate that when an adenovirus comprising a transgene encoding for CFTR is coupled to sss.17 via the bifunctional molecules of the present invention, greater efficiency in correction of chloride channels in CF epithelia is achieved.

F. Ad2-PEG-sss.17 Uses a Fiber Knob Receptor-Independent Mechanism of Binding In Well-Differentiated Human Airway Epithelial Cells.

Efficient adenoviral entry into the natural target cells for the virus requires viral attachment to the Coxsackie adenovirus receptor (CAR) at the cell surface (Bergelson, J. M. et al., 1997, *Science* 275:1320–1323; Tomko, R. P. et al. 1997, *Proc. Natl. Acad. Sci.* 94:3352–3356) and internalization via integrin receptor-mediated endocytosis. The viral fiber knob is required for the initial attachment step, while penton base mediates the internalization process. Persson, R. et al., 1985, *J. Virol.* 54:92–97. Several investigators have now shown that differentiated airway epithelial cells lack the appropriate receptors for efficient viral entry via the fiber knob/penton base-mediated pathways. Goldman, M. J. et al., 1995, *J. Virol.* 69:5951–5958; Pickles, R. J. et al., 1998, *J. Virol.* 72:6014–6023; Zabner, J. et al., 1997, *J. Clin. Invest.* 100:1144–1149. To distinguish the pathway by which sss.17, SEQ ID NO:23 mediates viral entry, the infection efficiency of Ad2-PEG-sss.17 was tested in the presence of excess fiber knob, which should compete for receptor-mediated infection dependent on fiber knob/CAR interaction.

Well-differentiated human airway epithelial cells grown on ALIs were infected with adenovirus in the presence or absence of competing fiber knob protein. FIG. 12A shows that in well-differentiated human airway epithelial cells grown on ALIs, infection by Ad2-PEG-sss.17 was not competed by excess fiber knob. In contrast, infection of HeLa cells by Ad2-PEG-sss.17 was competed by excess fiber knob (FIG. 12B), confirming that viral entry occurs independently of sss.17, SEQ ID NO:23 in cells that have ample supply of the appropriate fiber and penton base receptors (Zabner, J. et al., 1997, *J. Clin. Invest.* 100:1144–1149; Persson, R. et al., 1985, *J. Virol.* 54:92–97) but little avidity for the added peptide.

EXAMPLE 10
PREPARATION OF BIFUNCTIONAL ANTIBODY.

A. Materials: Immunopure® Fab Preparation Kit (Pierce Chemical Co., Cat. #44885; (Traut's Reagent, Pierce #26101; 4-(4-N-maleimidophenyl) butyric acid hydrazide (MPBH) (Pierce Chemical Co., Cat. #22305); PD-10 Columns (Pharmacia #12-0851-01); SUPERDEX 200 10/30 (Pharmacia); Ultrafree® 4 Centrifugal Filters (Millipore).

B. Preparation of Bifunctional 2Hx-2-AF20 Conjugates.

Monomeric Fab fragments of intact Mab 2Hx-2 (anti-hexon monoclonal antibody) were prepared by digestion with immobilized papain as in Example 5 above. The immobilized papain was first activated by washing with 20 mM cysteine in sodium phosphate buffer, pH=7.0 and added to 2Hx-s whole IgG which had previously been dialyzed into 20 mM sodium phosphate buffer pH 7.0, containing 10 mM EDTA. Digestion was allowed to occur for 4 to 6 hours at 37° C. after which time the immobilized papain was removed by low speed centrifugation while undigested IgG was removed by passing the digest over a Protein A resin. The fraction which did not bind to the Protein A resin, i.e. the Fab fragments, was exchanged into the phosphate buffered saline pH 8.0 containing 1 mM EDTA and labeled with Traut's reagent using a 10-fold molar excess. Fab fragments were labeled for one hour at room temperature after which time any excess Traut's reagent was separated from labeled Fab fragments using a PD-10 (Pharmacia) column equilibrated with phosphate buffered saline (pH 7.1) confining 1 mM EDTA.

Maleimide groups were incorporated into AF20 IgG using the heterobifunctional cross-linker 4(4-N-maleimidophenyl) butyric acid hydrazide (MPBH). AF20 IgG in 0.1 M sodium acetate buffer pH 5.5 was oxidized in the presence of 10 mM sodium meta-periodate for one hour at 4° C. Reaction was allowed to take place in the dark. The oxidation was stopped by the addition of 1/10th volume 200 mM glycerol followed by a 5 minute incubation at 4° C. Excess sodium meta-periodate was removed by dialysis into sodium acetate buffer pH 5.5 at 4° C. MPBH was prepared in dimethylsulfoxide (DMSO) and used to label the oxidized IgG at a final concentration of 1 mM MPBH. Labeling took place at room temperature for 2 hours. Unreacted MPBH and sodium meta-periodate was removed using a PD-10 column as above.

Mab 2Hx-2 labeled with Traut's reagent was cross-lined to MPBH-labeled AF20 by overnight incubation at 4° C. The cross linked bifunctional product was purified form monomeric components by gel filtration chromatography using a Superdex® 200 10/30 column which had been pre-equilibrated with phosphate buffered saline pH 7.1. Fractions from the Superdex® column were assayed for bifunctional 2Hx-2-AF20 conjugate by SDS-PAGE and ELISA.

C. ELISA Assay for the Detection of Bifunctional 2Hx-2-AF20:

Conjugate ELISA plates were coated with adenovirus (100 ng/well) in 0.1 M sodium carbonate buffer, pH 9.0. Fractions from the Superdex® column representing high molecular weight species (>150 kD, i.e. larger than IgG were diluted 1:100 in phosphate buffered saline pH 7.1 containing, 0.1% BSA, 0.05% TWEEN 20 (dilution buffer) and added to the adenovirus coated wells in duplicate. Parental 2Hx-2 was used as a positive control while parental AF20 was used as a negative control. Bound antibody was detected using a goat—anti—mouse HRP conjugate.

Figure 14D:
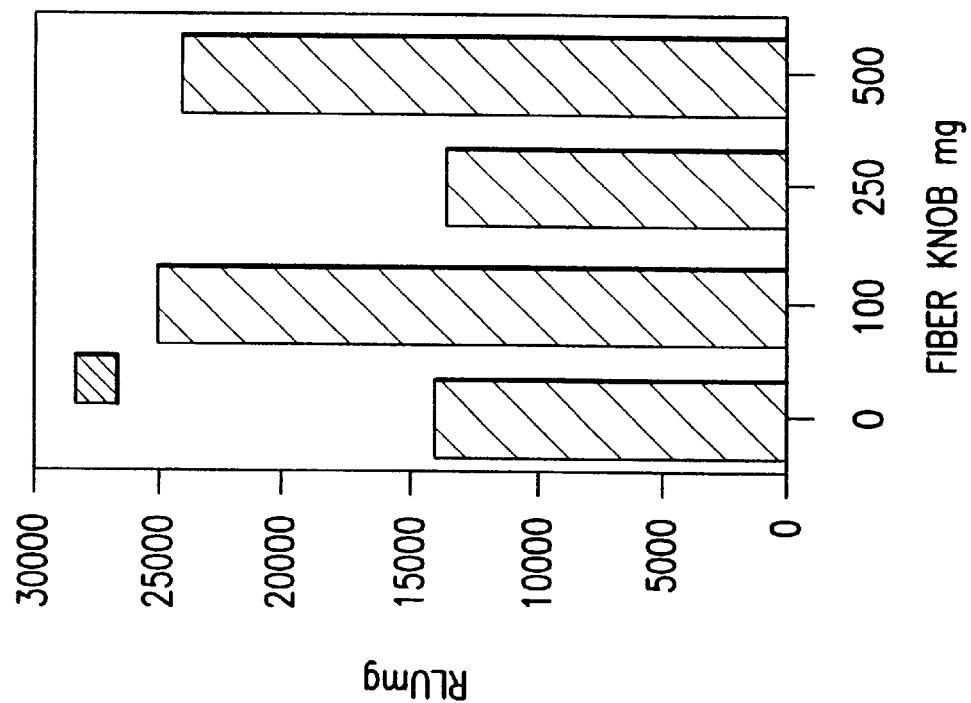
Figure 14C:
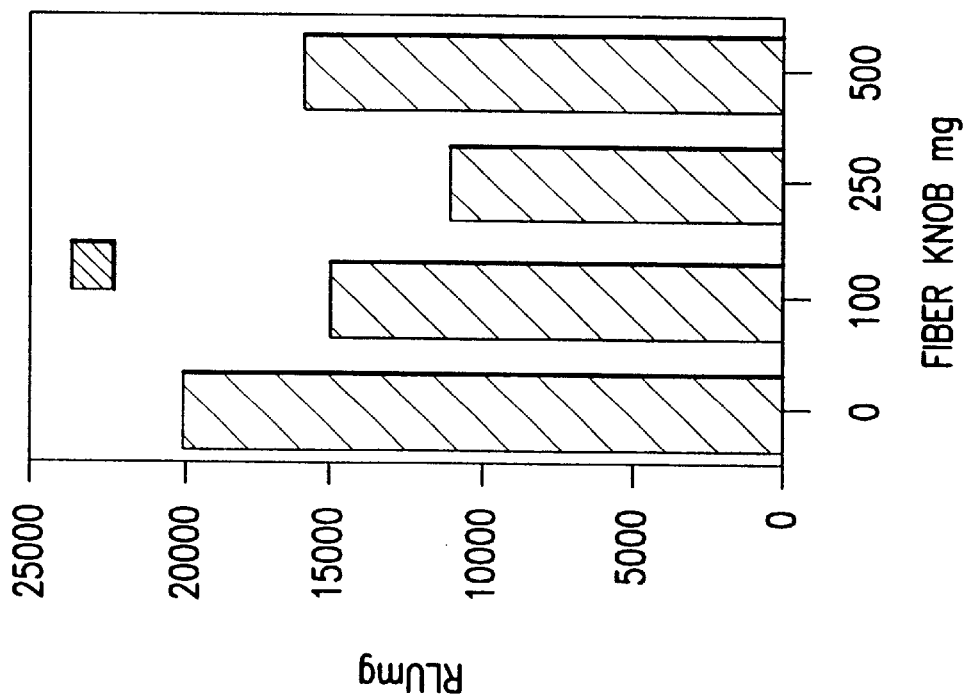

D. Infection Efficiency of Adenovirus in the Presence of 2Hx-AF20 Bifunctional Antibody:

FIG. 14 shows that hepatocellular carcinoma cells (FOCUS cells) treated with adenovirus and pretreated with the above described bifunctional antibody complex exhibited an increase in expression of the β-galactosidase gene compared to cells infected with adenovirus in the absence of the antibody indicating that the bifunctional antibody is able to mediate the infection of FOCUS cells. Moreover, the infection efficiency was not competed by the addition of excess fiber knob protein indicating that the adenovirus infection occurred via an AF20 dependent pathway.

EXAMPLE 11
CONJUGATION OF AF20 ANTIBODY TO ADENOVIRAL PARTICLES USING THE BIFUNCTIONAL MOLECULE TRESYL-PEG-MALEIMIDE

A. Preparation of the Ad2-PEG construct

Ad2 virus expressing β-galactosidase in PBS (prepared as described in Rich et al., 1993, *Human Gene Therapy*, 4:461–476.) was diluted two-fold with 130 mM phosphate buffer pH 7.0. Tresyl-PEG-maleimide at a final concentration of 5% weight/volume was added to the virus, After a 30 minute incubation at room temperature a further 5% of tresyl-PEG-maleimide was added to the remainder of the virus, followed by incubation for an additional 30 minutes to yield a sample of 10% TMPEG-Ad2-maleimide. After a total time of 60 minutes, unreacted PEG was separated form the PEGylated viruses by CsCl centrifugation as described by Rich et al., 1993, *Human Gene Therapy*, 4:461–476. PEGylated virus, 10% TMPEG-Ad2-maleimide was then dialyzed into PBS containing 5% sucrose. Control virus was treated with the non-reactive mPEG (10%) and processed in a similar manner to generate Ad-MPEG.

B. Preparation of the TMPEG-Ad2-AF20 Construct

Sulfhydryl groups were introduced into AF20 IgG antibody using Traut's reagent (Pierce Chemicals). As described herein in Example 10, AF20 IgG was exchanged into PBS pH 8.0 containing 1.0 mM EDTA and labeled with Traut's reagent using a 10-fold molar excess. IgG was labeled for one hour at room temperature after which time any excess Traut's reagent was separated from labeled IgG using a PD-10 (Pharmacia) column equilibrated with phosphate buffered saline (pH 7.1) containing 1.0 mM EDTA. AF20-labeled with Traut's reagent (AF20-SH) was cross-linked to 10% tresyl-Ad2-maleimide by overnight incubation at 4° C. One ml of virus particles (~$4 \times 10^{11}$ particles) was added to 750 µl of a 3.6 µM solution of AF20-SH. The cross-linked bifunctional 10% TMPEG-Ad2-AF20 was purified from monomeric components by gel filtration chromatography using a Superdex® 200 16/60 column which had been pre-equilibrated with PBS pH 7.1. Fractions from the Superdex® column were assayed for AF20 by dot blot analysis, 10% TMPEG-Ad2-AF20 and mPEG-Ad were blotted onto a PVDF membrane and then probed for IgG using an anti-mouse IgG antibody. The blot was developed with the Amersham ECL Western blotting kit by protocols recommended by the manufacturer.

C. Infection Efficiency of TMPEG-Ad2-AF20

Figure 13A:
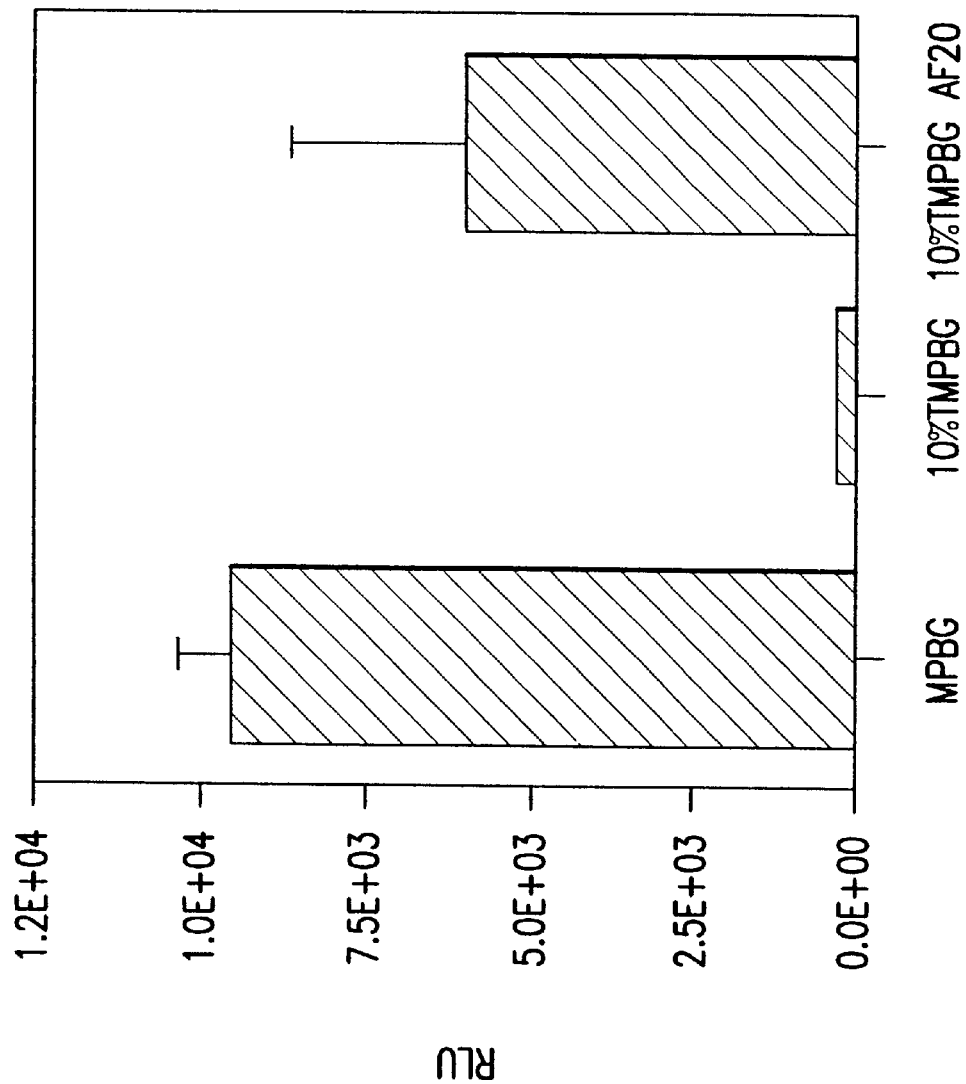
FIGS. 13A–B (A) Graph showing increased transfection efficiency of PEG-AF20 antibody modified virus into FOCUS cells (hepatocellular carcinoma cells). (B) Competition of unmodified adenovirus (MPEG) and PEG-AF20 modified virus (10% TMPEG-AF20) with fiber-knob protein.
Figure 13B:
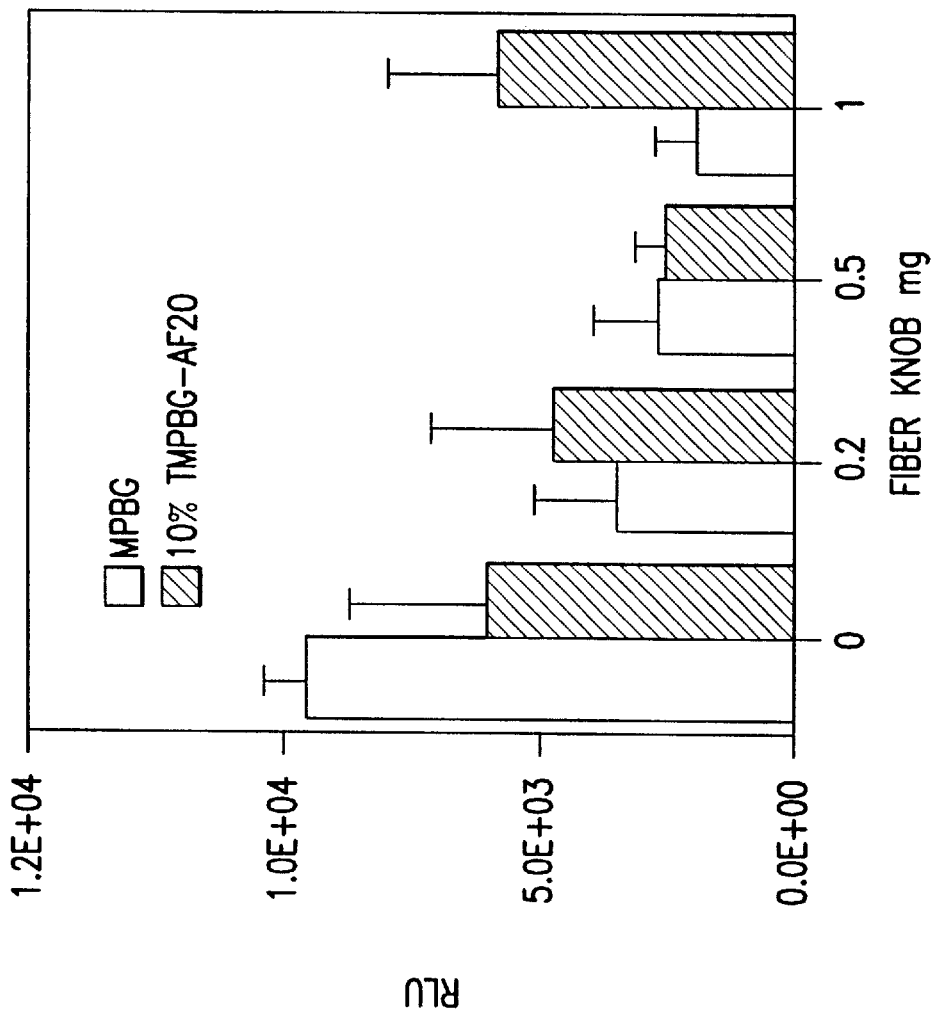

FIG. 13A compares the infectivity of Ad/βgal virus treated with MPEG in FOCUS cells (a hepatocellular carcinoma cell line that over-expresses AF20 antigen) with the infectivity of Ad/βgal treated with 10% PEG maleimide (10% TMPEG) and with the infectivity of Ad/βgal treated with 10% TMPEG followed by conjugation to AF20 (10% TMPEG-AF20). PEGylation of the virus with 10% TMPEG decreased the infectivity of the virus. However conjugation of AF20 to the PEG treated virus restored the infectivity to levels comparable to the MPEG treated virus. Thus AF20 can mediate infection into FOCUS cells. FIG. 13B shows that the restored infectivity mediated by the AF20 is independent of fiber knob because increasing amounts of fiber knob protein did not inhibit the infectivity of the TMPEG-AF20 complex. In contrast, the infectivity of the MPEG treated sample was inhibited by increasing amounts of fiber knob protein. Moreover, the infectivity of 293 human cells is decreased by the PEGylation of the virus. 293 cells are generally readily infected but the PEGlyated virus titers are down approximately 20-fold in these cells. In conclusion, PEGylation of the adenovirus with the tresyl MPEG maleimide molecule decreased the infectivity of the virus presumably due to PEG chains interfering with the binding of fiber knob to its CAR receptor. However, the infectivity of the virus was restored by coupling the AF20 antibody to the virus. This restored infectivity was not inhibitable by fiber knob protein indicating that the modified virus (TMPEG-AF20) used a novel method of entering the cell via the AF20 antigen.

An important aspect in the treatment of hepatocellular carcinomas is that it is desirable only to infect and treat the tumor cells and not healthy hepatocytes. The construct described here has such a property. The infectivity of the TMPEG-AF20 adenovirus is decreased in 293 cells suggesting that this complex no longer can readily recognize its endogenous receptor CAR while the infectivity of the targeted complex TMPEG-AF20 is restored in cells over-expressing the AF20 antigen, e.g. Focus cells. Thus, a targeted complex has been described that can only enter cells expressing the AF20 antigen on its cell surface.

EXAMPLE 12

CHEMICAL COUPLING OF POLY-LYSINE PEPTIDES TO AN ADENOVIRAL VECTOR

Ad2-βgal-4 virus vector in PBS (prepared as described in Rich et al., 1993, *Human Gene Therapy*, 4:461–476) was diluted two-fold with 130 mM phosphate buffer pH 7.0 containing 5% sucrose. Tresyl-PEG maleimide at a final concentration of 1%, or 5% wt/vol was added to the virus. After a 30 minute incubation at room temperature an aliquot of the 5% tresyl-PEG maleimide was removed, incubated on ice and a further 5% tresyl-PEG maleimide was added to bring the final concentration of the tresyl-PEG to 10%. This was incubated for an additional 30 minutes. The 1% tresyl-PEG maleimide sample was incubated on ice after a 30 minute incubation at room temperature. After a total time of 60 minutes, unreacted PEG was separated from the PEGylated virus by CsCl centrifugation as described in Rich et al., 1993, *Human Gene Therapy*, 4:461–476. PEGylated virus (Ad-)βgal-PEG) was then dialyzed into PBS containing 5% sucrose. Two poly-lysine peptides were synthesized each containing a free reactive sulfhydryl on a cysteine residue (p7 (SEQ ID NO:24) and p21 (SEQ ID NO:25)). The peptides were solubilized in PBS containing 5% sucrose at a concentration of 16.8 mg/ml. The pH of the peptide was adjusted to pH 7.0. Approximately 200 µl of this peptide solution was added to $1.5 \times 10^{12}$ virus particles of the various adenovirus-PEG maleimide complexes and allowed to couple for 4 hours at room temperature. Unreacted peptide was removed from the Ad-βgal-PEG-poly-lysine peptide conjugates by dialysis into PBS containing 5% sucrose.

EXAMPLE 13

Ad2-PEG-POLY-LYSINE PEPTIDE INFECTION EFFICIENCY IN NIH 3T3 CELLS AND HUMAN WELL DIFFERENTIATED AIRWAY EPITHELIAL CELLS.

NIH 3T3 cells were infected with unmodified Ad-βgal4, Ad-βgal-PEG, Ad2-βgal-PEG maleimide-1% p7 (SEQ ID NO:24), Ad2-βgal-PEG maleimide-1% p21 (SEQ ID NO:25), Ad2-βgal-PEG maleimide-5% p7 (SEQ ID NO:24), Ad2-βgal-PEG maleimide-5% p21 (SEQ ID NO:25), Ad2-βgal-PEG maleimide-10% p7 (SEQ ID NO:24) or Ad2-βgal-PEG maleimide-10% p21 (SEQ ID NO:25). Virus (moi=100) was allowed to infect the cells for 24 hours, after which time the cells were harvested and assayed for β-galactosidase activity as described above.

Additionally, human well-differentiated airway epithelial cells were infected with Ad2-βgal-10% PEG-pk21 (SEQ ID NO:25), Ad2-βgal-10% PEG-pk7 (SEQ ID NO:24), or Ad2-βgal-10% PEG all at an MOI (multiplicity of infection) of either 5 or 50 as described above in Example 9.

FIG. 15 shows that there is a significant increase in transduction of NIH 3T3 cells infected with the Ad2-βgal-PEG 10% p21 (SEQ ID NO:25) conjugate compared to the Ad2-βgal-PEG or Ad2-βgal alone suggesting that the poly-lysine peptide, when coupled to the surface of the 10% Ad-PEG maleimide virus, provides at least a 2 log increase in vector infection efficiency of NIH 3T3 cells. The positively charged peptide linked to the virus via the bifunctional molecules of the present invention provides an increased association with the cells (and likely with the negatively charged cellular membrane).

Figure 16:
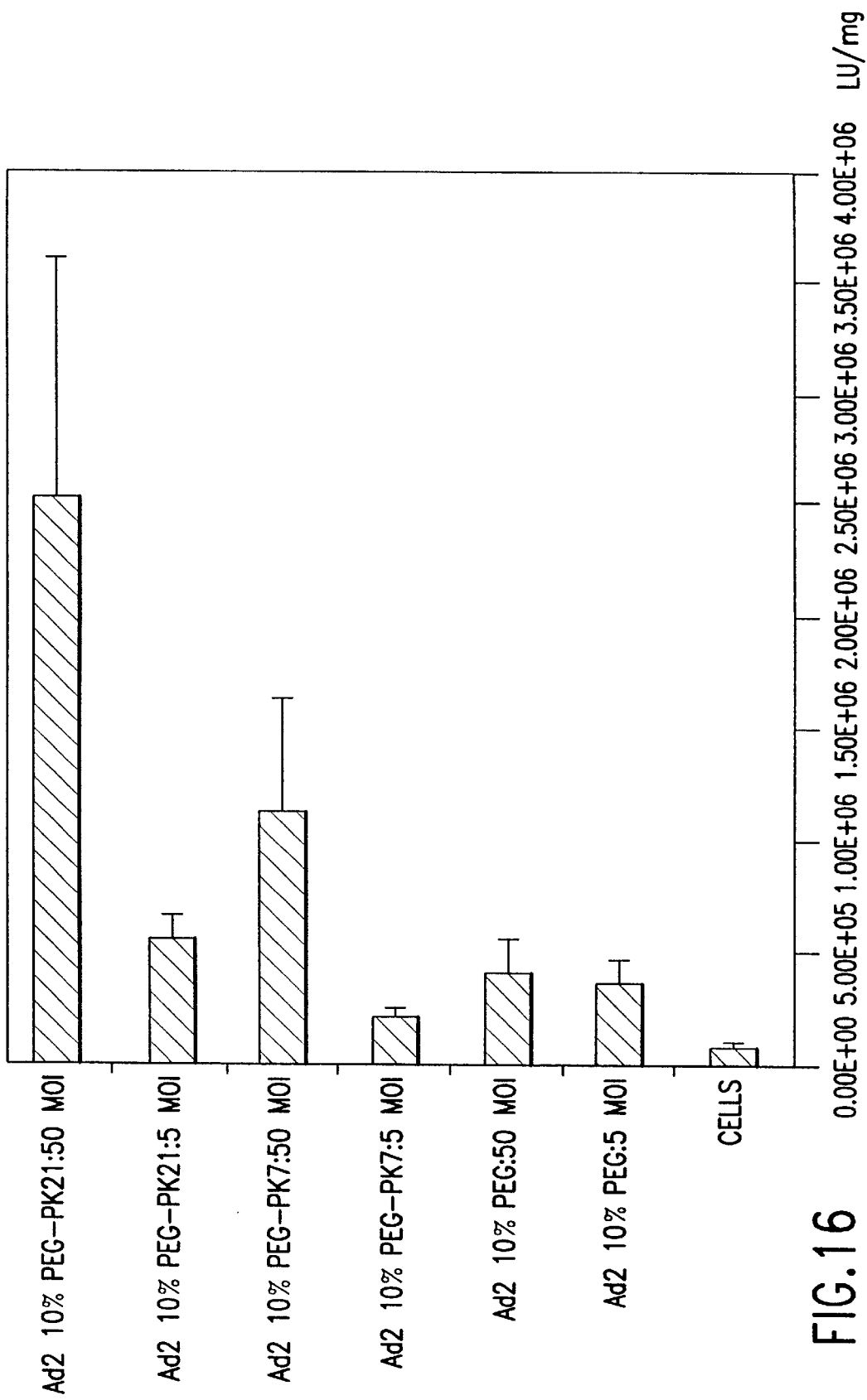
FIG. 16 is a graph showing the infection efficiency of bifunctional PEG-poly-lysine peptide modified adenoviruses. Infection efficiency was measured by the ability of well-differentiated human airway epithelial cells to express the gene product (β-galactosidase).

FIG. 16 shows that there is a significant increase in infection efficiency of human well differentiated airway epithelial cells infected with ad-βgal-10% PEG-pk21 and ad-βgal-10% PEG-pk7 (up to 7 fold) compared to ad-βgal-10% PEG alone. Again demonstrating that the positively charged peptides linked to the virus via the bifunctional molecules of the present invention provide an increased association with well-differentiated airway epithelial cells.

EXAMPLE 14
Adβgal-PEG-bFGF INFECTION EFFICIENCY OF HUMAN OVARIAN CARCINOMA CELLS.

1. Cell Culture

Human ovarian carcinoma cells (SKOV3.ip1) were cultured in DMEM (Dulbecco's Modified Medium) with 10% fetal bovine serum according to standard -tissue culture techniques.

2. Preparation of bFGF-modified PEGylated Adenovirus

25 μg of basic fibroblast growth factor (bFGF) (Sigma Chemicals, St. Louis Mo.) was reconstituted with 50 μl dH$_2$O containing 25 mM DTT (dithiothreitol) and incubated on ice for 30 minutes to reduce disulfides. DTT was removed from the reaction using BioSpin® 6 columns (BioRad) pre-equilibrated with PBS pH 7.2. Any remaining DTT was further removed by a two hour dialysis step against PBS ph 7.2.

Reduced bFGF was added to adenovirus previously modified with TMPEG-maleimide at 1%. Coupling to bFGF and virus went for 24 hours at 4° C. Uncoupled bFGF was removed by size exclusion chromatography on SUPERDEX 200 (Pharmacia). The excluded volume was collected and sucrose added to a final concentration of 5%. The coupled virus was then sterile filtered and frozen in aliquots at –80° C. for long term storage. Alternatively, uncoupled bFGF can be removed by extended dialysis against PBS, 5% sucrose, pH 7.2.

3. Results

Figure 19:
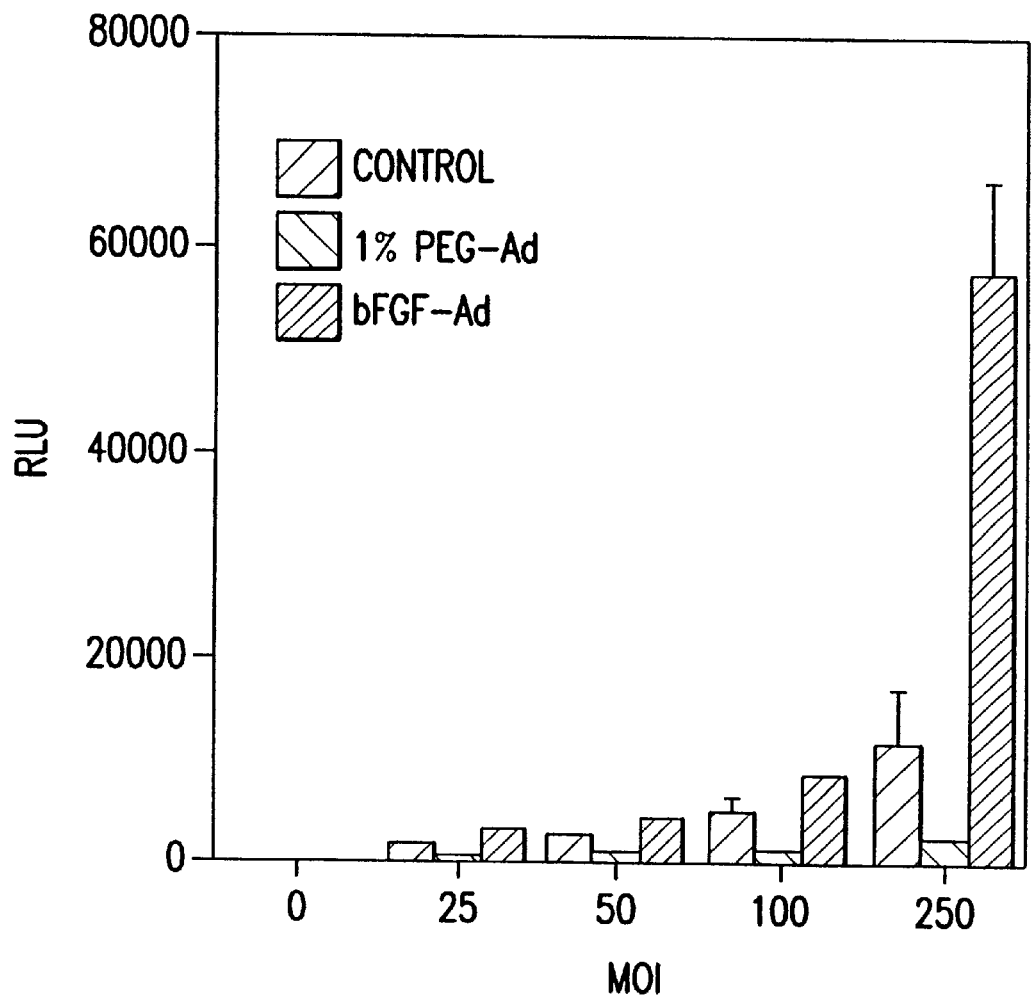
FIG. 19 is a graph showing the infection efficiency of bifunctional PEG-basic fibroblast growth factor (bFGF) modified adenovirus. Infection efficiency was measured by the ability of human ovarian carcinoma cells to express the gene product β-galactosidase.

FIG. 19 shows that coupled bFGF to Ad-βgal virus increased the infection efficiency in human ovarian carcinoma cells by approximately four-fold. The bFGF receptor is upregulated in many tumor cell lines and it is therefore a versatile tumor cell targeting ligand. These results demonstrate that bFGF can mediate the infection of a tumor cell line when linked to a delivery vehicle.

EXAMPLE 15
TARGETING ADENOVIRAL PARTICLES VIA THE CARBOHYDRATE STRUCTURE OF FIBER.

1. Coupling of the Carbohydrate Moiety of Adenovirus

Adenovirus was oxidized with increasing concentrations of sodium periodate at two pH values, 5.5 and 7.2. Following oxidation, the oxidized carbohydrate on the virus particle was coupled to the fluorescent probe Texas Hydrazide Red. Excess label was removed by buffer exchange on PD-10 columns pre-equilibrated in PBS.

Excitation was set at 591 nm and emission was monitored at 612 nm. Fluorescence units were normalized to the measured A280 of the virus samples.

| mM Periodate | pH 5.5 (A280) | pH 7.2 (A280) |
|---|---|---|
| 0.01 | 30789 | 13390 |
| 1.0 | 71064 | 18156 |
| 5.0 | 44485 | 59452 |
| 10. | 54250 | 70979 |

The data above demonstrated that the carbohydrate moiety on fiber can be coupled to a molecule (in this case Texas Hydrazide Red) as evidenced by the increase in A280 values shown. This method is useful in coupling adenovirus to targeting moieties.

EXAMPLE 16
TARGETING ADENOVIRAL VECTORS TO THE LIVER

The following example describes a vector which includes several key features in order to enhance gene delivery to the liver in vivo. Recombinant AAV vectors have been shown to be effective in gene transfer to hepatocytes (Snyder et al., 1997, Nat. Genet. 16: 270–276). However, a major drawback associated with AAV vectors is that only 3–5% of hepatocytes are typically transduced. Due to this poor efficiency of transduction, high viral doses are required which can result in the development of adverse immunological responses, thus limiting effective re-administration of vector. To address this problem, we developed approaches to increase the efficiency of AAV entry mechanism which mimics that of adenovirus, i.e., binding and internalization via CAR receptor or other hepatocyte cell receptor. To achieve this, it is possible to couple purified fibre knob protein via bifunctional PEG molecules to the surface of AAV. Fibre knob is the capsid protein located at the distal end of fibre which facilitates binding of adenovirus to CAR.

Another such approach is to augment the entry of adenovirus into hepatocytes at low viral doses, thus eliminating or reducing some of the toxicity associated with transduction of hepatocytes by adenovirus at high viral doses. Other targeting ligands which can be attached to AAV or Ad for targeting to the liver are ligands which can bind to the asialoglycoprotein receptor examples include, asialofetuin, asialoglycoprotein, galactose, galactosamine or a tetraantannary galactose ligand as described by Plank et al., 1992, Bioconjugate Chem. 3, 533–539. AAV virus particles in general can be targeted to a variety of other receptors using bifunctional PEG molecules including bFGF receptor or GMCSF receptor. Targeting to these receptors would involve coupling the ligands bFGF or GMCSF to the virus using bifunctional PEF molecules.

Another polysaccharide which can be coupled to either AAV or Ad for targeting to the liver is Pullulan. Pullulan is a polysaccharide with high affinity for the liver (Tabata et al., 1999; Journal of Interferon and Cytokine Research 19:287–292). It is a linear, non-ionic polysaccharide with a repeated unit of maltotriose condensed through an α-1,6 linkage. One approach to coupling repeating sugar residues to the virus using bifunctional PEG molecules is to synthesize a tresyl-PEG-polylysine molecule. The tresyl group can attach to the virus via ε-amino groups of lysines on the virus, while the polylysine peptide attached to the other end of the bifunctional PEG molecule can act as a platform to attach sugar residues by a procedure described by Midoux, et al., 1993, Nucleic Acid Research 21:871–878; Erbacher et al., 1995, Bioconj. Chem. 6:401–410; and Kollen et al., 1996, Hum Gen. Ther. 7:1577–1586. This approach involves coupling 4-isothiocyanatophenyl-derivatives of sugars to poly-L-lysine p-toluene sulfonate salt to dimethylsulfoxide in the presence of diisopropylethylamine.

Other examples of ligands that can be attached to AAV/Ad using bifunctional PEG molecules for delivery to the liver include the hepatocyte growth factor (Nguyen et al., Hum. Gen. Ther. 1998;9;2469–2479). Another receptor found on hepatocytes which could be targeted is the serpin enzyme complex receptor (SEC-R). A synthetic peptide ligand (C1315) based in sequence on amino acids 346–374 of human α$_1$-antitrypsin binds to this receptor with high affinity (Ziady et al., Am. J. Phys 1997: 273:G545–G552; Ziady et al., Gene Therapy 1998; 5:1685–1697). This peptide can be synthesized with a cysteine or reactive sulfhydryl which can in turn to couple to the bifunctional tresyl-PEG-maleimide molecule described above.

Covalent Attachment of Fibre Knob Protein to Adenovirus/ AAV

Ad2-βgal-4 virus or AAV-βgal in PBS (prepared as described in Rich et al. (1993) is diluted two fold with 130 mM phosphate buffer pH 7 containing 5% sucrose. Tresyl-PEG-malemide at a final concentration of 5% wt/vol is added to the virus, after a 30 min incubation at room temperature a further 5% of Tresyl-PEG-malemide is added and incubated for an additional 30 min. After a total time of 60 min, unreacted PEG is separated from PEGylated virus by gel filtration chromatography. Sulfhydryl groups are introduced into the virus via Traut's reagent and coupled to the malemide groups on the PEGylated adenovirus/AAV. Ad-PEG-fibre knob or AAV-PEG-fibre knob is assayed for transduction of hepatocytes in vitro and in vivo.

Attachment of Multiple Targeting Ligands to a Single PEG-virus Particle

In order to facilitate both the binding and internalization of a PEG-virus complex into a target cell it may be beneficial to couple several different ligands to the surface of one PEG-virus particle. The aim would be to couple multiple targetting ligands, each of which contributes to a defined event in the overall process of binding and internalization of a PEG-virus particle into a cell of choice. For example the peptide sss.17 selected by phage biopanning well-differentiated airway epithelia promotes binding to the epithelial cell surface but not internalization. Coupling sss.17 to a PEG-virus complex in addition to coupling a cyclic RGD peptide (which is known to promote internalization via binding to cell surface integrins) would generate a PEG-virus-ligand complex that now can bind with high affinity to and be internalized into an epithelial cell. Other examples of potential combinations of ligands are listed below.

| | |
|---|---|
| sss.17 | cyclic RGD |
| pK21 | cyclic RGD |
| pK7 | cyclic RGD |
| sss.17 | U7 peptide |
| pK21 | U7 peptide |
| pK7 | U7 peptide |
| FGF | cyclic RGD |
| FGF | U7 peptide |

U7 peptide is a peptide encoding residues 13–19 (CLNGGTC) of the N-terminal portion of Urokinase Plasminogen Activator (Apella et al.,1993; J Biol Chem 262; 4437–4440) which can promote internalization into a cell via the UPA receptor. pK21 and pK7 are polylysine peptides with 21 and 7 lysine residues respectively Three or more ligands could also be coupled to the PEG-virus. Examples of combinations of targetting ligands are provided: These combinations are of particular interest for binding and internalization into lung epithelial cells but a similar approach could be taken for increasing the binding and internalization of PEG-virus complexes into a variety of target cells.

| | | |
|---|---|---|
| sss.17 | cyclic RGD | U7 peptide |
| sss.17 | pK21 | cyclic RGD |
| sss.17 | pK7 | cyclic RGD |
| U7 peptide | pK21 | cyclic RGD |

The disclosures of all references disclosed herein are hereby incorporated by reference. The invention has been described in detail with particular reference to preferred embodiments thereof. However, it is contemplated that modifications and improvements within the spirit and teachings of this invention may be made by those in the art upon considering the present disclosure. Such modifications and improvements constitute part of the present claimed invention.

What is claimed is:

1. A nucleic acid delivery vehicle for transfecting and/or infecting a target liver cell, said nucleic acid delivery vehicle comprising:
    an adeno-associated virus (AAV) vector comprising a transgene, said AAV vector being covalently bound to,
    a polyethylene glycol linker, said polyethylene glycol linker also being covalently bound to,
    a cell surface molecule-binding moiety selected from the group consisting of fibre knob protein, Pullulan, hepatocyte growth factor, galactose and asialofetuin.

2. A nucleic acid delivery vehicle for transfecting and/or infecting a target liver cell, said nucleic acid delivery vehicle comprising:
    an adenovirus vector comprising a transgene, said adenovirus vector being covalently bound to,
    a polyethylene glycol linker, said polyethylene glycol linker also being covalently bound to,
    a cell surface molecule-binding moiety selected from the group consisting of fibre knob protein, Pullulan, hepatocyte growth factor, galactose and asialofetuin.

* * * * *